US011453892B2

(12) United States Patent
Hatoum

(10) Patent No.: US 11,453,892 B2
(45) Date of Patent: Sep. 27, 2022

(54) CRISPR-CAS10 SYSTEMS AND METHODS FOR PHAGE GENOME EDITING

(71) Applicant: The Board of Trustees of The University of Alabama, Tuscaloosa, AL (US)

(72) Inventor: Asma Hatoum, Northport, AL (US)

(73) Assignee: The Board of Trustees of The University of Alabama, Tuscaloosa, AL (US)

( * ) Notice: Subject to any disclaimer, the term of this patent is extended or adjusted under 35 U.S.C. 154(b) by 202 days.

(21) Appl. No.: 15/910,620

(22) Filed: Mar. 2, 2018

(65) Prior Publication Data

US 2018/0251787 A1    Sep. 6, 2018

Related U.S. Application Data

(60) Provisional application No. 62/465,929, filed on Mar. 2, 2017.

(51) Int. Cl.
| | |
|---|---|
| *C12N 15/86* | (2006.01) |
| *C12N 15/74* | (2006.01) |
| *C12N 15/11* | (2006.01) |
| *C12N 15/90* | (2006.01) |
| *C12N 1/20* | (2006.01) |
| *C12R 1/44* | (2006.01) |
| *C12N 9/22* | (2006.01) |
| *C12N 9/12* | (2006.01) |

(52) U.S. Cl.
CPC ............. *C12N 15/86* (2013.01); *C12N 1/205* (2021.05); *C12N 9/1276* (2013.01); *C12N 9/22* (2013.01); *C12N 15/11* (2013.01); *C12N 15/74* (2013.01); *C12N 15/902* (2013.01); *C12N 2310/20* (2017.05); *C12N 2710/00042* (2013.01); *C12N 2710/00045* (2013.01); *C12N 2795/10121* (2013.01); *C12N 2795/10221* (2013.01); *C12N 2795/10321* (2013.01); *C12R 2001/44* (2021.05)

(58) Field of Classification Search
CPC ...... C12N 15/86; C12N 1/205; C12N 9/1276; C12N 9/22; C12N 15/11; C12N 15/74; C12N 15/902; C12N 2310/20; C12N 2710/00042; C12N 2710/00045; C12N 2795/10121; C12N 2795/10221; C12N 2795/10321; C12R 2001/44
See application file for complete search history.

(56) References Cited

U.S. PATENT DOCUMENTS

2017/0333500 A1* 11/2017 Hatfield .................. C12N 7/00

OTHER PUBLICATIONS

Ando, et al., (2015) Engineering Modular Viral Scaffolds for Targeted Bacterial Population Editing. Cell Syst., 1, 187-196.
Barrangou, et al., (2007) CRISPR provides acquired resistance against viruses in prokaryotes. Science, 315, 1709-1712.
Beaucage and Carruthers, (1981) Deoxynucleoside phosphoramidites—A new class of key intermediates for deoxypolynucleotide synthesis. Tetrahedron Lett. 22:1859-1862.

(Continued)

*Primary Examiner* — Jeremy C Flinders
*Assistant Examiner* — Taryn Kimberly Wood
(74) *Attorney, Agent, or Firm* — Meunier Carlin & Curfman LLC

(57) ABSTRACT

The present disclosure relates to CRISPR-Cas10 systems and methods for phage genome editing.

8 Claims, 6 Drawing Sheets

Specification includes a Sequence Listing.

(56) References Cited

OTHER PUBLICATIONS

Bikard, et al., (2014). Development of sequence-specific antimicrobials based on programmable CRISPR-Cas nucleases. Nat Biotechnol 32:1146-1150.
Borysowski, et al., (2011) Potential of Bacteriophages and Their Lysins in the Treatment of MRSA. Biodrugs, 25, 347-355.
Box, et al., (2016). Functional Analysis of Bacteriophage Immunity through a Type I-E CRISPR-Cas System in Vibrio cholerae and Its Application in Bacteriophage Genome Engineering. J Bacteriol 198:578-590.
Brouns, et al., (2008) Small CRISPR RNAs guide antiviral defense in prokaryotes. Science, 321, 960-4.
Brussow, et al., (2004) Phages and the Evolution of Bacterial Pathogens : from Genomic Rearrangements to Lysogenic Conversion. Microbiol. Mol. Biol. Rev., 68, 560-602.
Cater, et al., (2017) A Novel *Staphylococcus podophage* Encodes a Unique Lysin with Unusual Modular Design. mSphere, 2, 1-9.
CDC, "Antibiotic Resistance Threats in the US", 2013, 114 pages.
CDC. 2004. National Nosocomial Infections Surveillance (NNIS) System Report, data summary from Jan. 1992 through Jun. 2004, issued Oct. 2004. Am J Infect Control 32:470-485.
Cogen, et al. (2010) Selective antimicrobial action is provided by phenol-soluble modulins derived from *Staphylococcus epidermidis*, a normal resident of the skin. J. Invest. Dermatol., 130, 192-200.
Cooper, et al., (2016) Adapting Drug Approval Pathways for Bacteriophage-Based Therapeutics. Front. Microbiol., 7, 1-15.
Deghorain M, Van Melderen L. (2012) The staphylococci phages family: An overview. Viruses 4:3316-3335.
Deveau, et al., (2008) Phage Response to CRISPR-Encoded Resistance in *Streptococcus thermophilus*. J. Bacteriol., 190, 1390-1400.
Fernández, et al., (2017) Low-level predation by lytic phage philPLA-RODI promotes biofilm formation and triggers the stringent response in *Staphylococcus aureus*. Sci. Rep., 7, 1-14.
Flores, et al., (2011) Statistical structure of host—phage interactions. Proc. Natl. Acad. Sci., 108, E288.
Gibson, et al., (2009) Enzymatic assembly of DNA molecules up to several hundred kilobases. Nat Meth, 6, 343-345.
Gill, et al. (2005) Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidermidis* Strain. J. Bacteriol., 187, 2426-2438.
Godde, et al., (2006) The repetitive DNA elements called CRISPRs and their associated genes: Evidence of horizontal transfer among prokaryotes. J. Mol. Evol., 62, 718-729.
Goldberg, et al., (2014) Conditional tolerance of temperate phages via transcription-dependent CRISPR-Cas targeting. Nature, 514, 633-637.
Górski, et al. (2012) Phage as a Modulator of Immune Responses: Practical Implications for Phage Therapy. Adv. Virus Res., 83, 41-71.
Grice, et al., (2011) The skin microbiome. Nat. Rev. Microbiol., 9, 244-253.
Grissa, et al., (2007) The CRISPRdb database and tools to display CRISPRs and to generate dictionaries of spacers and repeats. BMC Bioinformatics, 8, 172.
Haft, et al., (2005) A guild of 45 CRISPR-associated (Cas) protein families and multiple CRISPR/cas subtypes exist in prokaryotic genomes. PLoS Comput. Biol., 1, 0474-0483.
Hatoum-Aslan, et al., (2011) Mature clustered, regularly interspaced, short palindromic repeats RNA (crRNA) length is measured by a ruler mechanism anchored at the precursor processing site. Proc Natl Acad Sci 108:21218-21222.
Hatoum-Aslan, et al., (2014) Genetic characterization of antiplasmid immunity through a type III-A CRISPR-cas system. J Bacteriol 196:310-317.
Hatoum-Aslan, et al., (2013) A ruler protein in a complex for antiviral defense determines the length of small interfering CRISPR RNAs. J Biol Chem 288:27888-27897.
Hatoum-Aslan, et al., (2014) Impact of CRISPR immunity on the emergence and virulence of bacterial pathogens. Curr. Opin. Microbiol., 17, 82-90.
Iwase, et al., (2010) *Staphylococcus* epidermidis Esp inhibits *Staphylococcus aureus* biofilm formation and nasal colonization. Nature, 465, 346-349.
Jiang, et al., (2013) CRISPR-assisted editing of bacterial genomes. Nat. Biotechnol., 31, 233-239.
Kaźmierczak, et al., (2014) Facing Antibiotic Resistance: *Staphylococcus aureus* Phages as a Medical Tool. Viruses 6:2551-2570.
Keen, et al., (2017) Novel 'Superspreader' Bacteriophages Promote Horizontal Gene Transfer by Transformation. MBio, 8, 1-12.
Kiro, et al., (2014) Efficient engineering of a bacteriophage genome using the type I-E CRISPR-Cas system. RNA Biol., 11, 42-4.
Kluytmans, et al. (1997) Nasal Carriage of *Staphylococcus aureus*: Epidemiology, Underlying Mechanisms, and Associated Risks. Clin. Microbiol. Rev., 10, 505-520.
Koonin, et al., (2017) Diversity, classification and evolution of CRISPR-Cas systems. Curr. Opin. Microbiol., 37, 67-78.
Kwan, et al., (2005) The complete genomes and proteomes of 27 *Staphylococcus aureus* bacteriophages. Proc. Natl. Acad. Sci. U. S. A., 102, 5174-9.
Lai, et al., (2010) Activation of TLR2 by a Small Molecule Produced by *Staphylococcus epidermidis* Increases Antimicrobial Defense against Bacterial Skin Infections. 130, 2211-2221.
Lemay, et al., (2017) Genome Engineering of Virulent Lactococcal Phages Using CRISPR-Cas9. ACS Synth. Biol., doi: 10.10.
Loessner, et al., (1996) Construction of luciferase reporter bacteriophage A511 :: luxAB for rapid and sensitive detection of viable Listeria cells . These include: Construction of Luciferase Reporter Bacteriophage A511: luxAB for Rapid and Sensitive Detection of Viable Lister. Appl. Environ. Microbiol., 62, 1133-1140.
Lowy, F.D. (1998) *Staphylococcus aureus* infections. N. Engl. J. Med., 339, 520-532.
Makarova, et al. (2015) An updated evolutionary classification of CRISPR-Cas systems. Nat. Rev. Microbiol., 13, 722-736.
Maniv, et al., (2016) Impact of different target sequences on type III CRISPR-Cas immunity. J. Bacteriol., 198, 941-950.
Marinelli, et al., (2008) BRED : A Simple and Powerful Tool for Constructing Mutant and Recombinant Bacteriophage Genomes. PLoS One, 3, e3957.
Marraffini LA. (2015) CRISPR-Cas immunity in prokaryotes. Nature 526:55-61.
Marraffini, L.A. and Sontheimer, E.J. (2008) CRISPR interference limits horizontal gene transfer in staphylococci by targeting DNA. Science, 322, 1843-1845.
Marraffini, et al., (2010) Self vs. non-self-discrimination during CRISPR RNA-directed immunity. Nature, 463, 568-571.
Martel, et al., (2014) CRISPR-Cas: An efficient tool for genome engineering of virulent bacteriophages. Nucleic Acids Res., 42, 9504-9513.
Matteucci, et al., (1981) Synthesis of deoxyoligonucleotides on a polymer support J. Am. Chem. Soc.,103:3185.
Mojica, et al., (2009) Short motif sequences determine the targets of the prokaryotic CRISPR defence system. Microbiology, 155, 733-740.
Monk, et al., (2012) Transforming the Untransformable : Application of Direct Transformation To Manipulate Genetically *Staphylococcus aureus* and *Staphylococcus epidermidis*. MBio, 3, e00277-11.
Naik, et al. (2015) Commensal-dendritic-cell interaction specifies a unique protective skin immune signature. Nature, 520, 104-108.
Otto, M. (2009) *Staphylococcus epidermidis*—the 'accidental' pathogen. Nat. Rev. Microbiol., 7, 555-567.
Pires, et al., (2016) Genetically Engineered Phages: a Review of Advances over the Last Decade. Microbiol. Mol. Biol. Rev., 80, 523-543.
Samai, et al., (2015) Co-transcriptional DNA and RNA cleavage during type III CRISPR-cas immunity. Cell, 161, 1164-1174.
Semenova, et al., (2011) Interference by clustered regularly interspaced short palindromic repeat ( CRISPR ) RNA is governed by a seed sequence. Proc. Natl. Acad. Sci., 108, 10098-10103.

(56) References Cited

OTHER PUBLICATIONS

Shmakov, et al., (2015) Discovery and Functional Characterization of Diverse Class 2 CRISPR-Cas Systems. Mol Cell 60:385-397.
Stryjewski, et al. (2008) Skin and Soft-Tissue Infections Caused by *Staphylococcus aureus*. Clin. Infect. Dis., 46, S368-377.
Tormo, et al., (2008) *Staphylococcus aureus* Pathogenicity Island DNA Is Packaged in Particles Composed of Phage Proteins. J. Bacteriol., 190, 2434-2440.
Uchiyama, et al., (2014) Intragenus generalized transduction in *Staphylococcus* spp. by a novel giant phage. ISME J., 8, 1-4.
Wiedenheft, et al. (2011) RNA-guided complex from a bacterial immune system enhances target recognition through seed sequence interactions. Proc. Natl. Acad. Sci., 108, 10092-10097.
Walker et al., (2017), Molecular determinants for CRISPR RNA maturation in the Cas10-Csm complex and roles for non-Cas nucleases, Nucleic Acids Research, vol. 45, Issue 4, Feb. 28, 2017, pp. 2112-2123.

* cited by examiner

SEQUENCE LISTING

<160> NUMBER OF SEQ ID NOS: 112

<210> SEQ ID NO 1
<211> LENGTH: 7346
<212> TYPE: DNA
<213> ORGANISM: Artificial Sequence
<220> FEATURE:
<223> OTHER INFORMATION: Synthetic constructs

<400> SEQUENCE: 1

```
atctttatat aaatggaggt taaaatgaat aaaaaaaata tattaatgta tggctcttta      60
ttacatgata tagggaaaat tatatatcga agtggtgatc atacatttc aagaggtacg     120
cattcaaaat taggtcatca attttttgtcc caattttcag aatttaaaga caacgaagtg    180
cttgataacg ttgcttatca tcattacaaa gaactcgcaa aagctaattt agataatgat    240
aatacagctt atattaccta tattgcggat aatattgcga gtggtattga tagaagagat    300
attatagaag aaggcgatga agaatacgaa aaacaactat ttaattttga taaatataca    360
ccgctatata gtgtgtttaa tattgtgaat tctgaaaaat tgaaacaaac aaacgggaag    420
tttaaatttt ctaatgaaag taatattgaa tatcctaaaa ctgaaaacat tcaatattca    480
agtggaaatt atacaacatt aatgaaagat atgagtcatg atttagagca caaattaagt    540
attaaagaag gtacatttcc ttcattatta caatggacgg aaagtctatg gcaatatgta    600
cctagttcga caaataaaaa ccaattaatt gatatttctc tttatgatca tagtcgtatt    660
acatgtgcca tcgccagttg tatatttgat tatttaaatg aaaataacat acataattac    720
aaagatgaat tgttctcaaa gtatgaaaat accaaatcat tttatcaaaa gaagcttttt    780
ttactactta gtatggatat gagtggtatt caagatttta tttacaatat aagcggttct    840
aaagcattaa agagtctaag atctcgtagt tttatttag aactcatgct tgaagtaatc    900
gttgatcaat tattagaaag attagaatta gcacgagcaa atcttttgta tacaggtggt    960
ggccatgctt atttattagt gtctaatact gataaagtga agaaaaaaat aactcaattt   1020
aataatgaat taaaaaatg gtttatgtca gaatttacta cagatctttc attatcaatg   1080
gcttttgaaa atgtagtgg cgatgattta atgaatacaa gtggtaatta tagaactatt   1140
tggcgtaatg ttagcagcaa actttctgat attaaagcgc ataaatattc cgcggaagat   1200
atattaaaat taaatcattt tcattcgtat ggagatcggg aatgtaaaga atgtttaaga   1260
agtgacatag atattaatga tgatggacta tgtagtatat gtgaaggaat tattaatata   1320
tcaaatgatt taagagataa atcattcttt gtactgtcag aaactggaaa attaaaaatg   1380
ccattcaata aatttatatc ggttattgat tatgaagagg cagaaatgtt agtacaaaat   1440
aataatcaag ttcgtattta cagtaaaaat aaaccatata taggcatagg aatatcaaca   1500
aatttatgga tgtgtgatta cgactatgct agtcaaaatc aagatatgag agaaaaaggt   1560
attggaagtt atgtagatag agaagaaggg gttaagcgtt taggcgtggt acgtgccgat   1620
```

-continued

```
atagataatc tcggtgctac atttatatct ggaattccag aaaaatataa ttcaatttca    1680
agaacagcta cattgtctcg tcaattatca ttattttta aatacgaatt aaatcattta     1740
ttagaaaatt atcaaattac tgctatatat tcaggcggtg acgatttatt tttaatcggt    1800
gcatgggatg acattataga agcaagcatt tatataaatg acaaatttaa agagtttact    1860
cttgataaac taacattgtc tgccggggtt ggaatgttta gtggtaagta cccagtttct    1920
aaaatggctt ttgagacagg acgacttgaa gaagcggcta agactggtga aaaaaatcag    1980
atatctcttt ggttacaaga aaaagtatat aactgggatg agtttaaaaa gaatatctta    2040
gaagaaaaac ttctcgtttt acaacagggg ttttctcaaa cagatgaaca cgggaaagcc    2100
ttcatttata aaatgctcgc tttactgaga aataatgaag ctattaatat tgctcgttta    2160
gcttacttat tagcaagaag caagatgaat gaggatttta cgtctaaaat tttttaattgg   2220 gctcaaaacg acaaagataa aaatcaatta attacagcgt tagagtatta tatttatcaa    2280
ataagggagg ctgattgagt atgatattag ctaaaactaa aagtggtaaa acgatagatt    2340
tgacttttgc acatgaggtc gtaaaaagta atgtaaaaaa tgttaaagat agaaaaggca    2400
aagaaaaaca agtttatttt aacgggctta caacaagcaa gttaagaaat ttaatggagc    2460
aggtaaatag actttatact attgcattta attcgaatga ggatcaattg aatgaagaat    2520
tcattgatga attagaatat ttaaaaatta aatttatta tgaagcagga cgagaaaaaa    2580
gcgttgatga attttttaaaa aaaacattga tgtttccaat tattgataga gtgataaaaa    2640
aagaatcaaa aaaatttttc ttagattatt gtaaatactt tgaagcttta gttgcatacg    2700
ctaaatatta tcaaaaggag gattaatatg tattcaaaaa ttaaaatttc aggaacaatt    2760
gaagtagtta ctggtttaca catcggcgga ggcggtgaat ctagtatgat tggagcaatt    2820
gattctcctg tagttagaga tttgcaaacc aaattaccta tcatacctgg cagttcaatc    2880
aaaggaaaaa tgagaaattt attagcaaaa cattttggct tgaaaatgaa acaagagagt    2940
cataaccaag atgatgaacg tgtattaaga ttatttggct caagtgaaaa aggaaatatc    3000
caaagagctc gtctacaaat ttctgatgca ttcttttctg aaaagacaaa agagcatttt    3060
gcgcaaaatg atattgccta tacagaaacg aaatttgaga atacaattaa tcgtttaact    3120
gcagttgcaa acccaagaca aattgaaaga gtaacaagag gatctgagtt tgactttgta    3180
tttatttaca atgtcgatga agagtcgcaa gttgaggatg attttgagaa tattgaaaaa    3240
gcgattcact tattagagaa tgactatctt ggtggcggcg gaactagagg taacggacgt    3300
attcaattta aagatacaaa tatcgagaca gttgttggag aatacgatag tacaaatctt    3360
aaaattaagt aggtgaatga cattggcaac aaaagtattt aaactttctt ttaagactcc    3420
tgttcatttt ggaaaaaaac ggttgtcaga tggtgaaatg acaatcactg ctgatacttt    3480
gtttagtgct ttatttattg aaacacttca attgggtaaa gataccgatt ggttattaaa    3540
tgatttaatc attagtgata catttcctta tgagaatgag ctttattatc ttcctaaacc    3600
tttgataaaa attgactcta aagaagaaga taaccataaa gcatttaaaa agttaaaata    3660
tgttccggtt catcactata atcaatattt aaatggagag ttaagcgctg aagatgcgac    3720
agatttaaat gatattttta atattgggta tttttctcta caaacaaagg tttcattaat    3780
agcacaagaa actgattcaa gtgctgatag tgaaccttat tcagtgggaa catttacttt    3840
tgaacctgaa gcgggtttat attttattgc aaaaggatca gaagaaacgc ttgaccattt    3900
aaataatatt atgactgcat tacagtattc aggtttaggt ggtaaacgta atgcaggata    3960
cggacaattt gaatatgaaa taataaataa tcaacaacta tctaagttac tgaatcaaaa    4020
```

```
tggaaaacat tctattcttt tatcaacggc aatggctaaa aaagaagaga tagagagtgc   4080
tttaaaagag gcgagataca ttttaactaa acgttctggt ttcgtacaat caacgaatta   4140
ttctgaaatg ctagttaaaa aaagtgattt ctatagcttt tcttcgggtt cagtttttaa   4200
aaatatcttt aatggtgata tttttaatgt tggccataat ggtaaacacc cagtctatcg   4260
ctatgcaaaa cctttatggt tggaggtata agtatgacaa taaaaaatta tgaagtcgtt   4320
attaaaactt taggtccaat tcatattggt agtggtcaag ttatgaagaa gcaagattac   4380
atttatgact tttataattc taaagtttat atgattaatg gaaataaact agttaaattt   4440
ttaaaaagaa aaaatttact ttatacatat caaaacttt tgaggtaccc accaaaaaat    4500
ccaagagaaa atggacttaa agactattta gacgctcaaa atgttaagca aagtgaatgg   4560
gaagcatttg tgagttattc tgaaaaggtc aatcaaggta agaaatatgg taacacacgt   4620
cctaaaccgc taaatgattt acacttaatg gtaagagacg gtcaaaataa agtgtatctt   4680
ccaggtagtt caatcaaagg tgctatcaaa acaactctcg tgtcaaaata taataatgaa   4740
aaaaacaaag acatttatag caaaattaaa gtcagcgatt caaaacctat tgatgaaagt   4800
aatttagcga tttatcaaaa aatagacatt aataaaagtg aaaaatcaat gcctttatat   4860
agagagtgca tagatgtaaa taccgaaata aaatttaagt taacaattga agatgaaatt   4920
tattctatta tgaaattga acaaagtatc caagatttt acaaaaacta ttatgataaa     4980
tggttagtcg gattcaaaga aacaaaaggt ggaagacgat ttgcattaga gggcggtata   5040
ccagatgtcc taaatcagaa tattttgttc ttaggtgctg ggacaggatt tgttagtaaa   5100
acaacacact atcaattaaa aaatcgaaaa caagctaaac aagattcttt tgagatttta   5160
actaaaaaat tccgaggaac ttatgggaaa atgaaggaaa taccttctaa cgtaccagtt   5220
gctttaaaag gaacaactaa tcaaagtcgt catacttcat atcagcaagg aatgtgtaaa   5280
gtgagttttc aagagttaaa taatgaggtg ctataatgaa atattatttt agtccaatag   5340
gtaattcaga tccatggaga aatgatagag atggtgcgat gcttcatatc gtgcgtcatt   5400
ataatttaga taaggttgta ttatattta ctagaactat ttgggaagga atgaaaata     5460 gaaaaggcca taaaatttac gaatgggaaa aaattatcca aactgtttct ccaaatactg   5520
aagtagaaat cattattgaa aatgtagaca atgctcaaga ttatgatgtc ttcaaggaga   5580
aatttcataa gtatttaaaa ataattgaag atagctatga agattgtgaa ataatttga    5640 atgtcactag tggtacaccc caaatggaat caacattatg tttagaatat atcgtctatc   5700
ctgaaaataa gaagtgtgta caagtgagca cgccaactaa ggatagtaat gcaggtatcg   5760
aatattcaaa tcctaaagat aaagtagaag aatttgaaat agtcaatgaa gtagaaaaga   5820
aatctgaaaa acgttgtaaa gaaataaaca ttttaagctt tagagaagca atgattagat   5880
ctcaaattct cggtttaata gataattatg attatgaagg tgctcttaat ttagtaagta   5940
atcaaaaatc ttttcgcaat gggaaattat taagaaaaaa actactatca ttaacaaaac   6000
aaattaaaac acatgaagtt tttccagaaa ttaatgagaa gtacagagat gatgctttaa   6060
aaaaatcact atttcattat ttactgttaa atatgagata taatcgtctt gatgtagctg   6120
aaacgttaat tagagtaaaa tctattgctg agtttatact taaaacatac attgagattc   6180
attggcctac tttaataatt gaaaagatg gtaaaccttca tctaaatgat gaagataatt   6240
tatcttttgt ttataaatat aatctgttat tagaaaaaag aaaacaaaat tttgatgtttt  6300 caagaatttt gggacttcct gcattcattg atatactcac aattttagaa cctaattctc   6360
```

-continued

| | |
|---|---|
| aactattaaa agaagtcaat gcagtaaacg atataaatgg tttaagaaat tccatagccc | 6420 |
| ataatttaga tacattaaat ttggataaaa ataaaaatta taagaaaata atgttatctg | 6480 |
| ttgaagcgat aaagaatatg ttacacatct catttcctga gatagaggaa gaagactata | 6540 |
| attattttga agaaaaaaat aaggaattta aagagctatt atgataaata aaattacagt | 6600 |
| agagttagac ttgccagaaa gtattcggtt tcaatattta ggaagtgttt tacatggtgt | 6660 |
| gttaatggat tatctatctg atgatattgc tgaccaatta catcatgaat ttgcttatag | 6720 |
| cccattgaaa caagaatat atcataaaaa taaaaaaatc atttgggaaa ttgtatgtat | 6780 |
| gtcagataat ttatttaaag aggttgttaa actatttagt tctaaaaata gtttgctttt | 6840 |
| gaaatattat caaacaaata ttgacattca atcatttcaa attgagaaga taaatgttca | 6900 |
| gaacatgatg aaccaactgt tacaagtaga agatctaagt cgttatgtac gtcttaatat | 6960 |
| acaaacacct atgtctttta aatatcagaa cagttacatg attttcctg atgttaaacg | 7020 |
| ttttttttaga agtattatga tacaatttga cgcgtttttt gaagaatata gaatgtacga | 7080 |
| caaagaaaca ttaaattttc tagaaaagaa tgttaatatt gttgactaca aattgaaaag | 7140 |
| tacacgtttt aacttggaaa aagttaaaat tccttcattt acaggagaaa tagtatttaa | 7200 |
| aattaaagga cccttacctt ttctacagtt aactcatttt ttattaaagt ttggcgaatt | 7260 |
| ttcaggttca ggtataaaaa caagcttagg tatgggaaaa tatagtataa tttaattaag | 7320 |
| acatagttaa aatttagttg tcaaaa | 7346 |

<210> SEQ ID NO 2
<211> LENGTH: 2274
<212> TYPE: DNA
<213> ORGANISM: Artificial Sequence
<220> FEATURE:
<223> OTHER INFORMATION: Synthetic constructs

<400> SEQUENCE: 2

| | |
|---|---|
| atgaataaaa aaatatatt aatgtatggc tctttattac atgatatagg gaaaattata | 60 |
| tatcgaagtg gtgatcatac attttcaaga ggtacgcatt caaaattagg tcatcaattt | 120 |
| ttgtcccaat tttcagaatt taagacaac gaagtgcttg ataacgttgc ttatcatcat | 180 |
| tacaaagaac tcgcaaaagc taatttagat aatgataata cagcttatat tacctatatt | 240 |
| gcggataata ttgcgagtgg tattgataga agagatatta tagaagaagg cgatgaagaa | 300 |
| tacgaaaaac aactatttaa ttttgataaa tatacaccgc tatatagtgt gtttaatatt | 360 |
| gtgaattctg aaaaattgaa acaaacaaac gggaagttta aatttttctaa tgaaagtaat | 420 |
| attgaatatc ctaaaactga aaacattcaa tattcaagtg gaaattatac aacattaatg | 480 |
| aaagatatga gtcatgattt agagcacaaa ttaagtatta agaaggtac atttccttca | 540 |
| ttattacaat ggacggaaag tctatggcaa tatgtaccta gttcgacaaa taaaaaccaa | 600 |
| ttaattgata tttctctta tgatcatagt cgtattacat gtgccatcgc cagttgtata | 660 |
| tttgattatt taaatgaaaa taacatacat aattacaaag atgaattgtt ctcaaagtat | 720 |
| gaaaatacca atcatttta tcaaaagaa gctttttac tacttagtat ggatatgagt | 780 |
| ggtattcaag atttatttta caatataagc ggttctaaag cattaaagag tctaagatct | 840 |
| cgtagttttt atttagaact catgcttgaa gtaatcgttg atcaattatt agaaagatta | 900 |
| gaattagcac gagcaaatct tttgtataca ggtggtggcc atgcttattt attagtgtct | 960 |
| aatactgata aagtgaagaa aaaaataact caatttaata atgaattaaa aaatggtttt | 1020 |
| atgtcagaat ttactacaga tctttcatta tcaatggctt ttgaaaaatg tagtggcgat | 1080 | gatttaatga atacaagtgg taattataga actatttggc gtaatgttag cagcaaactt    1140 tctgatatta aagcgcataa atattccgcg aagatatat taaaattaaa tcattttcat    1200 tcgtatggag atcgggaatg taaagaatgt ttaagaagtg acatagatat taatgatgat    1260 ggactatgta gtatatgtga aggaattatt aatatatcaa atgatttaag agataaatca    1320 ttctttgtac tgtcagaaac tggaaaatta aaaatgccat tcaataaatt tatatcggtt    1380 attgattatg aagaggcaga aatgttagta caaaataata atcaagttcg tatttacagt    1440 aaaaataaac catatatagg cataggaata tcaacaaatt tatggatgtg tgattacgac    1500 tatgctagtc aaaatcaaga tatgagagaa aaaggtattg gaagttatgt agatagagaa    1560 gaaggggtta agcgtttagg cgtggtacgt gccgatatag ataatctcgg tgctacattt    1620 atatctggaa ttccagaaaa atataattca atttcaagaa cagctacatt gtctcgtcaa    1680 ttatcattat tttttaaata cgaattaaat catttattag aaaattatca aattactgct    1740 atatattcag gcggtgacga tttatttta atcggtgcat gggatgacat tatagaagca    1800 agcatttata taaatgacaa atttaaagag tttactcttg ataaactaac attgtctgcc    1860 ggggttggaa tgtttagtgg taagtaccca gtttctaaaa tggcttttga gacaggacga    1920 cttgaagaag cggctaagac tggtgaaaaa aatcagatat ctctttggtt acaagaaaaa    1980 gtatataact gggatgagtt taaaaagaat atcttagaag aaaaacttct cgttttacaa    2040 cagggggtttt ctcaaacaga tgaacacggg aaagccttca tttataaaat gctcgcttta    2100 ctgagaaata atgaagctat taatattgct cgtttagctt acttattagc aagaagcaag    2160 atgaatgagg atttttacgtc taaaattttt aattgggctc aaaacgacaa agataaaaat    2220 caattaatta cagcgttaga gtattatatt tatcaaataa gggaggctga ttga           2274

<210> SEQ ID NO 3
<211> LENGTH: 426
<212> TYPE: DNA
<213> ORGANISM: Artificial Sequence
<220> FEATURE:
<223> OTHER INFORMATION: Synthetic constructs

<400> SEQUENCE: 3
atgatattag ctaaaactaa aagtggtaaa acgatagatt tgacttttgc acatgaggtc     60
gtaaaaagta atgtaaaaaa tgttaaagat agaaaaggca agaaaaaca agttttattt    120 aacgggctta caacaagcaa gttaagaaat ttaatggagc aggtaaatag actttatact    180 attgcatttta attcgaatga ggatcaattg aatgaagaat tcattgatga attagaatat    240
ttaaaaatta aattttatta tgaagcagga cgagaaaaaa gcgttgatga attttttaaaa    300 aaaacattga tgtttccaat tattgataga gtgataaaaa aagaatcaaa aaaatttttc    360
ttagattatt gtaaatactt tgaagctttta gttgcatacg ctaaatatta tcaaaaggag    420
gattaa                                                                426

<210> SEQ ID NO 4
<211> LENGTH: 645
<212> TYPE: DNA
<213> ORGANISM: Artificial Sequence
<220> FEATURE:
<223> OTHER INFORMATION: Synthetic constructs

<400> SEQUENCE: 4
atgtattcaa aaattaaaat ttcaggaaca attgaagtag ttactggttt acacatcggc     60

| | |
|---|---|
| ggaggcggtg aatctagtat gattggagca attgattctc ctgtagttag agatttgcaa | 120 |
| accaaattac ctatcatacc tggcagttca atcaaaggaa aaatgagaaa tttattagca | 180 |
| aaacattttg gcttgaaaat gaaacaagag agtcataacc aagatgatga acgtgtatta | 240 |
| agattatttg gctcaagtga aaaaggaaat atccaaagag ctcgtctaca aatttctgat | 300 |
| gcattctttt ctgaaaagac aaaagagcat tttgcgcaaa atgatattgc ctatacagaa | 360 |
| acgaaatttg agaatacaat taatcgttta actgcagttg caaacccaag acaaattgaa | 420 |
| agagtaacaa gaggatctga gtttgacttt gtatttattt acaatgtcga tgaagagtcg | 480 |
| caagttgagg atgattttga gaatattgaa aaagcgattc acttattaga gaatgactat | 540 |
| cttggtggcg gcggaactag aggtaacgga cgtattcaat ttaaagatac aaatatcgag | 600 |
| acagttgttg gagaatacga tagtacaaat cttaaaatta agtag | 645 |

<210> SEQ ID NO 5
<211> LENGTH: 915
<212> TYPE: DNA
<213> ORGANISM: Artificial Sequence
<220> FEATURE:
<223> OTHER INFORMATION: Synthetic constructs

<400> SEQUENCE: 5

| | |
|---|---|
| atgacattgg caacaaaagt atttaaactt tctttaaga ctcctgttca ttttggaaaa | 60 |
| aaacggttgt cagatggtga aatgacaatc actgctgata ctttgtttag tgctttattt | 120 |
| attgaaacac ttcaattggg taaagatacc gattggttat taaatgattt aatcattagt | 180 |
| gatacatttc cttatgagaa tgagctttat tatcttccta aacctttgat aaaaattgac | 240 |
| tctaaagaag aagataacca taaagcattt aaaaagttaa aatatgttcc ggttcatcac | 300 |
| tataatcaat atttaaatgg agagttaagc gctgaagatg cgacagattt aaatgatatt | 360 |
| tttaatattg ggtattttc tctacaaaca aaggtttcat taatagcaca agaaactgat | 420 |
| tcaagtgctg atagtgaacc ttattcagtg ggaacattta cttttgaacc tgaagcgggt | 480 |
| ttatatttta ttgcaaaagg atcagaagaa acgcttgacc atttaaataa tattatgact | 540 |
| gcattacagt attcaggttt aggtggtaaa cgtaatgcag gatacggaca atttgaatat | 600 |
| gaaataataa ataatcaaca actatctaag ttactgaatc aaaatggaaa acattctatt | 660 |
| cttttatcaa cggcaatggc taaaaaagaa gagatagaga gtgctttaaa agaggcgaga | 720 |
| tacatttaa ctaaacgttc tggtttcgta caatcaacga attattctga aatgctagtt | 780 |
| aaaaaagtg atttctatag cttttcttcg ggttcagttt ttaaaaatat ctttaatggt | 840 |
| gatatttta atgttggcca taatggtaaa cacccagtct atcgctatgc aaaacccttta | 900 |
| tggttggagg tataa | 915 |

<210> SEQ ID NO 6
<211> LENGTH: 1023
<212> TYPE: DNA
<213> ORGANISM: Artificial Sequence
<220> FEATURE:
<223> OTHER INFORMATION: Synthetic constructs

<400> SEQUENCE: 6

| | |
|---|---|
| atgacaataa aaaattatga agtcgttatt aaaactttag gtccaattca tattggtagt | 60 |
| ggtcaagtta tgaagaagca agattacatt tatgactttt ataattctaa agtttatatg | 120 |
| attaatggaa ataaactagt taaattttta aaaagaaaaa atttacttta tacatatcaa | 180 |
| aacttttga ggtacccacc aaaaaatcca agagaaaatg gacttaaaga ctatttagac | 240 |

```
gctcaaaatg ttaagcaaag tgaatgggaa gcatttgtga gttattctga aaaggtcaat      300
caaggtaaga aatatggtaa cacacgtcct aaaccgctaa atgatttaca cttaatggta      360
agagacggtc aaaataaagt gtatcttcca ggtagttcaa tcaaaggtgc tatcaaaaca      420
actctcgtgt caaaatataa aatgaaaaaa acaaagaca tttatagcaa aattaaagtc       480
agcgattcaa aaccattga tgaaagtaat ttagcgattt atcaaaaaat agacattaat      540
aaaagtgaaa aatcaatgcc tttatataga gagtgcatag atgtaaatac cgaaataaaa      600
tttaagttaa caattgaaga tgaaatttat tctattaatg aaattgaaca agtatccaa       660 gatttttaca aaaactatta tgataaatgg ttagtcggat tcaaagaaac aaaaggtgga      720
agacgatttg cattagaggg cggtataccta gatgtcctaa atcagaatat tttgttctta     780
ggtgctggga caggatttgt tagtaaaaca acacactatc aattaaaaaa tcgaaaacaa      840
gctaaacaag attcttttga gatttttaact aaaaaattcc gaggaactta tgggaaaatg    900
aaggaaatac cttctaacgt accagttgct ttaaaaggaa caactaatca aagtcgtcat      960
acttcatatc agcaaggaat gtgtaaagtg agttttcaag agttaaataa tgaggtgcta    1020
taa                                                                    1023

<210> SEQ ID NO 7
<211> LENGTH: 1269
<212> TYPE: DNA
<213> ORGANISM: Artificial Sequence
<220> FEATURE:
<223> OTHER INFORMATION: Synthetic constructs

<400> SEQUENCE: 7
atgaaaatat tatttagtcc aataggtaat tcagatccat ggagaaatga tagagatggt       60
gcgatgcttc atatcgtgcg tcattataat ttagataagg ttgtattata ttttactaga     120
actatttggg aaggaaatga aaatagaaaa ggccataaaa tttacgaatg ggaaaaaatt      180
atccaaactg tttctccaaa tactgaagta gaaatcatta ttgaaaatgt agacaatgct     240
caagattatg atgtcttcaa ggagaaattt cataagtatt taaaaataat tgaagatagc      300
tatgaagatt gtgaaataat tttgaatgtc actagtggta caccccaaat ggaatcaaca     360
ttatgtttag aatatatcgt ctatcctgaa aataagaagt gtgtacaagt gagcacgcca      420
actaaggata gtaatgcagg tatcgaatat tcaaatccta aagataaagt agaagaattt      480
gaaatagtca atgaagtaga aaagaaatct gaaaaacgtt gtaaagaaat aaacatttta    540
agctttagag aagcaatgat tagatctcaa attctcggtt aatagataaa ttatgattat     600
gaaggtgctc ttaatttagt aagtaatcaa aaatctttttc gcaatgggaa attattaaga    660 aaaaactac tatcattaac aaaacaaatt aaaacacatg aagttttttcc agaaattaat    720 gagaagtaca gagatgatgc tttaaaaaaa tcactatttc attatttact gttaaatatg    780
agatataatc gtcttgatgt agctgaaacg ttaattagag taaatctat tgctgagttt      840 atacttaaaa catacattga gattcattgg cctactttaa taattgaaaa agatggtaaa     900
ccttatctaa atgatgaaga taatttatct tttgtttata aatataatct gttattagaa      960
aaaagaaaac aaaattttga tgtttcaaga attttgggac ttcctgcatt cattgatata    1020
ctcacaattt tagaacctaa ttctcaacta ttaaaagaag tcaatgcagt aaacgatata    1080
aatggtttaa gaaattccat agcccataat ttagatacat aaatttggga taaaaataaa     1140
aattataaga aaataatgtt atctgttgaa gcgataaaga atatgttaca catctcattt    1200
```

```
cctgagatag aggaagaaga ctataattat tttgaagaaa aaaataagga atttaaagag   1260
ctattatga                                                          1269

<210> SEQ ID NO 8
<211> LENGTH: 735
<212> TYPE: DNA
<213> ORGANISM: Artificial Sequence
<220> FEATURE:
<223> OTHER INFORMATION: Synthetic constructs

<400> SEQUENCE: 8
atgataaata aaattacagt agagttagac ttgccagaaa gtattcggtt tcaatattta     60
ggaagtgttt tacatggtgt gttaatggat tatctatctg atgatattgc tgaccaatta   120
catcatgaat ttgcttatag cccattgaaa caaagaatat atcataaaaa taaaaaaatc   180
atttgggaaa ttgtatgtat gtcagataat ttatttaaag aggttgttaa actatttagt   240
tctaaaaata gtttgctttt gaaatattat caaacaaata ttgacattca atcatttcaa   300
attgagaaga taaatgttca gaacatgatg aaccaactgt tacaagtaga agatctaagt   360
cgttatgtac gtcttaatat acaaacacct atgtctttta aatatcagaa cagttacatg   420 attttttcctg atgttaaacg ttttttttaga agtattatga tacaatttga cgcgtttttt   480
gaagaatata gaatgtacga caaagaaaca ttaaattttc tagaaaagaa tgttaatatt   540
gttgactaca aattgaaaag tacacgtttt aacttggaaa aagttaaaat tccttcattt   600
acaggagaaa tagtatttaa aattaaagga cccttacctt ttctacagtt aactcatttt   660
ttattaaagt ttggcgaatt ttcaggttca ggtataaaaa caagcttagg tatgggaaaa   720
tatagtataa tttaa                                                   735

<210> SEQ ID NO 9
<211> LENGTH: 45
<212> TYPE: DNA
<213> ORGANISM: Artificial Sequence
<220> FEATURE:
<223> OTHER INFORMATION: Synthetic constructs

<400> SEQUENCE: 9
ttgttgacaa gcaactaacg tatgccgaag tatataaatc atcag                     45

<210> SEQ ID NO 10
<211> LENGTH: 39
<212> TYPE: DNA
<213> ORGANISM: Artificial Sequence
<220> FEATURE:
<223> OTHER INFORMATION: Synthetic constructs

<400> SEQUENCE: 10
ttattgatta attacaatgt ctcgtcccc ttttcttcg                             39

<210> SEQ ID NO 11
<211> LENGTH: 45
<212> TYPE: DNA
<213> ORGANISM: Artificial Sequence
<220> FEATURE:
<223> OTHER INFORMATION: Synthetic constructs

<400> SEQUENCE: 11
aatgcgtcta atggaatacg tatgccgaag tatataaatc atcag                     45

<210> SEQ ID NO 12
<211> LENGTH: 40
```

<212> TYPE: DNA
<213> ORGANISM: Artificial Sequence
<220> FEATURE:
<223> OTHER INFORMATION: Synthetic constructs

<400> SEQUENCE: 12
taataagaat caatctttgt tctcgtcccc ttttcttcgg                               40

<210> SEQ ID NO 13
<211> LENGTH: 45
<212> TYPE: DNA
<213> ORGANISM: Artificial Sequence
<220> FEATURE:
<223> OTHER INFORMATION: Synthetic constructs

<400> SEQUENCE: 13
tacaagacag tatgcagacg tatgccgaag tatataaatc atcag                         45

<210> SEQ ID NO 14
<211> LENGTH: 39
<212> TYPE: DNA
<213> ORGANISM: Artificial Sequence
<220> FEATURE:
<223> OTHER INFORMATION: Synthetic constructs

<400> SEQUENCE: 14 atttttgag aaattcttgt tctcgtcccc ttttcttcg                                 39

<210> SEQ ID NO 15
<211> LENGTH: 45
<212> TYPE: DNA
<213> ORGANISM: Artificial Sequence
<220> FEATURE:
<223> OTHER INFORMATION: Synthetic constructs

<400> SEQUENCE: 15
aataagaatc aatctttacg tatgccgaag tatataaatc atcag                         45

<210> SEQ ID NO 16
<211> LENGTH: 39
<212> TYPE: DNA
<213> ORGANISM: Artificial Sequence
<220> FEATURE:
<223> OTHER INFORMATION: Synthetic constructs

<400> SEQUENCE: 16
aaatgcgtct aatggaatgt tctcgtcccc ttttcttcg                                39

<210> SEQ ID NO 17
<211> LENGTH: 45
<212> TYPE: DNA
<213> ORGANISM: Artificial Sequence
<220> FEATURE:
<223> OTHER INFORMATION: Synthetic constructs

<400> SEQUENCE: 17
aattctcttg atttattacg tatgccgaag tatataaatc atcag                         45

<210> SEQ ID NO 18
<211> LENGTH: 39
<212> TYPE: DNA
<213> ORGANISM: Artificial Sequence
<220> FEATURE:
<223> OTHER INFORMATION: Synthetic constructs

<400> SEQUENCE: 18
aaatgcaaat atgagtatgt tctcgtcccc ttttcttcg        39

<210> SEQ ID NO 19
<211> LENGTH: 45
<212> TYPE: DNA
<213> ORGANISM: Artificial Sequence
<220> FEATURE:
<223> OTHER INFORMATION: Synthetic constructs

<400> SEQUENCE: 19
cttctgcact ttcaattacg tatgccgaag tatataaatc atcag        45

<210> SEQ ID NO 20
<211> LENGTH: 39
<212> TYPE: DNA
<213> ORGANISM: Artificial Sequence
<220> FEATURE:
<223> OTHER INFORMATION: Synthetic constructs

<400> SEQUENCE: 20
atgttgtaac tgaacctggt tctcgtcccc ttttcttcg        39

<210> SEQ ID NO 21
<211> LENGTH: 25
<212> TYPE: DNA
<213> ORGANISM: Artificial Sequence
<220> FEATURE:
<223> OTHER INFORMATION: Synthetic constructs

<400> SEQUENCE: 21
ggatccgagc tcggtaccaa gcttc        25

<210> SEQ ID NO 22
<211> LENGTH: 55
<212> TYPE: DNA
<213> ORGANISM: Artificial Sequence
<220> FEATURE:
<223> OTHER INFORMATION: Synthetic constructs

<400> SEQUENCE: 22
caggatacta aagtaggttg gtacctagct gttagttctc gtccccttttt cttcg        55

<210> SEQ ID NO 23
<211> LENGTH: 55
<212> TYPE: DNA
<213> ORGANISM: Artificial Sequence
<220> FEATURE:
<223> OTHER INFORMATION: Synthetic constructs

<400> SEQUENCE: 23
ataaacgttt agatgcttat gcaaaaggaa cagtgttctc gtccccttttt cttcg        55

<210> SEQ ID NO 24
<211> LENGTH: 55
<212> TYPE: DNA
<213> ORGANISM: Artificial Sequence
<220> FEATURE:
<223> OTHER INFORMATION: Synthetic constructs

<400> SEQUENCE: 24
ttaaagagtt gaaaggagag aaatagcatg aatagttctc gtccccttttt cttcg        55

<210> SEQ ID NO 25
<211> LENGTH: 40
<212> TYPE: DNA
<213> ORGANISM: Artificial Sequence

```
<220> FEATURE:
<223> OTHER INFORMATION: Synthetic constructs

<400> SEQUENCE: 25
accaagcttc tgagggata atattatgtt ttttagtggc                              40

<210> SEQ ID NO 26
<211> LENGTH: 40
<212> TYPE: DNA
<213> ORGANISM: Artificial Sequence
<220> FEATURE:
<223> OTHER INFORMATION: Synthetic constructs

<400> SEQUENCE: 26
cctaaaaacc tacattatgg attcaccta taattacacg                              40

<210> SEQ ID NO 27
<211> LENGTH: 43
<212> TYPE: DNA
<213> ORGANISM: Artificial Sequence
<220> FEATURE:
<223> OTHER INFORMATION: Synthetic constructs

<400> SEQUENCE: 27
tccataatgt aggttttag gcataaaact atatgattta ccc                          43

<210> SEQ ID NO 28
<211> LENGTH: 30
<212> TYPE: DNA
<213> ORGANISM: Artificial Sequence
<220> FEATURE:
<223> OTHER INFORMATION: Synthetic constructs

<400> SEQUENCE: 28
tattatcccc tcagaagctt ggtaccgagc                                        30

<210> SEQ ID NO 29
<211> LENGTH: 23
<212> TYPE: DNA
<213> ORGANISM: Artificial Sequence
<220> FEATURE:
<223> OTHER INFORMATION: Synthetic constructs

<400> SEQUENCE: 29
aaaggcatct agtggtatac ctg                                               23

<210> SEQ ID NO 30
<211> LENGTH: 37
<212> TYPE: DNA
<213> ORGANISM: Artificial Sequence
<220> FEATURE:
<223> OTHER INFORMATION: Synthetic constructs

<400> SEQUENCE: 30
aacaaaaacc aatcatttga aaattttatt aaaaatg                                37

<210> SEQ ID NO 31
<211> LENGTH: 60
<212> TYPE: DNA
<213> ORGANISM: Artificial Sequence
<220> FEATURE:
<223> OTHER INFORMATION: Synthetic constructs

<400> SEQUENCE: 31
cggccaaata ccatccaacc tttgtgtctt gaatactctc aaaatctta aagttttcag        60
```

<210> SEQ ID NO 32
<211> LENGTH: 56
<212> TYPE: DNA
<213> ORGANISM: Artificial Sequence
<220> FEATURE:
<223> OTHER INFORMATION: Synthetic constructs

<400> SEQUENCE: 32
ccaagcttct gtagataaaa ctaaaaatac tattaaaaaa tgttatgaga aaaacg      56

<210> SEQ ID NO 33
<211> LENGTH: 60
<212> TYPE: DNA
<213> ORGANISM: Artificial Sequence
<220> FEATURE:
<223> OTHER INFORMATION: Synthetic constructs

<400> SEQUENCE: 33
cacaaaggtt ggatggtatt tggccgtaac ccaagaagtt aaagaatctt taagattatc  60

<210> SEQ ID NO 34
<211> LENGTH: 40
<212> TYPE: DNA
<213> ORGANISM: Artificial Sequence
<220> FEATURE:
<223> OTHER INFORMATION: Synthetic constructs

<400> SEQUENCE: 34
gcctaaaaac ctaaaagtta cctccgtcaa tatcattaac                        40

<210> SEQ ID NO 35
<211> LENGTH: 48
<212> TYPE: DNA
<213> ORGANISM: Artificial Sequence
<220> FEATURE:
<223> OTHER INFORMATION: Synthetic constructs

<400> SEQUENCE: 35
gacggaggta actttttaggt ttttaggcat aaaactatat gatttacc              48

<210> SEQ ID NO 36
<211> LENGTH: 38
<212> TYPE: DNA
<213> ORGANISM: Artificial Sequence
<220> FEATURE:
<223> OTHER INFORMATION: Synthetic constructs

<400> SEQUENCE: 36 gtattttag ttttatctac agaagcttgg taccgagc                           38

<210> SEQ ID NO 37
<211> LENGTH: 33
<212> TYPE: DNA
<213> ORGANISM: Artificial Sequence
<220> FEATURE:
<223> OTHER INFORMATION: Synthetic constructs

<400> SEQUENCE: 37
accaagcttc tgaaatgcgc caacatcact ttc                               33

<210> SEQ ID NO 38
<211> LENGTH: 48
<212> TYPE: DNA
<213> ORGANISM: Artificial Sequence
<220> FEATURE:
<223> OTHER INFORMATION: Synthetic constructs

<400> SEQUENCE: 38
gcctaaaaac ctattataat ttacttgaac cattaaagtc tctaacac         48

<210> SEQ ID NO 39
<211> LENGTH: 45
<212> TYPE: DNA
<213> ORGANISM: Artificial Sequence
<220> FEATURE:
<223> OTHER INFORMATION: Synthetic constructs

<400> SEQUENCE: 39
gtaaattata ataggttttt aggcataaaa ctatatgatt taccc            45

<210> SEQ ID NO 40
<211> LENGTH: 30
<212> TYPE: DNA
<213> ORGANISM: Artificial Sequence
<220> FEATURE:
<223> OTHER INFORMATION: Synthetic constructs

<400> SEQUENCE: 40
ttggcgcatt tcagaagctt ggtaccgagc                             30

<210> SEQ ID NO 41
<211> LENGTH: 43
<212> TYPE: DNA
<213> ORGANISM: Artificial Sequence
<220> FEATURE:
<223> OTHER INFORMATION: Synthetic constructs

<400> SEQUENCE: 41
caagcttctg ttttgacggg taaatagata ttgttttttg ttc              43

<210> SEQ ID NO 42
<211> LENGTH: 50
<212> TYPE: DNA
<213> ORGANISM: Artificial Sequence
<220> FEATURE:
<223> OTHER INFORMATION: Synthetic constructs

<400> SEQUENCE: 42
cctaaaaacc taggatatag aaaatcatgt cattaaaaaa atgtatgtac        50

<210> SEQ ID NO 43
<211> LENGTH: 45
<212> TYPE: DNA
<213> ORGANISM: Artificial Sequence
<220> FEATURE:
<223> OTHER INFORMATION: Synthetic constructs

<400> SEQUENCE: 43
tttctatatc ctaggttttt aggcataaaa ctatatgatt taccc             45

<210> SEQ ID NO 44
<211> LENGTH: 29
<212> TYPE: DNA
<213> ORGANISM: Artificial Sequence
<220> FEATURE:
<223> OTHER INFORMATION: Synthetic constructs

<400> SEQUENCE: 44
cccgtcaaaa cagaagcttg gtaccgagc                              29

<210> SEQ ID NO 45

```
<211> LENGTH: 85
<212> TYPE: DNA
<213> ORGANISM: Artificial Sequence
<220> FEATURE:
<223> OTHER INFORMATION: Synthetic constructs

<400> SEQUENCE: 45
aaaggcatct agtggtatac ctgcactggc aattttaatt gtgttatctt cttaggtttt    60
taggcataaa actatatgat ttacc                                          85

<210> SEQ ID NO 46
<211> LENGTH: 70
<212> TYPE: DNA
<213> ORGANISM: Artificial Sequence
<220> FEATURE:
<223> OTHER INFORMATION: Synthetic constructs

<400> SEQUENCE: 46
aacaaaaacc aatcatttga aaattttatt aaaaatgatt ttcaccataa acagaagctt    60
ggtaccgagc                                                           70

<210> SEQ ID NO 47
<211> LENGTH: 35
<212> TYPE: DNA
<213> ORGANISM: Artificial Sequence
<220> FEATURE:
<223> OTHER INFORMATION: Synthetic constructs

<400> SEQUENCE: 47
accaagcttc tgccgcatat gaaaaaaatg agggc                               35

<210> SEQ ID NO 48
<211> LENGTH: 41
<212> TYPE: DNA
<213> ORGANISM: Artificial Sequence
<220> FEATURE:
<223> OTHER INFORMATION: Synthetic constructs

<400> SEQUENCE: 48
gcctaaaaac ctaaattagg tttactactg aatccatagc c                        41

<210> SEQ ID NO 49
<211> LENGTH: 44
<212> TYPE: DNA
<213> ORGANISM: Artificial Sequence
<220> FEATURE:
<223> OTHER INFORMATION: Synthetic constructs

<400> SEQUENCE: 49
aaacctaatt taggttttta ggcataaaac tatatgattt accc                     44

<210> SEQ ID NO 50
<211> LENGTH: 27
<212> TYPE: DNA
<213> ORGANISM: Artificial Sequence
<220> FEATURE:
<223> OTHER INFORMATION: Synthetic constructs

<400> SEQUENCE: 50
atatgcggca gaagcttggt accgagc                                        27

<210> SEQ ID NO 51
<211> LENGTH: 34
<212> TYPE: DNA
<213> ORGANISM: Artificial Sequence
```

```
<220> FEATURE:
<223> OTHER INFORMATION: Synthetic constructs

<400> SEQUENCE: 51
agttgcagga tagcatgcaa tgggatttgc actc                                34

<210> SEQ ID NO 52
<211> LENGTH: 31
<212> TYPE: DNA
<213> ORGANISM: Artificial Sequence
<220> FEATURE:
<223> OTHER INFORMATION: Synthetic constructs

<400> SEQUENCE: 52
tcttaaggaa ctcctcaaag gcacgtgcca c                                   31

<210> SEQ ID NO 53
<211> LENGTH: 26
<212> TYPE: DNA
<213> ORGANISM: Artificial Sequence
<220> FEATURE:
<223> OTHER INFORMATION: Synthetic constructs

<400> SEQUENCE: 53
acctaattac ctacaagcga tgttac                                         26

<210> SEQ ID NO 54
<211> LENGTH: 22
<212> TYPE: DNA
<213> ORGANISM: Artificial Sequence
<220> FEATURE:
<223> OTHER INFORMATION: Synthetic constructs

<400> SEQUENCE: 54
cgtgatgagg acggtttttt ag                                             22

<210> SEQ ID NO 55
<211> LENGTH: 36
<212> TYPE: DNA
<213> ORGANISM: Artificial Sequence
<220> FEATURE:
<223> OTHER INFORMATION: Synthetic constructs

<400> SEQUENCE: 55
ttgtcaaaaa aagtgacata tcatataatc ttgtac                              36

<210> SEQ ID NO 56
<211> LENGTH: 30
<212> TYPE: DNA
<213> ORGANISM: Artificial Sequence
<220> FEATURE:
<223> OTHER INFORMATION: Synthetic constructs

<400> SEQUENCE: 56 actgtactttt tacagtcgg ttttctaatg                                     30

<210> SEQ ID NO 57
<211> LENGTH: 41
<212> TYPE: DNA
<213> ORGANISM: Artificial Sequence
<220> FEATURE:
<223> OTHER INFORMATION: Synthetic constructs

<400> SEQUENCE: 57
cccctagaaa ttaatcaatg cgtattttat tcaaaatcta c                        41
```

<210> SEQ ID NO 58
<211> LENGTH: 42
<212> TYPE: DNA
<213> ORGANISM: Artificial Sequence
<220> FEATURE:
<223> OTHER INFORMATION: Synthetic constructs

<400> SEQUENCE: 58
gattttgaat aaaatacgca ttgattaatt tctagggat gg                42

<210> SEQ ID NO 59
<211> LENGTH: 33
<212> TYPE: DNA
<213> ORGANISM: Artificial Sequence
<220> FEATURE:
<223> OTHER INFORMATION: Synthetic constructs

<400> SEQUENCE: 59
gcaccgagat tatctatatc ggcacgtacc acg                         33

<210> SEQ ID NO 60
<211> LENGTH: 33
<212> TYPE: DNA
<213> ORGANISM: Artificial Sequence
<220> FEATURE:
<223> OTHER INFORMATION: Synthetic constructs

<400> SEQUENCE: 60
ggtacgtgcc gatatagata atctcggtgc tac                         33

<210> SEQ ID NO 61
<211> LENGTH: 56
<212> TYPE: DNA
<213> ORGANISM: Artificial Sequence
<220> FEATURE:
<223> OTHER INFORMATION: Synthetic constructs

<400> SEQUENCE: 61
ccaagcttct gtagataaaa ctaaaaatac tattaaaaaa tgttatgaga aaacg  56

<210> SEQ ID NO 62
<211> LENGTH: 40
<212> TYPE: DNA
<213> ORGANISM: Artificial Sequence
<220> FEATURE:
<223> OTHER INFORMATION: Synthetic constructs

<400> SEQUENCE: 62
gcctaaaaac ctaaaagtta cctccgtcaa tatcattaac                  40

<210> SEQ ID NO 63
<211> LENGTH: 45
<212> TYPE: DNA
<213> ORGANISM: Artificial Sequence
<220> FEATURE:
<223> OTHER INFORMATION: Synthetic constructs

<400> SEQUENCE: 63
aatttaacct ttcatttctt tttatatttc gaataaaaat tagac            45

<210> SEQ ID NO 64
<211> LENGTH: 49
<212> TYPE: DNA
<213> ORGANISM: Artificial Sequence
<220> FEATURE:
<223> OTHER INFORMATION: Synthetic constructs

<400> SEQUENCE: 64
ctttagtatc ctgtaaatct aacaacactc taaaaaattg tagattttg          49

<210> SEQ ID NO 65
<211> LENGTH: 42
<212> TYPE: DNA
<213> ORGANISM: Artificial Sequence
<220> FEATURE:
<223> OTHER INFORMATION: Synthetic constructs

<400> SEQUENCE: 65
gagtgttgtt agatttacag gatactaaag taggttggta cc                 42

<210> SEQ ID NO 66
<211> LENGTH: 51
<212> TYPE: DNA
<213> ORGANISM: Artificial Sequence
<220> FEATURE:
<223> OTHER INFORMATION: Synthetic constructs

<400> SEQUENCE: 66
cgaaatataa aagaaatga aaggttaaat taatattaat tttattaaat g         51

<210> SEQ ID NO 67
<211> LENGTH: 44
<212> TYPE: DNA
<213> ORGANISM: Artificial Sequence
<220> FEATURE:
<223> OTHER INFORMATION: Synthetic constructs

<400> SEQUENCE: 67
cagtagtaga actagagtaa aggtgatttg tcactatttt tgac              44

<210> SEQ ID NO 68
<211> LENGTH: 55
<212> TYPE: DNA
<213> ORGANISM: Artificial Sequence
<220> FEATURE:
<223> OTHER INFORMATION: Synthetic constructs

<400> SEQUENCE: 68
gacaaatcac ctttactcta gttctactac tgtttcattt aatttattct ctaac   55

<210> SEQ ID NO 69
<211> LENGTH: 45
<212> TYPE: DNA
<213> ORGANISM: Artificial Sequence
<220> FEATURE:
<223> OTHER INFORMATION: Synthetic constructs

<400> SEQUENCE: 69
gcgtctatac catcctgatt atactaaacc tttagaaata aaatg              45

<210> SEQ ID NO 70
<211> LENGTH: 52
<212> TYPE: DNA
<213> ORGANISM: Artificial Sequence
<220> FEATURE:
<223> OTHER INFORMATION: Synthetic constructs

<400> SEQUENCE: 70
gtttagtata atcaggatgg tatagacgct aaatgtcaca ttttttgaca ac      52

<210> SEQ ID NO 71

```
<211> LENGTH: 30
<212> TYPE: DNA
<213> ORGANISM: Artificial Sequence
<220> FEATURE:
<223> OTHER INFORMATION: Synthetic constructs

<400> SEQUENCE: 71
tttagttgtc aaaaaatgtg acatttagcg                                    30

<210> SEQ ID NO 72
<211> LENGTH: 52
<212> TYPE: DNA
<213> ORGANISM: Artificial Sequence
<220> FEATURE:
<223> OTHER INFORMATION: Synthetic constructs

<400> SEQUENCE: 72
gtatttttag ttttatctag aacaagaaaa aagagaaatt aatcacaaaa tg           52

<210> SEQ ID NO 73
<211> LENGTH: 22
<212> TYPE: DNA
<213> ORGANISM: Artificial Sequence
<220> FEATURE:
<223> OTHER INFORMATION: Synthetic constructs

<400> SEQUENCE: 73
aataatgtat ttacgctggg gc                                            22

<210> SEQ ID NO 74
<211> LENGTH: 41
<212> TYPE: DNA
<213> ORGANISM: Artificial Sequence
<220> FEATURE:
<223> OTHER INFORMATION: Synthetic constructs

<400> SEQUENCE: 74
cccctagaaa ttaatcaatg cgtattttat tcaaaatcta c                       41

<210> SEQ ID NO 75
<211> LENGTH: 38
<212> TYPE: DNA
<213> ORGANISM: Artificial Sequence
<220> FEATURE:
<223> OTHER INFORMATION: Synthetic constructs

<400> SEQUENCE: 75
ggtattccat tagacgcatt taataagaat caatcttt                           38

<210> SEQ ID NO 76
<211> LENGTH: 38
<212> TYPE: DNA
<213> ORGANISM: Artificial Sequence
<220> FEATURE:
<223> OTHER INFORMATION: Synthetic constructs

<400> SEQUENCE: 76
ggtataccac tagatgcctt taacaaaaac caatcatt                           38

<210> SEQ ID NO 77
<211> LENGTH: 34
<212> TYPE: DNA
<213> ORGANISM: Artificial Sequence
<220> FEATURE:
<223> OTHER INFORMATION: Synthetic constructs

<400> SEQUENCE: 77
```

-continued

| | |
|---|---|
| caggatacta aagtaggttg gtacctagct gtta | 34 |

<210> SEQ ID NO 78
<211> LENGTH: 34
<212> TYPE: DNA
<213> ORGANISM: Artificial Sequence
<220> FEATURE:
<223> OTHER INFORMATION: Synthetic constructs

<400> SEQUENCE: 78

| | |
|---|---|
| caagacacaa aggttggatg gtatttggcc gtaa | 34 |

<210> SEQ ID NO 79
<211> LENGTH: 34
<212> TYPE: DNA
<213> ORGANISM: Artificial Sequence
<220> FEATURE:
<223> OTHER INFORMATION: Synthetic constructs

<400> SEQUENCE: 79

| | |
|---|---|
| aagaatttct caaaaaatta caagacagta tgca | 34 |

<210> SEQ ID NO 80
<211> LENGTH: 34
<212> TYPE: DNA
<213> ORGANISM: Artificial Sequence
<220> FEATURE:
<223> OTHER INFORMATION: Synthetic constructs

<400> SEQUENCE: 80

| | |
|---|---|
| aggagttcct taagaagttg caggatagca tgca | 34 |

<210> SEQ ID NO 81
<211> LENGTH: 1025
<212> TYPE: DNA
<213> ORGANISM: Artificial Sequence
<220> FEATURE:
<223> OTHER INFORMATION: Synthetic constructs

<400> SEQUENCE: 81

| | |
|---|---|
| agggataat attatgtttt ttagtggcat taagtaaaaa ttatgctata atataagtat | 60 |
| gctagaacat tctagtaaat aaaacataaa acataatccg tatggcaaac gtcacttgtc | 120 |
| actataccctc gtaaaatga cgctactatc atgtagcgtc attttttata tcttgatgaa | 180 |
| ccatatataa tatgttaaga tcacatttat ttttaatttc aaattgataa ggaaatagat | 240 |
| cactaaatga aaatgcgcca acatcacttt caatatataa tatatcatcg tcattcacat | 300 |
| catcatattc acgtcttgct tgttttaata catcttcttt tctatcctct aattctttag | 360 |
| tgaaataata atcataaggc gtaccctttt caatatatgt ttttgacggg taaatagata | 420 |
| ttgttttttg ttcgttataa atagatttgt tgttatatac aattgcttta tggtgaaaat | 480 |
| catttttaat aaaattttca aaagattgat tcttattaaa tgcgtctaat ggaataccctg | 540 |
| cactggcaat tttaattgtg ttatcttctt tttggtaggc gtacttttta tgattgagta | 600 |
| catacatttt tttaatgaca tgattttcta tatcccactt acctaatgca atagggtcaa | 660 |
| ataattcatc atttatttta tgtttaattt ttgattttaa atataaactg tcagtatcac | 720 |
| aatatataaa gcagtcatct atttcagatt gtgttagaga ctttaatggt tcaagtaaat | 780 |
| tataaagggc ttgtgatgtg acaaaagtag aaaacaataa attacgttca ctgttttttat | 840 |
| atccattttc atggttaact aaaaaaccgt cctcatcacg tctaaacaaa ttaaaatgtg | 900 |

```
accgtaaagc aggtatacca tacagaccat ttaaaacaac tttacttaac atgatttctt    960
cttgtgaata agtatgtgta ttgacttcat cagtgatcgt gtaattatag ggtgaatcca   1020
taatg                                                               1025
```

<210> SEQ ID NO 82
<211> LENGTH: 1025
<212> TYPE: DNA
<213> ORGANISM: Artificial Sequence
<220> FEATURE:
<223> OTHER INFORMATION: Synthetic constructs

<400> SEQUENCE: 82

```
aggggataat attatgtttt ttagtggcat aaaataaaaa ttatgctata atataagtat     60
gctagaacat tctagtaaat aaaacataaa acataatccg tatggcaaac gtcacttgtc    120
actatacctc gtaaaaatga cgctactatc atgtagcgtc atttttttata tcttgatgaa   180 ccatatataa tatgttaaga tcacatttat ttttaatttc aaattgataa ggaaatagat    240
cactaaatga aaatgcgcca acatcacttt caatatataa tatatcatcg tcatttacgt    300
cgtcatattc acgtcttgct tgttttaata catcttcttt tctatcctct aattctttag    360
tgaaataata atcataaggc gtaccctttt caatgtaagt ctttgacggg taaatagata    420
ttgttttttg ttcgttataa atagatttgt tgttatatac aattgcttta tggtgaaaat    480 cattttaat aaaattttca atgattggt ttttgttaaa ggcatctagt ggtatacctg      540
cactggcaat tttaattgtg ttatcttctt tttggtaggc gtacttttta tgattgagta    600
catacatttt tttaatgaca tgattttcta tgtcccattt acctaatgca atagggtcaa    660
ataattcatc atttatttta tgtttaattt ttgattttaa atataaactg tcagtatcac    720
aatatataaa acaatcgtct atttcagatt gtgttagaga ctttaatggt tcaagtaaat    780
tataaagggc ttgtgatgtg acaaaagtag aaaacaataa attacgttca ctgttttttat   840 atccattttc atggttaact aaaaaaaccgt cctcatcacg tctaaacaaa ttaaaatgtg    900
accgtaaagc aggtatacca tacagaccat tcaagacgac tttacttaac atgatttctt    960
cttgtgaata agtatgtgta ttgacttcat cagtgatcgt gtaattatag ggtgaatcca   1020
taatg                                                               1025
```

<210> SEQ ID NO 83
<211> LENGTH: 35
<212> TYPE: DNA
<213> ORGANISM: Artificial Sequence
<220> FEATURE:
<223> OTHER INFORMATION: Synthetic constructs

<400> SEQUENCE: 83

```
acgtatgccg aagtatataa atcatcagta caaag                                35
```

<210> SEQ ID NO 84
<211> LENGTH: 35
<212> TYPE: RNA
<213> ORGANISM: Artificial Sequence
<220> FEATURE:
<223> OTHER INFORMATION: Synthetic constructs

<400> SEQUENCE: 84

```
acguaugccg aaguauauaa aucaucagua caaag                                35
```

<210> SEQ ID NO 85
<211> LENGTH: 35

```
<212> TYPE: DNA
<213> ORGANISM: Artificial Sequence
<220> FEATURE:
<223> OTHER INFORMATION: Synthetic constructs

<400> SEQUENCE: 85
ctttgtactg atgatttata tacttcggca tacgt                                35

<210> SEQ ID NO 86
<211> LENGTH: 35
<212> TYPE: DNA
<213> ORGANISM: Artificial Sequence
<220> FEATURE:
<223> OTHER INFORMATION: Synthetic constructs

<400> SEQUENCE: 86
attgtaatta atcaataatt gttgacaagc aacta                                35

<210> SEQ ID NO 87
<211> LENGTH: 35
<212> TYPE: RNA
<213> ORGANISM: Artificial Sequence
<220> FEATURE:
<223> OTHER INFORMATION: Synthetic constructs

<400> SEQUENCE: 87
auuguaauua aucauaauu guugacaagc aacua                                 35

<210> SEQ ID NO 88
<211> LENGTH: 35
<212> TYPE: DNA
<213> ORGANISM: Artificial Sequence
<220> FEATURE:
<223> OTHER INFORMATION: Synthetic constructs

<400> SEQUENCE: 88
tagttgcttg tcaacaatta ttgattaatt acaat                                35

<210> SEQ ID NO 89
<211> LENGTH: 35
<212> TYPE: DNA
<213> ORGANISM: Artificial Sequence
<220> FEATURE:
<223> OTHER INFORMATION: Synthetic constructs

<400> SEQUENCE: 89
aaagattgat tcttattaaa tgcgtctaat ggaat                                35

<210> SEQ ID NO 90
<211> LENGTH: 35
<212> TYPE: RNA
<213> ORGANISM: Artificial Sequence
<220> FEATURE:
<223> OTHER INFORMATION: Synthetic constructs

<400> SEQUENCE: 90
aaagauugau ucuuauuaaa ugcgucuaau ggaau                                35

<210> SEQ ID NO 91
<211> LENGTH: 35
<212> TYPE: DNA
<213> ORGANISM: Artificial Sequence
<220> FEATURE:
<223> OTHER INFORMATION: Synthetic constructs

<400> SEQUENCE: 91
```

-continued attccattag acgcatttaa taagaatcaa tcttt                35

<210> SEQ ID NO 92
<211> LENGTH: 35
<212> TYPE: DNA
<213> ORGANISM: Artificial Sequence
<220> FEATURE:
<223> OTHER INFORMATION: Synthetic constructs

<400> SEQUENCE: 92
aagaatttct caaaaaatta caagacagta tgcag                35

<210> SEQ ID NO 93
<211> LENGTH: 35
<212> TYPE: RNA
<213> ORGANISM: Artificial Sequence
<220> FEATURE:
<223> OTHER INFORMATION: Synthetic constructs

<400> SEQUENCE: 93
aagaauuucu caaaaaauua caagacagua ugcag                35

<210> SEQ ID NO 94
<211> LENGTH: 35
<212> TYPE: DNA
<213> ORGANISM: Artificial Sequence
<220> FEATURE:
<223> OTHER INFORMATION: Synthetic constructs

<400> SEQUENCE: 94
ctgcatactg tcttgtaatt ttttgagaaa ttctt                35

<210> SEQ ID NO 95
<211> LENGTH: 35
<212> TYPE: DNA
<213> ORGANISM: Artificial Sequence
<220> FEATURE:
<223> OTHER INFORMATION: Synthetic constructs

<400> SEQUENCE: 95
attccattag acgcatttaa taagaatcaa tcttt                35

<210> SEQ ID NO 96
<211> LENGTH: 35
<212> TYPE: RNA
<213> ORGANISM: Artificial Sequence
<220> FEATURE:
<223> OTHER INFORMATION: Synthetic constructs

<400> SEQUENCE: 96
auuccauuag acgcauuuaa uaagaaucaa ucuuu                35

<210> SEQ ID NO 97
<211> LENGTH: 35
<212> TYPE: DNA
<213> ORGANISM: Artificial Sequence
<220> FEATURE:
<223> OTHER INFORMATION: Synthetic constructs

<400> SEQUENCE: 97
aaagattgat tcttattaaa tgcgtctaat ggaat                35

<210> SEQ ID NO 98
<211> LENGTH: 35
<212> TYPE: DNA
<213> ORGANISM: Artificial Sequence

```
<220> FEATURE:
<223> OTHER INFORMATION: Synthetic constructs

<400> SEQUENCE: 98
atactcatat ttgcatttaa ttctcttgat ttatt                                35

<210> SEQ ID NO 99
<211> LENGTH: 35
<212> TYPE: RNA
<213> ORGANISM: Artificial Sequence
<220> FEATURE:
<223> OTHER INFORMATION: Synthetic constructs

<400> SEQUENCE: 99
auacucauau uugcauuuaa uucucuugau uuauu                                35

<210> SEQ ID NO 100
<211> LENGTH: 35
<212> TYPE: DNA
<213> ORGANISM: Artificial Sequence
<220> FEATURE:
<223> OTHER INFORMATION: Synthetic constructs

<400> SEQUENCE: 100
aataaatcaa gagaattaaa tgcaaatatg agtat                                35

<210> SEQ ID NO 101
<211> LENGTH: 35
<212> TYPE: DNA
<213> ORGANISM: Artificial Sequence
<220> FEATURE:
<223> OTHER INFORMATION: Synthetic constructs

<400> SEQUENCE: 101
caggttcagt tacaacatct tctgcactttt caatt                               35

<210> SEQ ID NO 102
<211> LENGTH: 35
<212> TYPE: RNA
<213> ORGANISM: Artificial Sequence
<220> FEATURE:
<223> OTHER INFORMATION: Synthetic constructs

<400> SEQUENCE: 102
cagguucagu uacaacaucu ucugcacuuu caauu                                35

<210> SEQ ID NO 103
<211> LENGTH: 35
<212> TYPE: DNA
<213> ORGANISM: Artificial Sequence
<220> FEATURE:
<223> OTHER INFORMATION: Synthetic constructs

<400> SEQUENCE: 103
aattgaaagt gcagaagatg ttgtaactga acctg                                35

<210> SEQ ID NO 104
<211> LENGTH: 34
<212> TYPE: DNA
<213> ORGANISM: Artificial Sequence
<220> FEATURE:
<223> OTHER INFORMATION: Synthetic constructs

<400> SEQUENCE: 104
taacagctag gtaccaacct actttagtat cctg                                 34
```

<210> SEQ ID NO 105
<211> LENGTH: 34
<212> TYPE: RNA
<213> ORGANISM: Artificial Sequence
<220> FEATURE:
<223> OTHER INFORMATION: Synthetic constructs

<400> SEQUENCE: 105
uaacagcuag guaccaaccu acuuuaguau ccug                                34

<210> SEQ ID NO 106
<211> LENGTH: 34
<212> TYPE: DNA
<213> ORGANISM: Artificial Sequence
<220> FEATURE:
<223> OTHER INFORMATION: Synthetic constructs

<400> SEQUENCE: 106
caggatacta aagtaggttg gtacctagct gtta                                34

<210> SEQ ID NO 107
<211> LENGTH: 34
<212> TYPE: DNA
<213> ORGANISM: Artificial Sequence
<220> FEATURE:
<223> OTHER INFORMATION: Synthetic constructs

<400> SEQUENCE: 107
tattcatgct atttctctcc tttcaactct ttaa                                34

<210> SEQ ID NO 108
<211> LENGTH: 34
<212> TYPE: RNA
<213> ORGANISM: Artificial Sequence
<220> FEATURE:
<223> OTHER INFORMATION: Synthetic constructs

<400> SEQUENCE: 108
uauucaugcu auuucucucc uuucaacucu uuaa                                34

<210> SEQ ID NO 109
<211> LENGTH: 34
<212> TYPE: DNA
<213> ORGANISM: Artificial Sequence
<220> FEATURE:
<223> OTHER INFORMATION: Synthetic constructs

<400> SEQUENCE: 109
ttaaagagtt gaaaggagag aaatagcatg aata                                34

<210> SEQ ID NO 110
<211> LENGTH: 35
<212> TYPE: DNA
<213> ORGANISM: Artificial Sequence
<220> FEATURE:
<223> OTHER INFORMATION: Synthetic constructs

<400> SEQUENCE: 110
ttgttgtcct gaagaacgac ctgcatcgtt gtgta                               35

<210> SEQ ID NO 111
<211> LENGTH: 35
<212> TYPE: RNA
<213> ORGANISM: Artificial Sequence
<220> FEATURE:
<223> OTHER INFORMATION: Synthetic constructs

```
<400> SEQUENCE: 111
uuguuguccu gaagaacgac cugcaucguu gugua                          35

<210> SEQ ID NO 112
<211> LENGTH: 35
<212> TYPE: DNA
<213> ORGANISM: Artificial Sequence
<220> FEATURE:
<223> OTHER INFORMATION: Synthetic constructs

<400> SEQUENCE: 112
tacacaacga tgcaggtcgt tcttcaggac aacaa                          35
```

CRISPR-CAS10 SYSTEMS AND METHODS FOR PHAGE GENOME EDITING

CROSS REFERENCE TO RELATED APPLICATIONS

This application claims the benefit of U.S. Provisional Patent Application Ser. No. 62/465,929 filed Mar. 2, 2017, the disclosure of which is expressly incorporated herein by reference.

STATEMENT REGARDING FEDERALLY SPONSORED RESEARCH

This invention was made with Government Support under Grant No. 5K22AI113106-02 awarded by the National Institutes of Health. The Government has certain rights to the invention.

STATEMENT REGARDING SEQUENCE LISTING

Applicant submitted a Sequence Listing with filename "10025-175US1_2018_03_02 Sequence_Listing.TXT," created on Mar. 2, 2018, and 32 Kilobytes in size, in computer readable form and in compliance with 37 C.F.R. §§ 1.821-1.825 on Mar. 2, 2018. Applicant also submitted a revised Sequence Listing with filename "10025-178US1-Sequence-Listing_ST25.TXT," revised on Sep. 9, 2021, and 42 Kilobytes in size, in computer readable form and in compliance with 37 C.F.R. §§ 1.821-1.825 on Sep. 10, 2021. Each of the submitted Sequence Listings are hereby incorporated by reference.

FIELD

The present disclosure relates to CRISPR-Cas10 systems and methods for phage genome editing.

BACKGROUND

Staphylococci are dominant residents of human skin that play critical roles in health and disease. *S. epidermidis* is a ubiquitous skin commensal that promotes health by educating the immune system and helping to fight pathogens; however, this organism is also responsible for the majority of infections associated with medical implants. *S. aureus* can cause a range of antibiotic-resistant infections, from moderate to fatal, in a variety of body sites, and asymptomatic nasal carriage in about one-third of the population constitutes a major public health risk. Since the declining discovery rate of new antibiotics cannot keep up with the rate at which these bacteria acquire resistance, the development of alternative therapies has become imperative. Moreover, the opposing impacts of related *Staphylococcus* species underscore the critical need for antimicrobials with exquisite specificity.

Phages are bacterial viruses that attack a single host or subset of related hosts within the same genus, making them ideal for use as precision antimicrobials. While over 68 staphylococcal phages have been sequenced to date, fewer than 30% exhibit a virulent life cycle which is suitable for antimicrobial applications. Virulent staphylococcal phages have a swift reproductive cycle that destroys the host within minutes of infection. While desirable for antibacterial applications, their short resident time within the host limits access to their genomes, making them intractable by current genetic engineering techniques. Classical strategies that rely solely on homologous recombination between the phage genome and a donor DNA construct introduced into the cell are inefficient owing to low recombination rates and massive screening efforts required to recover the desired mutant. Other strategies that involve the transformation of bacterial hosts with whole phage genomes are unsuitable for use in natural *Staphylococcus* isolates, which exhibit low/no competence.

CRISPR-Cas is a class of prokaryotic immune systems that use small RNAs (crRNAs) and Cas nucleases to detect and destroy phages and other nucleic acid invaders. CRISPR loci harbor short (30-40 nucleotide) phage-derived sequences called "spacers" that encode crRNAs. Each crRNA combines with one or more Cas nucleases to form an effector complex, which detects and degrades cognate nucleic acid "protospacer" sequences. CRISPR-Cas systems are remarkably diverse, with two broad classes and six types (I-VI) currently described. Type I and Type II systems native to *Escherichia coli*, *Vibrio cholerae*, and *Streptococcus thermophilus* have recently been used in conjunction with homologous recombination to eliminate wild-type phages and thus facilitate the recovery of phages with desired mutations; however, the general applicability of this approach in other organisms using distinct CRISPR-Cas systems remains unknown.

Many staphylococci naturally possess Type III CRISPR-Cas systems (also called CRISPR-Cas10), thus providing an attractive tool already installed in the host chromosome to harness for phage genome engineering. Since over half their genes have unknown functions, virulent staphylococcal phages, when used as antimicrobials, carry inherent risk to cause unknown downstream side effects. Therefore, new methods are needed to genetically engineer virulent staphylococcal phages in order to eliminate genetic material unnecessary for their replication and equip them with additional genes that will enhance their bactericidal activity and therapeutic value. What is needed are new methods to genetically engineer virulent staphylococcal phages using a Type III-A CRISPR-Cas system (called CRISPR-Cas10).

The systems and methods disclosed herein address these and other needs.

SUMMARY

Disclosed herein are systems and methods for phage genome editing. In some embodiments, an endogenous bacterial CRISPR-Cas10 system is utilized to engineer phages for various biotechnology and therapeutic applications. In some embodiments, a heterologous CRISPR-Cas10 system can be introduced on a single plasmid.

In one aspect, disclosed herein is a phage genome editing system comprising:
a *Staphylococcus* bacterial cell that can be infected by a phage;
a vector comprising a crRNA that can hybridize to a nucleic acid sequence of the phage; and
a vector comprising a donor nucleic acid sequence (or rescue nucleic acid sequence), wherein the donor nucleic acid sequence comprises: a mutated nucleic acid sequence to be introduced into the phage, flanked by two nucleic acid sequences containing regions of homology to the phage genome.

In one aspect, disclosed herein is a phage genome editing system for use in a cell lacking an endogenous CRISPR-Cas10 system. In one aspect, disclosed herein is a phage genome editing system comprising:
a *Staphylococcus* bacterial cell that can be infected by a phage;

a vector comprising a crRNA that can hybridize to a nucleic acid sequence of the phage;

a vector comprising a CRISPR-Cas10 system, wherein the CRISPR-Cas10 system comprises CRISPR-associated genes csm1/cas10, csm2, csm3, csm4, csm5, csm6, and/or cash; and a vector comprising a donor nucleic acid sequence (or rescue nucleic acid sequence), wherein the donor nucleic acid sequence comprises: a mutated nucleic acid sequence to be introduced into the phage, flanked by two nucleic acid sequences containing regions of homology to the phage genome.

In one embodiment, the *Staphylococcus* bacterial cell is *Staphylococcus epidermidis*. In one embodiment, the *Staphylococcus* bacterial cell is *Staphylococcus aureus*. In one embodiment, the *Staphylococcus* bacterial cell has endogenous CRISPR sequences deleted. In one embodiment, the *Staphylococcus* bacterial cell lacks a CRISPR-Cas10 system altogether.

In one embodiment, the phage is a lytic phage. In one embodiment, the phage is a Podoviridae phage. In one embodiment, the phage is a Myoviridae phage. In one embodiment, the phage is a lytic variant of a Siphoviridae phage.

In one embodiment, the crRNA, CRISPR-associated genes, and the donor nucleic acid sequence (or rescue nucleic acid sequence) are comprised on the same vector. In one embodiment, the crRNA, CRISPR-associated genes, and the donor nucleic acid sequence (or rescue nucleic acid sequence) are comprised on different vectors. In one embodiment, the mutated nucleic acid sequence comprises at least one point mutation. In one embodiment, the mutated nucleic acid sequence comprises an insertion mutation. In one embodiment, the mutated nucleic acid sequence comprises a deletion mutation.

In one aspect, provided herein is a method for editing a phage genome, comprising: introducing into a *Staphylococcus* bacterial cell a vector comprising:

a crRNA that can hybridize to a nucleic acid sequence of the phage and a donor nucleic acid sequence, wherein the donor nucleic acid sequence (or rescue nucleic acid sequence) comprises: a mutated nucleic acid sequence to be introduced into the phage, flanked by two nucleic acid sequences containing regions of homology to the phage genome;

introducing a phage into the cell; and editing the phage genome to incorporate the mutated nucleic acid sequence.

In one embodiment, the *Staphylococcus* bacterial cell lacks an endogenous CRISPR-Cas10 system and comprises a vector containing the CRISPR-associated genes csm1/cas10, csm2, csm3, csm4, csm5, csm6, and cash, which encode the proteins comprising the CRISPR-Cas10 system.

In one embodiment, the two nucleic acid sequences containing regions of homology to the phage genome are from 50-1000 nucleotides. In one embodiment, the two nucleic acid sequences containing regions of homology to the phage genome are about 500 nucleotides. In one embodiment, the two nucleic acid sequences containing regions of homology to the phage genome are at least 50 nucleotides in length (for example, at least 50, at least 75, at least 100, at least 150, at least 200, at least 300, at least 400, at least 500, at least 600, at least 700, at least 800, at least 900, or at least 1000 nucleotides, etc.).

BRIEF DESCRIPTION OF THE DRAWINGS

The accompanying figures, which are incorporated in and constitute a part of this specification, illustrate several aspects described below.

DETAILED DESCRIPTION

Figure 1:
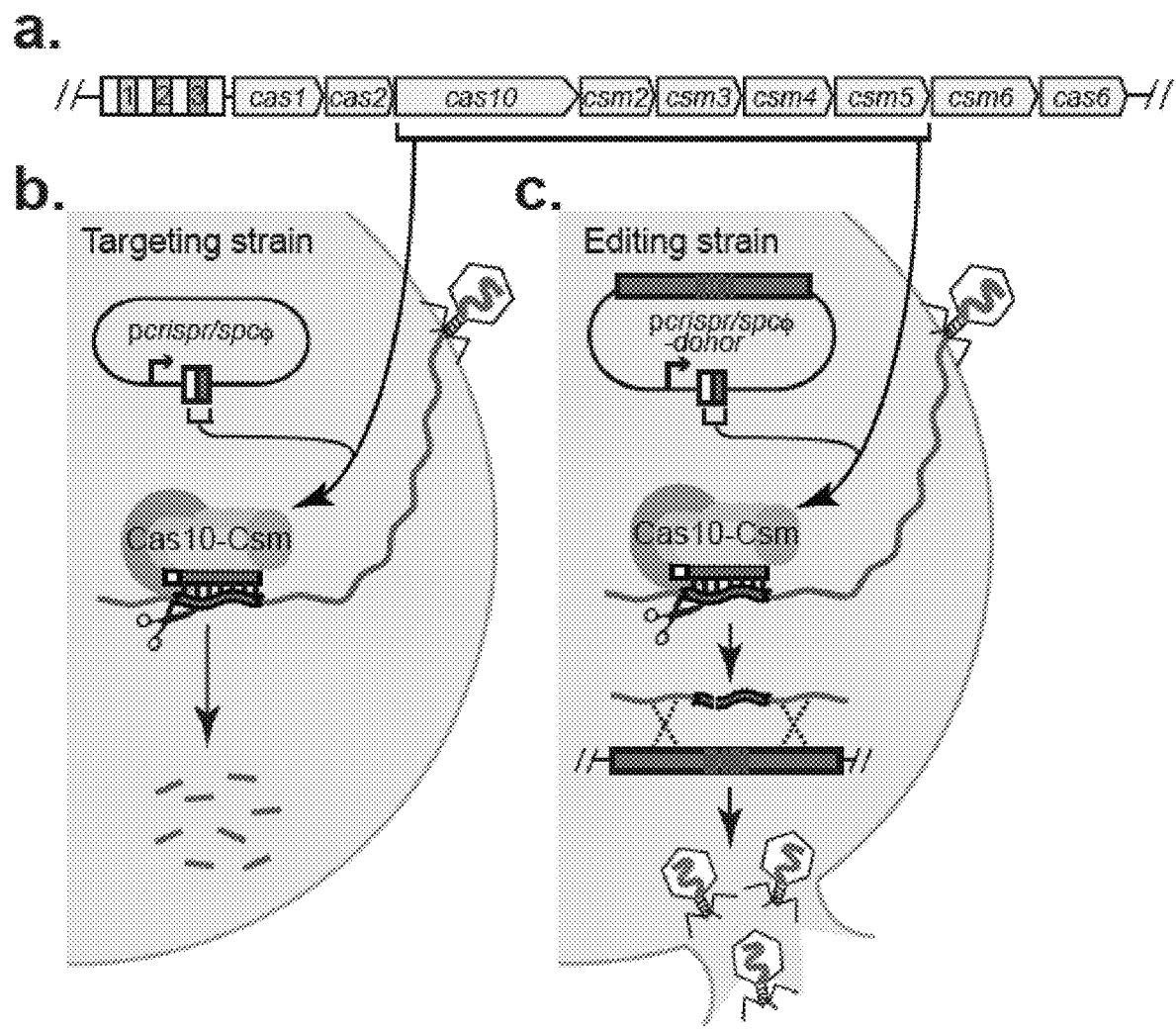
FIG. 1. A two-step approach for CRISPR-Cas10 assisted editing of virulent staphylococcal phages. The native *S. epidermidis* RP62a CRISPR-Cas locus (A) is composed of four repeats (white rectangles) three spacers (numbered rectangles) and nine CRISPR-associated cas and csm genes. Genes that encode members of the Cas10-Csm effector complex are indicated with a bracket. This system can be harnessed to facilitate phage genome editing in a two-step approach that involves the creation of a targeting strain (B) and an editing strain (C). In the first step, a plasmid called perispr/spcφ is constructed, which bears a single repeat and a spacer complementary to the phage of interest. This targeting construct is introduced into *S. epidermidis*, and the resulting *S. epidermidis*-perispr/spcφ strain is termed the targeting strain (B). The targeting strain is challenged with the phage by spotting phage lysate on top agar overlays to confirm that the selected spacer indeed protects against phage infection via CRISPR-Cas10 immunity. In the second step, perispr/spcφ plasmids that elicit efficient immunity are used as a backbone to construct perispr/spcφ-donor plasmids (C). Donor plasmids retain the targeting spacer, and have an additional phage-derived "donor" sequence (green rectangle), which bears desired mutations in the protospacer region (magenta stripes) flanked by sequences (>100 nucleotides) homologous to the phage genome on both sides. This donor construct is introduced into *S. epidermidis*, and the resulting *S. epidermidis*-perispr/spcφ-donor strain is termed the editing strain (C). This strain is combined with phages in liquid culture for various amounts of time, during which Cas10-Csm cleavage of the phage genome stimulates homology-directed repair (dashed lines) using the donor region in perispr/spcφ-donor as a repair template. Having incorporated the desired mutations, recombinant phage genomes can thus escape further cleavage by CRISPR-Cas10 and complete the infection cycle. The CRISPR-Cas10 system native to *S. epidermidis* LAM104, a derivative of RP62a with a deletion in spc1-3 of the CRISPR locus (36), was used as the background to create both the targeting and editing strains shown in the main figures of the paper. Phage editing was also conducted in a *S. aureus* RN4220 background by cloning the *S. epidermidis* CRISPR-Cas10 system on a plasmid and using a two-step approach similar to the one described above (data shown in FIG. 7).

Disclosed herein are systems and methods for phage genome editing. In some embodiments, an endogenous bacterial CRISPR-Cas10 system is utilized to engineer phages for various biotechnology and therapeutic applications.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used herein, the article "a," "an," and "the" means "at least one," unless the context in which the article is used clearly indicates otherwise.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, Tetrahedron Lett., 22:1859-1862 (1981), or by the triester method according to Matteucci, et al., J. Am. Chem. Soc., 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, Biochemistry, Third Ed., (1988), incorporated herein by reference for all purposes.

The term "polynucleotide" refers to a single or double stranded polymer composed of nucleotide monomers. In some embodiments, the polynucleotide is composed of nucleotide monomers of generally greater than 100 nucleotides in length and up to about 8,000 or more nucleotides in length.

The term "polypeptide" refers to a compound made up of a single chain of D- or L-amino acids or a mixture of D- and L-amino acids joined by peptide bonds.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" or "hybridizes" refers to a process of establishing a non-covalent, sequence-specific interaction between two or more complementary strands of nucleic acids into a single hybrid, which in the case of two strands is referred to as a duplex. The term "target" refers to a molecule that has an affinity for a given probe. Targets may be naturally-occurring or man-made molecules. Also, they can be employed in their unaltered state or as aggregates with other species.

A polynucleotide sequence is "heterologous" to a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from naturally occurring allelic variants.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

As used throughout, by a "subject" (or a "host") is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human.

The term "about" as used herein when referring to a measurable value such as an amount, a percentage, and the like, is meant to encompass variations of ±20%, ±10%, ±5%, or ±1% from the measurable value.

The term "donor nucleic acid sequence" as used herein can also be referred to in some systems as a "rescue nucleic acid sequence" or a "donor DNA construct."

The term "heterologous" as used herein refers to a system derived from a different organism.

As used herein, the "cas10" gene can also be referred to as the "csm1" gene, and the two terms cas10/csm1 are used interchangeably. At some points in the description, both names cas10/csm1 may be used for convenience, but the terms refer to the same gene.

Systems

Disclosed herein are systems and methods for phage genome editing. In some embodiments, an endogenous bacterial CRISPR-Cas10 system is utilized in combination with the systems and methods disclosed herein. In some embodiments, a heterologous bacterial CRISPR-Cas10 system is utilized in combination with the systems and methods disclosed herein.

In one aspect, disclosed herein is a phage genome editing system comprising:
a *Staphylococcus* bacterial cell that can be infected by a phage;
a vector comprising a crRNA that can hybridize to a nucleic acid sequence of the phage; and
a vector comprising a donor nucleic acid sequence, wherein the donor nucleic acid sequence comprises: a mutated nucleic acid sequence to be introduced into the phage, flanked by two nucleic acid sequences containing regions of homology to the phage genome.

In one aspect, disclosed herein is a phage genome editing system for use in a cell lacking an endogenous CRISPR-Cas10 system.

In one aspect, disclosed herein is a phage genome editing system comprising:
a *Staphylococcus* bacterial cell that can be infected by a phage;
a vector comprising a crRNA that can hybridize to a nucleic acid sequence of the phage;
a vector comprising a CRISPR-Cas10 system, wherein the CRISPR-Cas10 system comprises CRISPR-associated genes csm1/cas10, csm2, csm3, csm4, csm5, csm6, and/or cash; and
a vector comprising a donor nucleic acid sequence (or rescue nucleic acid sequence), wherein the donor nucleic acid sequence comprises: a mutated nucleic acid sequence to be introduced into the phage, flanked by two nucleic acid sequences containing regions of homology to the phage genome.

In another aspect, disclosed herein is a phage genome editing system comprising:
a *Staphylococcus* bacterial cell that can be infected by a phage;
a vector comprising a crRNA that can hybridize to a protospacer sequence of the phage; and
a vector comprising a donor nucleic acid sequence, wherein the donor nucleic acid sequence comprises: a mutated nucleic acid sequence to be introduced into the phage, flanked by two nucleic acid sequences containing regions of homology to the phage genome.

In some embodiments, the mutated nucleic acid sequence is in the targeted protospacer region. In some embodiments, the mutated nucleic acid sequence is in the homology arms distal to the protospacer region.

In one embodiment, the *Staphylococcus* bacterial cell is *Staphylococcus epidermidis*. In one embodiment, the *Staphylococcus* bacterial cell is *Staphylococcus aureus*. In one embodiment, the *Staphylococcus* bacterial cell has endogenous CRISPR sequences deleted or altogether absent. In one embodiment, the *Staphylococcus* bacterial cell lacks a CRISPR-Cas10 system altogether.

In one embodiment, the phage is a lytic phage. In one embodiment, the phage is a Podoviridae phage. In one embodiment, the phage is a Myoviridae phage. In one embodiment, the phage is a lytic variant of a Siphoviridae phage.

In one embodiment, the crRNA, CRISPR-associated genes, and the donor nucleic acid sequence (or rescue nucleic acid sequence) are comprised on the same vector. In one embodiment, the crRNA, CRISPR-associated genes, and the donor nucleic acid sequence (or rescue nucleic acid sequence) are comprised on different vectors. In one embodiment, the mutated nucleic acid sequence comprises at least one point mutation. In one embodiment, the mutated nucleic acid sequence comprises an insertion mutation. In one embodiment, the mutated nucleic acid sequence comprises a deletion mutation.

In one aspect, disclosed herein is a phage genome editing system comprising:
a *Staphylococcus* bacterial cell that can be infected by a phage;
a vector comprising a heterologous CRISPR-Cas10 system;
a vector comprising a crRNA that can hybridize to a nucleic acid sequence of the phage; and
a vector comprising a donor nucleic acid sequence, wherein the donor nucleic acid sequence comprises: a mutated nucleic acid sequence to be introduced into the phage, flanked by two nucleic acid sequences containing regions of homology to the phage genome.

In one aspect, disclosed herein is a phage genome editing system comprising:
a *Staphylococcus* bacterial cell without an endogenous CRISPR system that can be infected by a phage;
a vector comprising a heterologous CRISPR-Cas10 system;
a vector comprising a crRNA that can hybridize to a nucleic acid sequence of the phage; and
a vector comprising a donor nucleic acid sequence, wherein the donor nucleic acid sequence comprises: a mutated nucleic acid sequence to be introduced into the phage, flanked by two nucleic acid sequences containing regions of homology to the phage genome.

In one embodiment, the *Staphylococcus* bacterial cell lacks an endogenous CRISPR-Cas10 system and comprises a vector containing the CRISPR-associated genes csm1/cas10, csm2, csm3, csm4, csm5, csm6, and cas6, which encode the proteins comprising the CRISPR-Cas10 system.

In some embodiments, the sequence of the CRISPR-associated genes csm1/cas10, csm2, csm3, csm4, csm5, csm6, and cas6 is the nucleic acid sequence SEQ ID NO:1. In some embodiments, the sequence of the CRISPR-associated genes csm1/cas10, csm2, csm3, csm4, csm5, csm6, and cas6 is at least 50% identical (for example, at least 50%, at least 55%, at least 60%, at least 65%, at least 70%, at least 75%, at least 80%, at least 85%, at least 90%, at least 95%, or more) to the nucleic acid sequence SEQ ID NO:1.

In some embodiments, the sequence of the csm1/cas10 is the nucleic acid sequence SEQ ID NO:2. In some embodiments, the sequence of the csm1/cas10 is at least 50% identical (for example, at least 50%, at least 55%, at least 60%, at least 65%, at least 70%, at least 75%, at least 80%, at least 85%, at least 90%, at least 95%, or more) to the nucleic acid sequence SEQ ID NO:2.

In some embodiments, the sequence of the csm2 is the nucleic acid sequence SEQ ID NO:3. In some embodiments, the sequence of the csm2 is at least 50% identical (for example, at least 50%, at least 55%, at least 60%, at least 65%, at least 70%, at least 75%, at least 80%, at least 85%, at least 90%, at least 95%, or more) to the nucleic acid sequence SEQ ID NO:3.

In some embodiments, the sequence of the csm3 is the nucleic acid sequence SEQ ID NO:4. In some embodiments, the sequence of the csm3 is at least 50% identical (for example, at least 50%, at least 55%, at least 60%, at least 65%, at least 70%, at least 75%, at least 80%, at least 85%, at least 90%, at least 95%, or more) to the nucleic acid sequence SEQ ID NO:4.

In some embodiments, the sequence of the csm4 is the nucleic acid sequence SEQ ID NO:5. In some embodiments, the sequence of the csm4 is at least 50% identical (for example, at least 50%, at least 55%, at least 60%, at least 65%, at least 70%, at least 75%, at least 80%, at least 85%, at least 90%, at least 95%, or more) to the nucleic acid sequence SEQ ID NO:5.

In some embodiments, the sequence of the csm5 is the nucleic acid sequence SEQ ID NO:6. In some embodiments, the sequence of the csm5 is at least 50% identical (for example, at least 50%, at least 55%, at least 60%, at least 65%, at least 70%, at least 75%, at least 80%, at least 85%, at least 90%, at least 95%, or more) to the nucleic acid sequence SEQ ID NO:6.

In some embodiments, the sequence of the csm6 is the nucleic acid sequence SEQ ID NO:7. In some embodiments, the sequence of the csm6 is at least 50% identical (for example, at least 50%, at least 55%, at least 60%, at least 65%, at least 70%, at least 75%, at least 80%, at least 85%, at least 90%, at least 95%, or more) to the nucleic acid sequence SEQ ID NO:7.

In some embodiments, the sequence of the cas6 is the nucleic acid sequence SEQ ID NO:8. In some embodiments, the sequence of the cas6 is at least 50% identical (for example, at least 50%, at least 55%, at least 60%, at least 65%, at least 70%, at least 75%, at least 80%, at least 85%, at least 90%, at least 95%, or more) to the nucleic acid sequence SEQ ID NO:8.

In one embodiment, the heterologous CRISPR-Cas10 system is from a different species of *Staphylococcus*. In one embodiment, the heterologous CRISPR-Cas10 system is from a non-*Staphylococcus* bacterial cell. In one embodiment, the heterologous CRISPR-Cas10 system encodes a *S. epidermidis* CRISPR-Cas10 system with deletions in cast and cast, which are dispensable for immunity. In one embodiment, the heterologous CRISPR-Cas10 system is located on the same vector as the donor nucleic acid sequence. In one embodiment, the heterologous CRISPR-Cas10 system is located on the same vector as the crRNA sequence.

In one aspect, disclosed herein is a phage genome editing system comprising:
a bacterial cell that can be infected by a phage;
a vector comprising a crRNA that can hybridize to a nucleic acid sequence of the phage;
a vector comprising a CRISPR-Cas10 system, wherein the CRISPR-Cas10 system comprises CRISPR-associated genes csm1/cas10, csm2, csm3, csm4, csm5, csm6, and/or cash; and
a vector comprising a donor nucleic acid sequence (or rescue nucleic acid sequence), wherein the donor nucleic acid sequence comprises: a mutated nucleic acid sequence to be introduced into the phage, flanked by two nucleic acid sequences containing regions of homology to the phage genome.

Methods

In one aspect, provided herein is a method for editing a phage genome, comprising: introducing into a *Staphylococcus* bacterial cell a vector comprising:
a crRNA that can hybridize to a nucleic acid sequence of the phage and a donor nucleic acid sequence, wherein the donor nucleic acid sequence comprises: a mutated nucleic acid sequence to be introduced into the phage, flanked by two nucleic acid sequences containing regions of homology to the phage genome;
introducing a phage into the cell; and
editing the phage genome to incorporate the mutated nucleic acid sequence.

In one embodiment, the *Staphylococcus* bacterial cell is *Staphylococcus epidermidis*. In one embodiment, the *Staphylococcus* bacterial cell is *Staphylococcus aureus*. In one embodiment, the *Staphylococcus* bacterial cell has endogenous CRISPR sequences deleted. In addition to host strains that harbor endogenous CRISPR-Cas systems, such as *S. epidermidis* RP62a, *S. capitis* CR01, and *S. pseudointermedius* ED99, other CRISPR-less strains can be used.

In one embodiment, the phage is a lytic phage. In one embodiment, the phage is a Podoviridae phage. In one embodiment, the phage is a Myoviridae phage. In one embodiment, the phage is a lytic variant of a Siphoviridae phage.

In one embodiment, the crRNA and the donor nucleic acid sequence are comprised on the same vector. In one embodiment, the crRNA and the donor nucleic acid sequence are comprised on different vectors. In one embodiment, the mutated nucleic acid sequence comprises at least one point mutation. In one embodiment, the mutated nucleic acid sequence comprises an insertion mutation. In one embodiment, the mutated nucleic acid sequence comprises a deletion mutation.

In one embodiment, the two nucleic acid sequences containing regions of homology to the phage genome are from 50-1000 nucleotides. In one embodiment, the two nucleic acid sequences containing regions of homology to the phage genome are about 500 nucleotides. In one embodiment, the two nucleic acid sequences containing regions of homology to the phage genome are at least 50 nucleotides in length (for example, at least 50, at least 75, at least 100, at least 150, at least 200, at least 300, at least 400, at least 500, at least 600, at least 700, at least 800, at least 900, or at least 1000 nucleotides, etc.).

The systems and methods herein can be used to engineer phages with biotechnological value, and benefit the diverse fields that employ phages such as biosensors, precision antimicrobials, and nanomaterials.

In one embodiment, the systems disclosed herein are used to engineer phage-based precision antimicrobials. Nonessential genes are identified, and can be eliminated to (a) remove any unanticipated downstream effects of these genes, and (b) create space for a desired genetic payload. Identifying the genes responsible for host specificity is also important because phages are developed with tunable/expandable host ranges, which broaden their use as antimicrobials.

Phages are natural predators of bacteria. Thus, phages are engineered with minimal genetic content to create phage with only known components to alleviate regulatory concerns. Phage are also engineered to kill the bacteria without lysis of the bacteria to prevent release of bacterial toxins.

Phages themselves have been tapped as a wellspring of technologies that span across disciplines. In addition to the myriad of phage-derived enzymes that are staples in common lab protocols (e.g. T4 DNA ligase and T7 RNA polymerase), and phage lytic enzymes (lysins) that are explored as therapeutics, whole phages are powerful tools. Due to their exquisite host specificity, phages are employed as precision antimicrobials, and biosensors for pathogen detection in food and the environment. Phage display of peptides or other conjugates on their capsids has enabled targeted drug delivery, vaccine development, and affinity screening of random peptides. Phages have also been used as scaffolds to build nanomaterials and nanoscale devices.

In some embodiments, podophage Andhra (V2) can be engineered with insertions and deletions. In-frame deletions are introduced into small intergenic regions. Also, nucleic acids can be inserted (small and large): 1) for example, a 6-His tag is placed on the major capsid protein (or other structural protein) to allow for phage immobilization on a solid Ni' substrate, and 2) green fluorescent protein is inserted immediately downstream of the capsid protein (or in any other permissive genomic location), creating a phage V2 biosensor that emits a fluorescent signal in the presence of its host strain.

EXAMPLES

The following examples are set forth below to illustrate the systems, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Strategies for Editing Virulent Staphylococcal Phages Using CRISPR-Cas10

Staphylococci are prevalent skin-dwelling bacteria that are also leading causes of antibiotic-resistant infections. Viruses that infect and lyse these organisms (virulent staphylococcal phages) can be used as alternatives to conventional antibiotics and represent promising tools to eliminate or manipulate specific species in the microbiome. However, since over half their genes have unknown functions, virulent staphylococcal phages carry inherent risk to cause unknown downstream side effects. Further, their swift and destructive reproductive cycle make them intractable by current genetic engineering techniques. CRISPR-Cas10 is an elaborate prokaryotic immune system that employs small RNAs and a multi-subunit protein complex to detect and destroy phages and other foreign nucleic acids. Some staphylococci naturally possess CRISPR-Cas10 systems, thus providing an attractive tool already installed in the host chromosome to harness for phage genome engineering. However, the efficiency of CRISPR-Cas10 immunity against virulent staphylococcal phages and corresponding utility as a tool to facilitate their genome editing has not been explored. Here, it is shown that the CRISPR-Cas10 system native to *Staphylococcus epidermidis* exhibits robust immunity against diverse virulent staphylococcal phages. Based on this activity, a general two-step approach was developed to edit these phages that relies upon homologous recombination machinery encoded in the host. Variations of this approach to edit toxic phage genes and access phages that infect CRISPR-less staphylococci are also presented. This versatile set of genetic tools enables the systematic study of phage genes of unknown functions and the design of genetically defined phage-based antimicrobials that can eliminate or manipulate specific *Staphylococcus* species.

Background

Staphylococci are dominant residents of human skin that play critical roles in health and disease. *S. epidermidis* is a ubiquitous skin commensal that promotes health by educating the immune system and preventing colonization by more aggressive skin pathogens (1-4); however, this organism is also responsible for the majority of infections associated with medical implants (5). *S. aureus* can cause a range of antibiotic-resistant infections, from moderate to fatal, in a variety of body sites (6), and asymptomatic nasal carriage in about one-third of the population constitutes a major risk factor for more serious, invasive infections (7-9). Since the declining discovery rate of new antibiotics cannot keep up with the rate at which these bacteria acquire resistance, the development of alternatives to conventional antibiotics has become imperative. Furthermore, the opposing impacts of related *Staphylococcus* species underscore the critical need for antimicrobials with exquisite specificity.

Bacterial viruses (phages) attack a single host or subset of related hosts within the same genus (10), making them ideal for use as precision antimicrobials. Staphylococcal phages are classified into three morphological families and harbour discrete genome lengths: Podoviridae (<20 kb), Siphoviridae (~40 kb), and Myoviridae (>125 kb) (11). While over 68 staphylococcal phages have been sequenced to date (12, 11), the majority exhibit a temperate lifestyle that is unsuitable for antimicrobial applications. Temperate staphylococcal phages, which belong to the family Siphoviridae, can integrate into the host chromosome and promote pathogenicity by mobilizing virulence factors and pathogenicity islands (13, 14). Fewer than 30% of sequenced staphylococcal phages are naturally virulent, belonging to the families Myoviridae and Podoviridae (11). These phages exhibit a swift reproductive cycle that destroys the host within minutes of infection. While optimal for antimicrobial applications (15, 16), virulent staphylococcal phages also carry an inherent risk of eliciting detrimental side-effects—over half their genes have unknown functions (11) and their molecular interactions with the bacterial host remain poorly understood. As examples of such side-effects, virulent phages have the potential to facilitate horizontal gene transfer (17, 18), promote biofilm formation (19), and/or elicit unanticipated immune responses (20). These issues are compounded by the need to use cocktails of diverse phages for antimicrobial applications to curb the emergence of phage-resistant pathogens (15, 16). Thus, gaining a better understanding of virulent phages and engineering phage-based antimicrobials with well-defined genetic components can alleviate safety concerns, regulatory constraints, and manufacturing challenges associated with the implementation of whole-phage therapeutics (21).

Virulent staphylococcal phages are intractable by most current genetic engineering techniques (22). Classical strategies that rely solely on homologous recombination between the phage genome and a donor DNA construct are inefficient owing to low recombination rates and massive screening efforts required to recover the desired mutant (23). Other strategies that involve the transformation of bacterial hosts with whole phage genomes (24, 25) are unsuitable for use in natural *Staphylococcus* isolates, which exhibit low/no competence (26). However, recent reports have shown that CRISPR-Cas (Clustered regularly-interspaced short palindromic repeats-CRISPR-associated) systems in distinct bacteria can facilitate phage editing (27-30). CRISPR-Cas systems are a diverse class of prokaryotic immune systems that use small CRISPR RNAs (crRNAs) and Cas nucleases to detect and destroy phages and other nucleic acid invaders (31-36). In these systems, CRISPR loci maintain an archive of short (30-40 nucleotide) invader-derived sequences called "spacers" integrated between similarly sized DNA repeats. The repeat-spacer array is transcribed and processed to generate crRNAs that each specify a single target for destruction. CrRNAs combine with one or more Cas nucleases to form an effector complex, which detects and degrades nucleic acid sequences (called "protospacers") complementary to the crRNA. CRISPR-Cas systems are remarkably diverse, with two broad Classes and six Types (I-VI) currently described (37, 38). Types I and II CRISPR-Cas systems have recently been used in conjunction with homologous recombination to facilitate phage editing (27-30); however, the general applicability of this approach in other organisms using distinct CRISPR-Cas systems remains unknown.

In this study, the utility of the Type III-A CRISPR-Cas system native to *S. epidermidis* RP62a (here onward called CRISPR-Cas10) was investigated as an engineering platform for virulent staphylococcal phages. This system has three spacers (spc1-3) and nine CRISPR-associated (cas and csm) genes (FIG. 1A) that block plasmid transfer (36) and phage infection (39, 40) with a multi-subunit complex called Cas10-Csm (41). This system degrades both DNA and RNA protospacers in a transcription-dependent manner (39, 42), thus providing an opportunity for temperate phages to escape immunity and integrate peacefully into the host chromosome, provided their lytic genes remain silenced (39). The efficiency of CRISPR-Cas10 immunity against naturally virulent staphylococcal phages and corresponding utility as a tool to facilitate editing of these phages has not been explored. In this example, a general two-step approach is described to harness CRISPR-Cas10 and host-encoded recombination machinery to edit virulent staphylococcal phages (FIGS. 1 B and C). Variations of this approach were also developed to edit phage genes that are toxic to the host (such as genes that encode lysins, cell wall hydrolytic enzymes), and to show that a heterologous CRISPR-Cas10 system encoded on a plasmid can be used to edit phages that attack a *S. aureus* strain devoid of a natural CRISPR-Cas system. Additionally, in order to facilitate the design of CRISPR-Cas10 targeting constructs, a Python script was developed to identify all optimal protospacers in a given phage gene. This versatile set of genetic tools enables i) the systematic study of genes of unknown function in staphylococcal phages and ii) the design of phage-based antimicrobials with well-defined genetic components.

Results and Discussion

CRISPR-Cas10 elicits robust targeting of virulent staphylococcal phages

Figure 2:
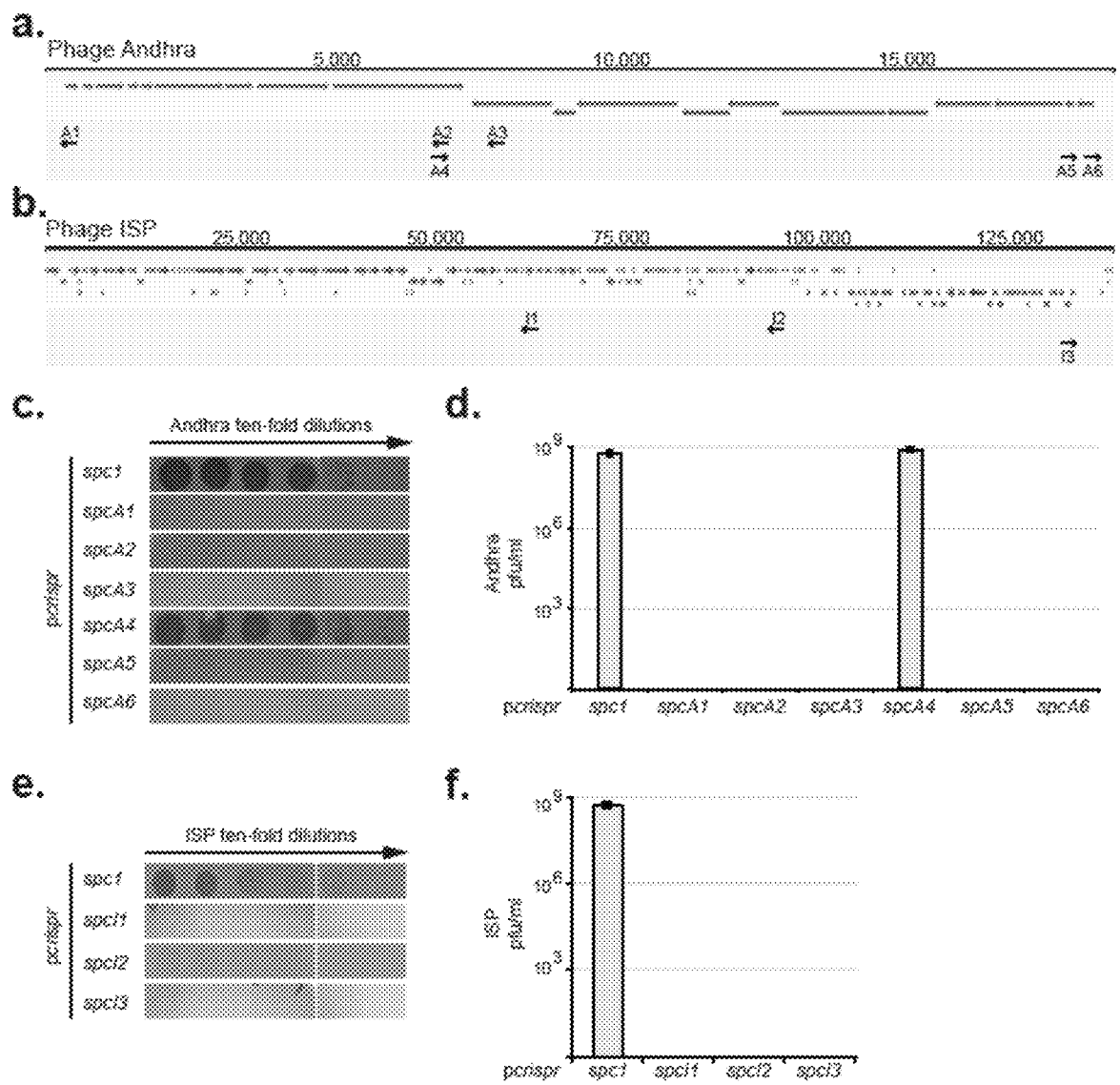
FIG. 2. CRISPR-Cas10 elicits robust immunity against virulent phages at multiple genetic loci. Schematic representations of genomes of phages Andhra (A) and ISP (B). Genome coordinates are indicated on top, and open reading frames (ORFs) transcribed in the rightward and leftward directions are indicated with coloured arrows (magenta and green, respectively). Spacers that were tested in this study (spcA1-A6 and spcI1-I3) are indicated with black arrows in the shaded track below each targeted ORF. Targeting *S. epidermidis* strains harbouring indicated perispr/spcφ plasmids were challenged with phages Andhra (C and D) and ISP (E and F) by spotting ten-fold dilutions of each phage atop lawns of corresponding targeting strains. Panels C and E show a representative plate, while panels D and F show an average number of plaque forming units (pfu) per milliliter in three independent trials (±S.D.). Where bars are absent, pfu/ml was below the limit of detection.

The effectiveness of CRISPR-Cas10 as a counter-selection tool to facilitate virulent phage editing relies upon the efficiency at which this system can eliminate virulent phages. Therefore, CRISPR-Cas10 immunity was first tested against representatives from both virulent staphylococcal phage families: Podoviridae phage Andhra (43) and Myoviridae phage ISP (12). Since the *S. epidermidis* CRISPR-Cas10 system lacks natural spacers targeting these phages, the system had to be re-programmed to target Andhra and ISP. In order to re-program CRISPR-Cas10 to recognize these phages, the plasmid perispr was used, which contains a single repeat-spacer unit from CRISPR-Cas10 (44), as a backbone to create a suite of perispr/spcϕ plasmids, which encode single spacers that target a variety of protospacer loci spanning the genomes of Andhra and ISP (FIGS. 2 A and B). Nine protospacer regions were selected (Table 1) according to the two criteria that permit the recognition and destruction of foreign DNA by Type III-A CRISPR-Cas systems (39, 45). First, 35-nucleotide protospacers were selected with little or no complementarity between the "antitag" region adjacent to the protospacer and the corresponding eight-nucleotide tag sequence on the 5'-end of the crRNA (5'-ACGAGAAC). Second, protospacers were selected in coding regions, with corresponding crRNAs designed to bind to the coding DNA strand (and the mRNA). To test for a potential targeting bias toward genes transcribed early or late in the phage replication cycle, protospacers were selected in putative early genes (encoding DNA polymerases) and late genes (encoding cell wall hydrolytic enzymes) in both phages (Table 1). The resulting targeting plasmids (perispr/spcA1-/spcA6 and perispr/spcI1-/spcI3) were introduced into *S. epidermidis* LAM104, a variant of *S. epidermidis* RP62a that lacks spc1-3 of the native CRISPR locus (36). *S. epidermidis* LAM104 strains harbouring a perispr/spcϕ plasmid are called "targeting strains" (FIG. 1 B). A control targeting strain bearing perispr/spc1 was also included, which contains spc1 of the native CRISPR locus (Table 1), a plasmid-targeting spacer unrelated to any known phage (36).

In order to test the efficiency of CRISPR-Cas10 immunity in the presence of each spacer, corresponding targeting strains were challenged with phages by spotting phage dilutions atop lawns of each strain. The control targeting strain bearing perispr/spc1 remained susceptible to both Andhra (FIGS. 2 C and D) and ISP (FIGS. 2 E and F), as evidenced by the appearance of phage plaques. Equally susceptible was the targeting strain that harboured perispr/spcA4, which targets the same protospacer region as perispr/spcA2, but encodes crRNAs complementary to the non-coding (i.e. template) strand of the protospacer. This observation is consistent with previous studies that showed CRISPR-Cas10 immunity only occurs in the presence of base-pair complementarity between the crRNA and the coding DNA strand, along with its corresponding mRNA (39, 42). One exception seems to be perispr/spcA3, which targets a non-coding strand, yet still provides immunity. This could be explained by the presence of bi-directional transcription at the targeted locus due to leakage from the adjacent gene, which is transcribed in the opposite direction. Nonetheless, when coding strands are targeted, CRISPR-Cas10 affords complete protection against Andhra and ISP at all tested loci (FIGS. 2 D and F), as evidenced by the absence of phage plaques, even in the presence the most concentrated phage lysate ($10^9$ pfu/mL). Notably, spacers targeting putative early genes (spcA2 and spcI1) and late genes (spcA3 and spcI3) were equally effective in directing complete protection against phage infection.

The altogether absence of phages that naturally escape CRISPR-Cas10 immunity (CRISPR escaper mutants, or CEMs) is striking. CEMs are phages that have acquired random mutations in the protospacer and/or adjacent regions that allow escape from CRISPR-Cas immunity. The evolution of CEMs has been well documented in organisms that harbour Types I and II CRISPR-Cas systems (34, 46, 47). This occurs because immunity in these systems relies upon perfect complementarity between the crRNA and protospacer in a short (6-8 nucleotide) seed sequence (47-49) and a protospacer adjacent motif (PAM) (50). Therefore even a single nucleotide substitution within the seed or PAM can allow phages to naturally escape interference without acquiring the desired mutations. The appearance of CEMs was observed at varying frequencies when Types I and II CRISPR-Cas systems were used to edit phages (27-30). In contrast, neither a PAM nor a seed sequence has been identified for CRISPR-Cas10 (40, 45). This system is also extremely tolerant to mismatches between the crRNA and protospacer during anti-phage immunity (40).

CRISPR-Cas10 Immunity Facilitates the Recovery of Virulent Phage Recombinants

Figure 3:
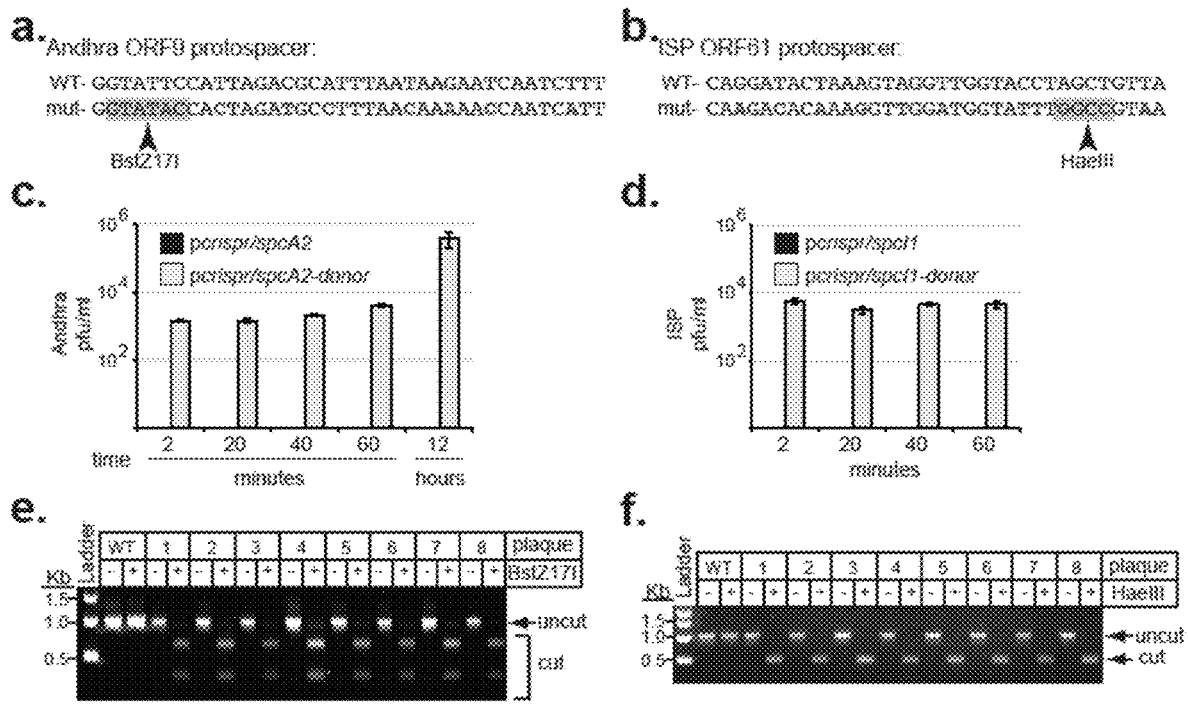
FIG. 3. CRISPR-Cas10 enables the recovery of recombinant phages. The protospacer regions of Andhra ORFS, having nucleic acid sequence SEQ ID NO: 75 and mutant sequence SEQ ID NO: 76 (A), and ISP ORF 61, having nucleic acid sequence SEQ ID NO: 77 and mutant sequence SEQ ID NO: 78 (B), are shown in the 5'-3' direction. The wild-type sequence appears on top, and mutant variants included in donor plasmids appears below. Mutated nucleotides are shown in magenta and restriction enzyme recognition and cut sites added with the mutations are highlighted in green and indicated with an arrow, respectively. Editing S. epidermidis strains harbouring indicated perispr/spcϕ-donor plasmids were co-cultured with phages Andhra (C) and ISP (D) for varying amounts of time as shown. As controls, targeting S. epidermidis strains harbouring indicated perispr/spcϕ plasmids were co-cultured with appropriate phages in parallel for the same amounts of time. Following the co-culturing period, phage-host mixtures were plated and plaques were enumerated on the following day. Experiments were carried out in triplicate and average pfu/ml (±S.D.) are shown for targeting strains (black bars) and editing strains (grey bars). Where bars are absent, pfu/ml was below the limit of detection. (E and F) Ten plaques were selected from each 60-minute co-culture plate (with the editing strains), and phage genomes were purified, PCR amplified across the edited region, and PCR products were subjected to digestion with indicated restriction enzymes. Digests were resolved on a 1% agarose gel and visualized with ethidium bromide. Restriction digests from eight out of ten selected plaques for phages Andhra (E) and ISP (F) are shown. Wild-type phages were included as a negative control, and uncut and cut DNA fragments are indicated with arrows/brackets.

The efficient immune response that CRISPR-Cas10 mounts against Andhra and ISP, and consequent failure of these phages to naturally escape immunity, suggest this system could provide a robust counter-selection mechanism to facilitate recovery of phage recombinants that have acquired desired mutations from a donor DNA construct. To test this, donor DNA constructs (called "donor sequences") were introduced into targeting plasmids perispr/spcA2 and perispr/spcI1, which encode crRNAs that specify immunity against the DNA polymerase genes of Andhra (ORF 9) and ISP (ORF 61), respectively. The donor sequences are composed of 500 nucleotide homology arms flanking the protospacer with several silent mutations introduced into the protospacer region (FIGS. 3 A and B). The silent mutations are designed to allow phage escape from CRISPR-Cas10 immunity and also add a unique restriction enzyme cut site. The perispr/spcA2 and perispr/spcI1 plasmids were used as backbones to create perispr/spcA2-donor and perispr/spcI1-donor, respectively. These plasmids, which contain both a targeting spacer and a donor sequence, were introduced into *S. epidermidis* LAM104. *S. epidermidis* LAM104 strains harbouring a perispr/spcϕ-donor plasmid are called "editing strains" (FIG. 1 C).

Figure 5:
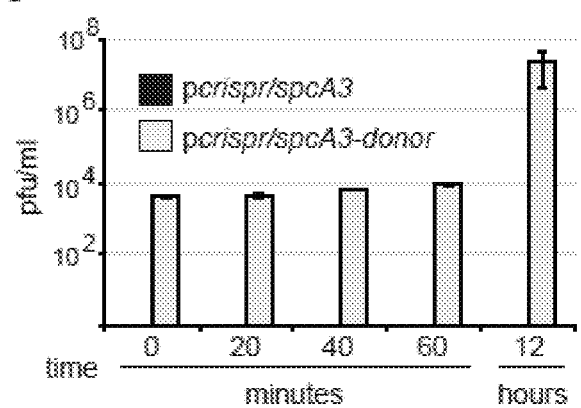
FIG. 5. CRISPR-Cas10 assisted editing of phage Andhra ORF10. Accompanies FIG. 3. (A) The protospacer of Andhra ORF10, having nucleic acid sequence SEQ ID NO: 79 and mutant sequence SEQ ID NO: 80, is shown in the 5'-3' direction. The wild-type sequence (top) and mutant variant (bottom) are shown. Mutated nucleotides are indicated in magenta and the AflII restriction enzyme cut site added with the mutations is indicated with green highlighting and an arrow. (B) The editing S. epidermidis strain harbouring perispr/spcA3-donor and the targeting strain harbouring perispr/spcA3 (as a negative control) were co-cultured with Andhra for indicated amounts of time. Phage-host mixtures were then plated and plaques were enumerated on the following day. Experiments were carried out in triplicate and average pfu/ml (±S.D.) are shown for targeting strains (black bars) and editing strains (grey bars). Where bars are absent, pfu/ml was below the limit of detection. (C) Ten plaques were selected from the editing strain 60-minute co-culture plate, and phage genomes were purified, PCR amplified across the edited region, and PCR products were subjected to digestion with AflII. Digests were resolved on a 1% agarose gel and visualized with ethidium bromide. Restriction digests from eight out of ten selected plaques are shown. DNA from a wild-type phage was included as a negative control, and uncut and cut DNA fragments are indicated with an arrow/bracket.
Figure 5:
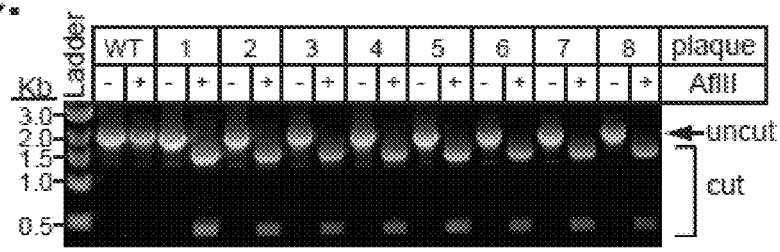

Direct plating of phages atop lawns of the corresponding editing strains failed to allow plaque formation (not shown); however, when editing strains were infected with their respective phages in liquid culture for as few as two minutes, plaques were observed (FIGS. 3 C and D). Plaque numbers on the editing strains increased with time, likely due to multiple phage replication cycles occurring over the longer time periods. Importantly, no plaques resulted when the corresponding targeting strains were co-cultured with phages under identical conditions, suggesting all phages replicating on the editing strains have likely acquired the mutations. To confirm this, twenty putative recombinants were selected for each phage, and their genomes were PCR amplified in regions encompassing the protospacers. PCR products from ten putative recombinants were subjected to digestion with the appropriate restriction enzymes (FIGS. 3 E and F, and not shown), and the remaining ten were sequenced. Strikingly, 100% of selected plaques contained the intended mutations in exclusion of any others within the sequenced region (flanking 400+ nucleotides). To show this technique can be applied to distinct genetic loci transcribed in the opposite direction, Andhra ORF10 (a putative late gene) was edited using the same approach, and similar results were obtained (FIG. 5). Recombination efficiencies overall were low ($10^{-5}$ at best, Table 2), perhaps due to a kinetic advantage for CRISPR cleavage over recombination events at the targeted locus. Nonetheless, the more than 99% efficiency of CRISPR-Cas10 immunity against wild-type phages effectively revealed the rare recombinants.

Alternative Strategies to Edit Toxic Phage Genes

Figure 4:
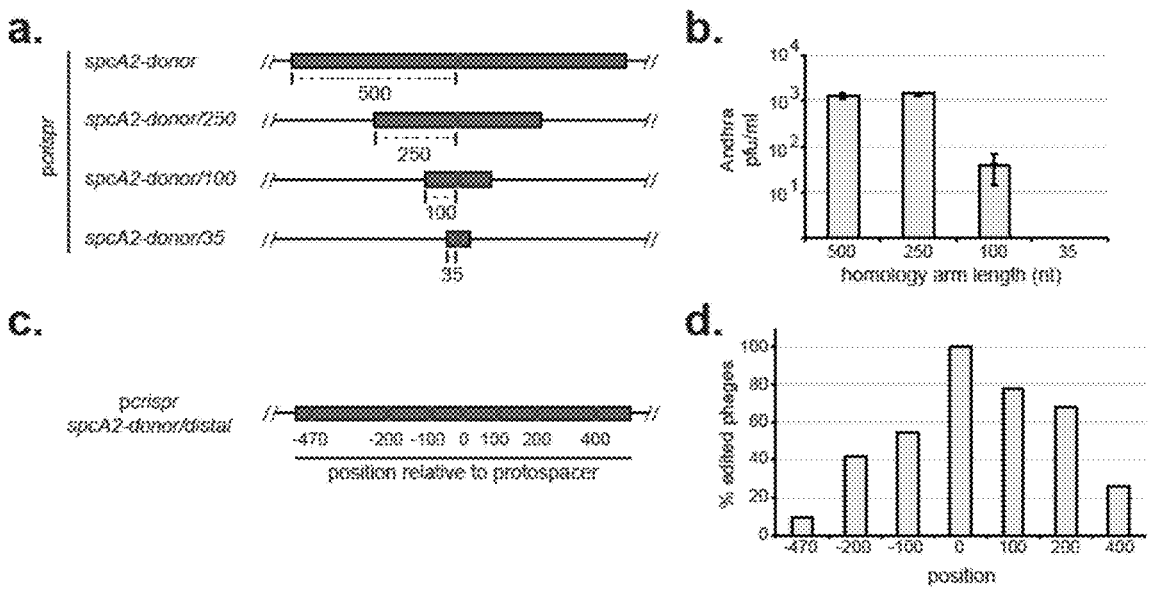
FIG. 4. Alternative approaches to facilitate editing of phage-derived toxic genes. (A) Variants of perispr/spcA2-donor plasmids with homology arm lengths of 500, 250, 100 or 35 nucleotides are shown. (B) Editing strains harbouring perispr/spcA2-donor plasmids with indicated homology arm lengths were co-cultured with phage Andhra for 60 minutes, and resulting plaques were enumerated (grey bars). The experiment was carried out in triplicate and average pfu/ml (±S.D.) are shown. (C) A variant of the perispr/spcA2-donor plasmid called perispr/spcA2-donor/distal is shown, which contains silent mutations at regular intervals from the protospacer region. Positions of mutations are shown with magenta bars (refer to FIG. 6 for the sequence). (D) An editing S. epidermidis strain bearing this plasmid was co-cultured with phage Andhra for 60 minutes and the mixture was plated. On the following day, 31 plaques were selected, phage genomes were extracted and PCR amplified across the donor sequence region, and scored for the presence or absence of silent mutations at each position (refer to Table 3 for breakdown of mutations per phage). Shown are the fraction of phages that acquired mutations at each position.
Figure 6:
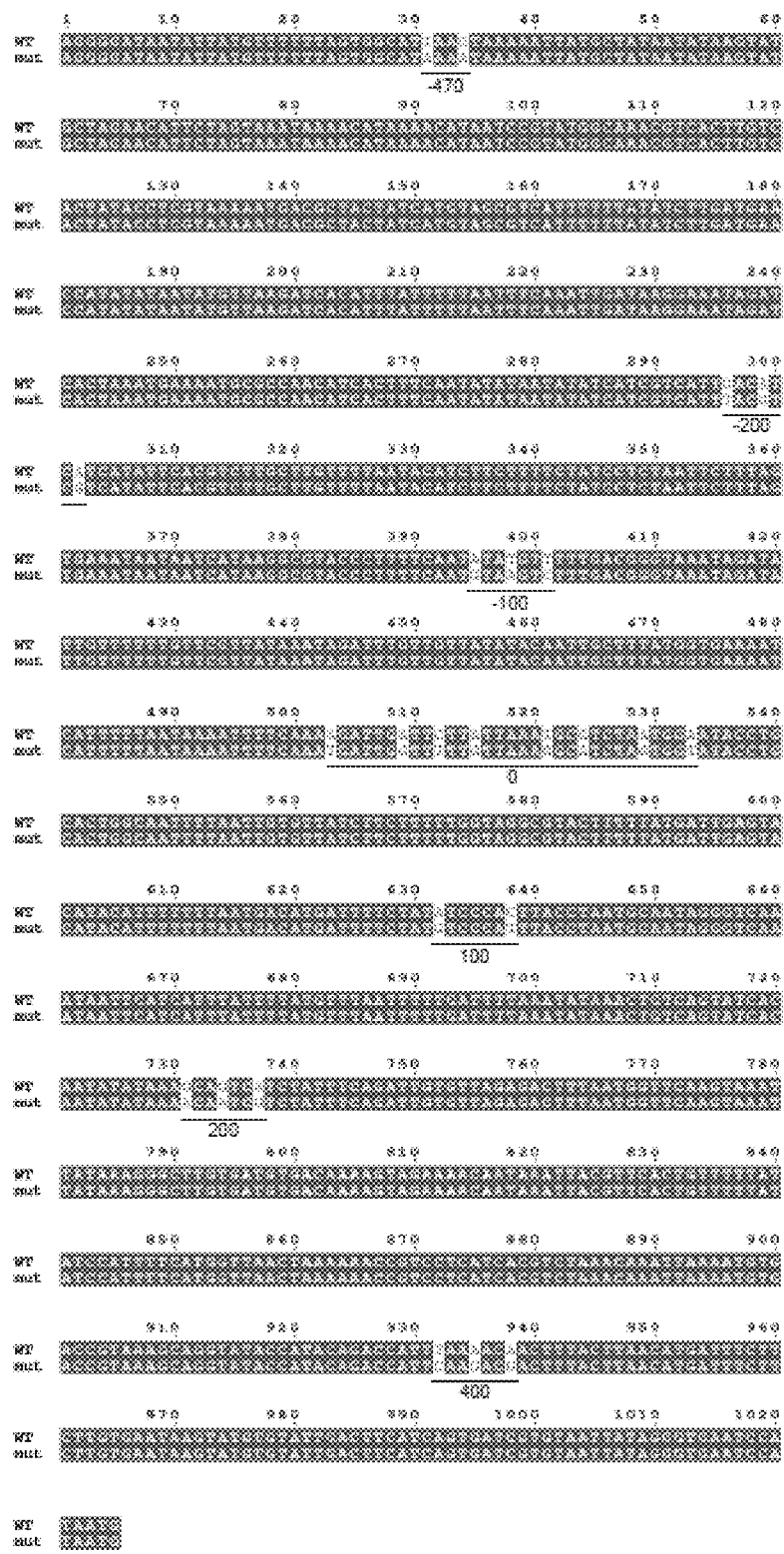
FIG. 6. The donor region of plasmid perispr/spcA2-donor/distal. Accompanies FIG. 4. An alignment of wild-type phage Andhra ORFS sequence, having nucleic acid sequence SEQ ID NO: 81, (top) and corresponding donor region in the plasmid perispr/spcA2-donor/distal, having mutant sequence SEQ ID NO: 82, (bottom) is shown. Nucleotides with perfect homology are highlighted in red, and silent mutations appear with white background. The positions of the protospacer (0) and mutations upstream or downstream of it are underlined and indicated at each position with negative or positive numbers, respectively.

Since phage genomes encode proteins that are toxic to the bacterial host, (such as lysins, which degrade cell walls), such genetic loci might be refractory to overexpression on perispr/spcϕ-donor plasmids, thus hampering this approach. To overcome this issue, the minimal homology arm length required to facilitate recombination was determined. The plasmid perispr/spcA2-donor, which contains 500 nucleotide homology arms, was used as a backbone to create similar plasmids with 250, 100 or 35 nucleotide homology arms (FIG. 4A). Co-culturing Andhra with editing strains harbouring these constructs showed that 100 nucleotides on either side of the protospacer were sufficient to facilitate homologous recombination (FIG. 4B). This shorter length thus minimizes the length of phage-derived sequences needed in the perispr/spcϕ-donor plasmids. The use of this system was also investigated to introduce mutations distal to the targeted region, which would allow more flexibility in the selection of phage-derived sequences to include in the perispr/spcϕ-donor plasmids. To test this, perispr/spcA2-donor/distal was created, which bears silent mutations at regular intervals distal to the mutant protospacer (FIG. 4C and FIG. 6). The editing strain harbouring this plasmid was co-cultured with Andhra, and phages from 31 random plaques were sequenced across the donor region. One hundred percent (100%) of the recombinant phages selected acquired the mutations at the protospacer in order to escape CRISPR-Cas10 immunity (FIG. 4D and Table 3). Importantly, a subset of these phages also acquired distal mutations, up to 470 nucleotides from the protospacer. Notably, the mutations incorporated at position −470 occur in ORF10, which encodes a lytic enzyme that is toxic to *S. epidermidis* and *S. aureus* strains (43). By minimizing the length of the donor sequence and allowing flexibility in the placement of the desired mutation(s) relative to the protospacer, these alternative strategies facilitate editing of toxic phage genes.

Editing *S. aureus* Phages with a Heterologous System

Figure 7:
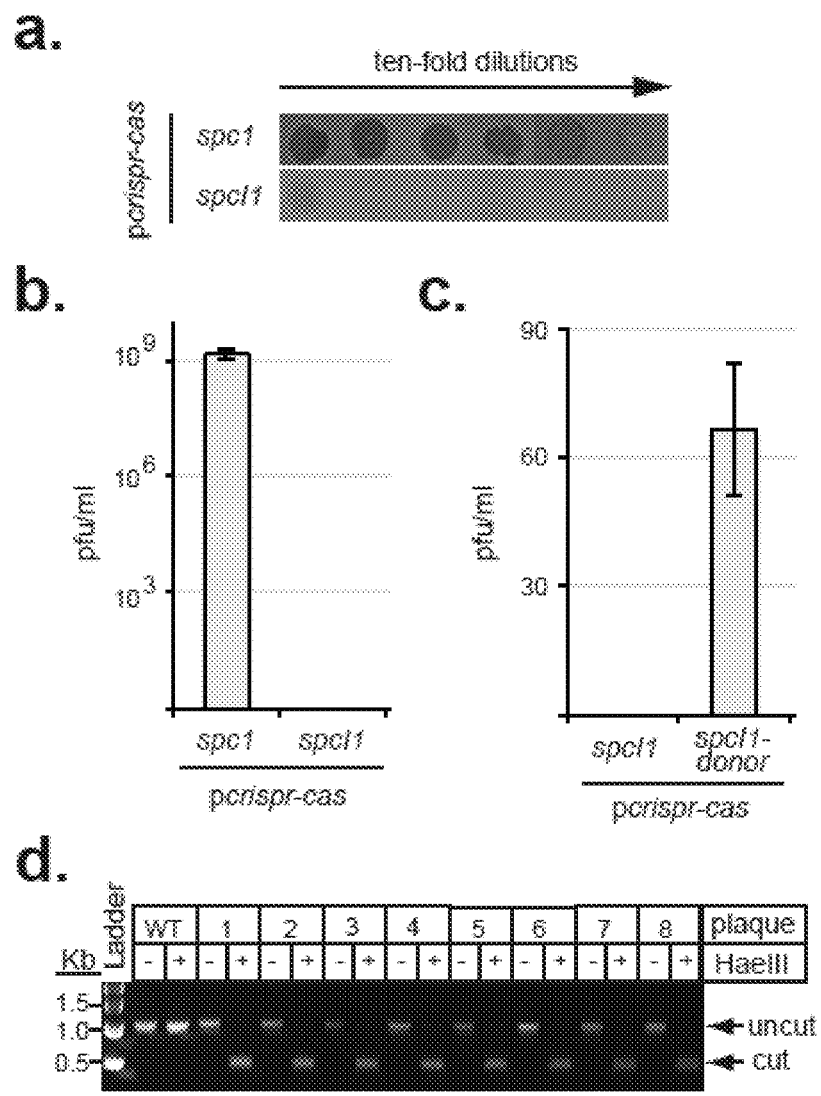
FIG. 7. CRISPR-Cas10 assisted editing in S. aureus. (A) Targeting S. aureus RN4220 strains harbouring indicated perispr-cas/spcϕ plasmids were challenged with phage ISP by spotting ten-fold dilutions atop lawns of the targeting strains. (B) Triplicate targeting experiments were performed, and average pfu/ml are shown (±S.D.). (C) S. aureus RN4220 strains harbouring indicated perispr-cas plasmids were co-cultured with phage ISP for 90 minutes, and mixtures were plated. The following day, pfu/ml were enumerated. The experiment was performed in triplicate and averages of pfu/ml (±S.D.) are shown. Where bars are absent, pfu/ml was below the limit of detection. (D) Ten plaques were selected following co-culture with the editing strain, phage genomes were extracted, PCR amplified across the edited region, and PCR products were subjected to digestion with HaeIII. Digests were resolved on a 1% agarose gel and visualized with ethidium bromide. Restriction digests from eight out of ten selected plaques are shown. DNA from a wild-type phage was included as a negative control, and uncut and cut DNA fragments are indicated with arrows.

Since many staphylococci lack native CRISPR-Cas systems (51), it was investigated whether a heterologous CRISPR-Cas10 system would enable access to phages that attack CRISPR-less hosts. To test this, the targeting and editing plasmids perispr-cas/spcϕ and perispr-cas/spcϕ-donor, respectively, were created. Both plasmids encode the *S. epidermidis* CRISPR-Cas10 system with deletions in cas1 and cas2, which are dispensable for immunity (52). These plasmids were introduced into *S. aureus* RN4220, which is naturally devoid of a CRISPR-Cas system. A similar two-step approach was used to test the efficiencies of targeting and editing of phage ISP, which also replicates on *S. aureus* (12). It was observed that similarly to anti-phage immunity in *S. epidermidis*, CRISPR-Cas10 affords robust protection against ISP when overexpressed in the *S. aureus* background (FIGS. 7 A and B). Co-culturing ISP with the editing strain thus enabled the recovery of numerous recombinant phages (FIGS. 7 C and D). Interestingly, the editing efficiency in *S. aureus* is 2-3 orders of magnitude lower than that observed in the native *S. epidermidis* background (Table 2), which could likely be due to differences in the homology-directed repair mechanisms in these two organisms. Nonetheless, the robust immunity mounted by CRISPR-Cas10 in this heterologous system effectively revealed the rare recombinants.

CRISPR-Cas10 Protospacers are Densely Packed Across Phage Genomes

The results obtained thus far show CRISPR-Cas10 can be used as a powerful tool for phage genome editing. However, protospacer selection for CRISPR-Cas10 interference is subjected to at least two constraints: targeted regions must be i) actively transcribed (39), and ii) harbour little or no complementarity between the antitag and the opposing 8-nucleotide tag on the 5'-end of crRNAs (45). Since staphylococcal phage genomes are densely packed with coding sequences (11), the former constraint is unlikely to constitute a severe limitation. However, it was investigated whether the requisite absence of complementarity between the crRNA 5'-tag and protospacer-adjacent antitag would limit access to significant regions of phage genomes. To test this, a Python script was developed to identify in a given gene all permissible 35-nucleotide protospacers that harboured zero complementarity between the protospacer adjacent antitag region and crRNA 5'-tag, which constitutes the strictest condition for a permissible protospacer. All twenty genes from Andhra and twenty genes from ISP (selected at random) were analyzed to identify all such protospacers that are predicted to be permissible for CRISPR-Cas10 interference. Strikingly, an average of 12.1±2.8 and 12.8±2.6 permissible protospacers were identified per 100 nucleotides of coding sequence in Andhra and ISP, respectively (Table 4). Notably, this value represents the minimum number of protospacers since some complementarity between the tag and antitag is tolerated (Table 1 and (45)).

To date, CRISPR-Cas10 has remained underexplored for genetic applications, likely owing to its remarkable complexity. The transcription dependence of this system, which provides a mechanism for temperate phages to evade immunity, calls into question the utility of CRISPR-Cas10 as an editing tool for other types of phages. This work presents the first systematic study of CRISPR-Cas10 immunity against virulent staphylococcal phages and demonstrates CRISPR-Cas10 effectively facilitates the recovery of rare phage recombinants containing desired mutations. The set of genetic tools described herein thus enables the systematic study of genes of unknown function in virulent staphylococcal phages through the introduction of point mutations and premature stop codons. Importantly, since many staphylococci naturally possess CRISPR-Cas10 systems, or can express a functional system on a plasmid, these tools can be applied to phages that infect diverse hosts. Given that phage genomes are replete with protospacers that are permissible for CRISPR-Cas10 targeting (Table 4), and editing can also be accomplished up to 470 nucleotides distal from the protospacer (FIG. 4), these tools enable virtually unrestricted access to the genome sequence space in virulent phages. To facilitate the implementation of this technique, the Python script that identifies all permissible CRISPR-Cas10 protospacers in a given gene and corresponding spacers to be cloned into targeting constructs has been made available at https://github com/ahatoum/CRISPR-Cas10-Protospacer-S elector.

Materials and Methods

Strains and growth conditions. *S. epidermidis* RP62a (53) and LAM104 (36) were grown in Brain Heart Infusion broth (BHI) (Difco). *S. aureus* RN4220 was grown in Tryptic Soy Broth (TSB) (Difco). Media were supplemented with the following antibiotics as needed: 10 μg/ml chloramphenicol (for selection of perispr and perispr-cas based plasmids) and 15 μg/mL neomycin (for selection of *S. epidermidis*). Phage Andhra was discovered in-house (43), and phage ISP was a generous gift from Luciano Marraffini. For phage propagation, *S. epidermidis* was grown in BHI plus 5 mM $CaCl_2$) to an early logarithmic phase at 37° C. with shaking. Phages were added at a multiplicity of infection (MOI) of 0.1 and incubated for an additional 6 hours at 37° C. The culture was pelleted at 8,000×g for 5 minutes and the supernatant was filtered through a 0.45 μm filter. Phages were enumerated by spotting 10-fold dilutions on Heart Infusion Agar (HIA) (Hardee Diagnostics) containing overnight cultures of *S. epidermidis* (1:100 dilution) and 5 mM $CaCl_2$) overlaid atop Tryptic Soy Agar (TSA) (Difco). High titer phage lysates were maintained at 4° C.

Spacer design. Spacers A1, A2, A5, A6, and I1-I3 (Table 1) were designed in accordance with the two criteria that are essential for the targeting of foreign DNA by the Type III-A CRISPR-Cas system (39, 45). Briefly, spacers were designed to target protospacer regions that bore little or no complementarity between the eight nucleotide tag on the 5'-end of the crRNA (5'-ACGAGAAC) and the corresponding "antitag" region adjacent to the protospacer, especially in the −4, −3, and −2 positions (5'-GAA). In addition, spacers were designed to encode crRNAs with base-pair complementary with the coding strand (as well as the corresponding mRNA.) As negative controls, spacers A3 and A4 were deliberately designed to defy the latter rule— these targeted the putative non-coding (template) strand. Nonetheless, spcA3 permitted efficient immunity, likely due to bi-directional transcription at the targeted locus (see main text for details).

Construction of *S. epidermidis* targeting strains. Spacers were introduced into targeting plasmids with inverse PCR using perispr (44) as template and the primers listed in Table 5. Following PCR, products were purified using the EZNA Cycle Pure Kit (Omega). Purified PCR products were 5' phosphorylated by T4 polynucleotide kinase (NEB) and circularized by T4 DNA ligase (NEB). Ligated constructs were first transformed intro *S. aureus* RN4220, a passage strain, via electroporation and selected on TSA supplemented with chloramphenicol. Several transformants were checked for the presence of appropriate spacer by colony PCR and subsequent sequencing of PCR products using primers A200 and F016 (Table 5). Confirmed perispr/spcϕ constructs were purified using the EZNA Plasmid Miniprep Kit (Omega) and transformed into *S. epidermidis* LAM104 for targeting experiments.

Construction of *S. epidermidis* editing strains. Donor plasmids perispr/spcA2-donor and perispr/spcA3-donor were created in two steps using Gibson assembly (54) and inverse PCR with primers indicated in Table 5. Briefly, Gibson assembly was first used to introduce wild-type phage-derived sequences into perispr/spcϕ constructs to make perispr/spcϕ-Andhra constructs. To do this, PCR products were generated using perispr/spcϕ constructs as templates for the backbone and phage genomic DNA as template for the inserts using primers N057-N060 (for perispr/spcA2-Andhra) and N124-N127 (for perispr/spcA3-Andhra). PCR products were purified as above and Gibson assembled. Assembled constructs were transformed into *S. aureus* RN4220 by electroporation. Transformants were confirmed for the presence of the phage-derived sequences by colony PCR and sequencing of PCR products using primers A200 and F016. In the second step, inverse PCR (as described above) was used to introduce silent mutations into confirmed perispr/spcϕ-Andhra constructs using primers NO55 and N056 (for perispr/spcA2-donor) and N144 and N145 (for perispr/spcA3-donor). To create donor plasmid perispr/spcI1-donor, a 3-part Gibson assembly was performed with perispr/spcI1 as template for the backbone, phage ISP DNA as template for the two inserts, and primers F316-F321 (Table 5). To create Andhra donor plasmids with varying homology arm lengths, plasmid perispr/spcA2-donor was used as a template to create plasmids perispr/spcA2-donor/250 and -donor/100 by Gibson assembly with primers N114-N117, and N118-N121, respectively (Table 5). Plasmid perispr/spcA2-donor/35 was created by inverse PCR using perispr/spcA2 as template and primers N061 and N062 (Table 5). Plasmid perispr/spcA2-donor/distal was created by a two-piece Gibson assembly using perispr/spcA2-donor as a template for the backbone, synthetic construct A454 (Invitrogen, FIG. 6) as template for the donor sequence, and primers N057-N060 (Table 5). All ligated/Gibson assembled donor plasmids were transformed first into *S. aureus* RN4220. Several transformants were checked for the presence of desired constructs using colony PCR and sequencing, and confirmed plasmids were purified and introduced into *S. epidermidis* LAM104 for editing experiments.

Construction of *S. aureus* targeting and editing strains. The perispr-cas/spc1 plasmid was constructed with Gibson assembly using primers listed in Table 5, which were used to combine the cas genes from perispr-cas/Δcas1Δcas2 (52) (PCR amplified with primers F065 and F066) with the single repeat-spacer unit and plasmid backbone of pGG3 (39) (PCR amplified with primers F064 and F067), thus generating a single repeat/spacer CRISPR array in a Δcas1/2 background. The perispr-cas/spcI1 targeting plasmid was created by Gibson assembly, which was used to assemble spcI1 from perispr/spcI1 (amplified with PCR primers F354 and F355) with the backbone of perispr-cas/spc1 (amplified with PCR primers F060 and F353). The perispr/spcI1-donor editing plasmid was created by Gibson assembly using the perispr-cas/spcI1 plasmid as backbone (amplified with primers F367 and F370) and the recovery sequence from perispr/spcI1 (amplified with primers F368 and F369). All assembled constructs were transformed into *S. aureus* RN4220 and their sequences were confirmed via colony PCR and sequencing with primers A405 and F064. *S. aureus* RN4220 strains with confirmed constructs were used in targeting and editing experiments.

Phage targeting and genome editing. To test the efficiency of targeting by perispr/spcϕ or perispr-cas/spcϕ plasmids, overnight cultures of targeting strains were diluted 1:40 in HIA top agar plus 5 mM $CaCl_2$). The mixture was overlaid atop a TSA plate containing 5 mM $CaCl_2$). After allowing the top agar to set (~10 min at room temperature), ten-fold serial dilutions of targeted phages were spotted on the top agar, and phage lysate drops were allowed to dry at room temperature ~15 min. Plates were incubated overnight at 37° C., and phage plaques were enumerated the following day. To test the efficiency of phage editing in the presence of various donor plasmids, editing strains were combined with their appropriate phages at MOI=1 and co-cultured for indicated times at 37° C. without shaking. As controls, corresponding targeting strains were also co-cultured under the same conditions. Phage-host mixtures were diluted 1:20 in HIA top agar plus 5 mM $CaCl_2$), and then overlaid atop TSA plates containing 5 mM $CaCl_2$). Top agar was allowed to set and plates were incubated overnight at 37° C. Plaques were enumerated the following day. All experiments were conducted in triplicate.

Genome extraction and confirmation of recombinant phages. To confirm the presence of desired mutations in putative recombinant phages, 20 plaques were selected from the phage-editing strain co-culture plates. Individual plaques were picked from the top agar, placed into 500 µl of TSB, and vortexed for 1 min to extract phages from plaques. Phages released into the supernatant were propagated by incubating with the corresponding targeting strains (1:100 dilution of overnight culture) for 6 hours in BHI plus 5 mM CaCl$_2$). Cells were pelleted, and phage lysates were passed through 0.45 µm filters. Filtered lysates were combined 1:1 with phenol, chloroform, isoamyl alcohol (25:24:1) and vortexed for one minute. Mixtures were centrifuged at 17,000×g for 5 minutes, and aqueous layers were recovered into a fresh tube. Aqueous layers were then mixed with 100% ethanol (2.5 vols) and 3.0 M Na-acetate pH 5.2 (1/10 vol). Samples were kept in ice for 10 minutes and centrifuged at 17,000×g for 5 min. DNA pellets were washed with 1 mL 75% ethanol and air dried for 10 min. Pellets were dissolved in 30 µl of distilled H$_2$O and used as templates for PCR amplification with primers N146 and N147 for Andhra or F317 and F319 for ISP (Table 5). Ten PCR products were subjected to digestion with appropriate restriction enzymes (as indicated in figure legends) and the remaining ten were sequenced using indicated primers (Table 5).

Python script for protospacer selection. A Python script (MainScript.py) was developed that takes a gene sequence (in 5'-3' direction) and crRNA 5'-tag (in 5'-3' direction) as user inputs, and as outputs, produces all possible 35-nucleotide protospacers that exhibit zero complementarity between the protospacer adjacent antitag region and the crRNA 5'-tag. The reverse complement of the tag is first obtained to generate an eight-nucleotide comparison template. Within a loop, a window of eight nucleotides that progressively moves rightward is copied from the gene sequence and compared to the template derived from the user's tag. In this comparison, when corresponding nucleotides are "not" equal to each other, a logic true is produced. Then the results of these Boolean comparisons are subjected to a logic AND operation among themselves, which yields true only when there is no match at any position between the nucleotides in the moving window and the comparison template. As the loop proceeds, each time the logic AND operation yields true, the beginning 5'-end coordinate of the moving window is recorded in an array with respect to the original gene sequence input, and a "possibility" counter is incremented by one. Each of these coordinates are required to be greater than 35 nucleotides into the gene (measuring from the 5'-end of the gene). Once this loop is completed, another loop begins, in which 35 nucleotides to the left of each recorded coordinate is extracted from the gene sequence—this is called the protospacer. The reverse complement of the protospacer is also generated as an output to indicate the corresponding spacer sequence that would need to be cloned into targeting and editing constructs. The Python source code and instructions to run the code are available at https://github.com/ahatoum/CRISPR-Cas10-Protospacer-Selector

TABLE 1

Spacers, crRNAs and cognate protospacer regions targeted in this study.

| Sequence[1] Position: | Tag-antitag[2] −8     −1 | Spacer-protospacer +1                                    +35 | Targeted Locus |
|---|---|---|---|
| spc1 | | ACGTATGCCGAAGTATATAAATCATCAGTACAAAG | pG0400 |
| crRNA | ACGAGAAC<br>    I I I | ACGUAUGCCGAAGUAUAUAAAUCAUCAGUACAAAG<br>IIIIIIIIIIIIIIIIIIIIIIIIIIIIIIIIIII | nes |
| ps | AAATCTCT | TGCATACGGCTTCATATATTTAGTAGTCATGTTTC | |
| spcA1 | | ATTGTAATTAATCAATAATTGTTGACAAGCAACTA | Andhra |
| crRNA | ACGAGAAC<br>   II  I  I | AUUGUAAUUAAUCAAUAAUUGUUGACAAGCAACUA<br>IIIIIIIIIIIIIIIIIIIIIIIIIIIIIIIIIII | ORF1<br>hypothetical |
| ps | TGACCAAG | TAACATTAATTAGTTATTAACAACTGTTCGTTGAT | |
| spcA2 | | AAAGATTGATTCTTATTAAATGCGTCTAATGGAAT | Andhra |
| crRNA | ACGAGAAC<br>       I | AAAGAUUGAUUCUUAUUAAAUGCGUCUAAUGGAAU<br>IIIIIIIIIIIIIIIIIIIIIIIIIIIIIIIIIII | ORF9<br>DNA |
| ps | TTAAAAGT | TTTCTAACTAAGAATAATTTACGCAGATTACCTTA | polymerase |
| spcA3 | | AAGAATTTCTCAAAAAATTACAAGACAGTATGCAG | Andhra |
| crRNA | ACGAGAAC | AAGAAUUUCUCAAAAAAUUACAAGACAGUAUGCAG<br>IIIIIIIIIIIIIIIIIIIIIIIIIIIIIIIIIII | ORF10<br>peptidase |
| ps | ACGGAAAC | TTCTTAAAGAGTTTTTAATGTTCTGTCATACGTC | |
| spcA4 | | ATTCCATTAGACGCATTTAATAAGAATCAATCTTT | Andhra |
| crRNA | ACGAGAAC<br>       I | AUUCCAUUAGACGCAUUUAAUAAGAAUCAAUCUUU<br>IIIIIIIIIIIIIIIIIIIIIIIIIIIIIIIIIII | ORF9<br>DNA |
| ps | CACGTCCA | TAAGGTAATCTGCGTAAATTATTCTTAGTTAGAAA | polymerase |
| spcA5 | | ATACTCATATTTGCATTTAATTCTCTTGATTTATT | Andhra |
| crRNA | ACGAGAAC<br>     I I | AUACUCAUAUUUGCAUUUAAUUCUCUUGAUUUAUU<br>IIIIIIIIIIIIIIIIIIIIIIIIIIIIIIIIIII | ORF19<br>hypothetical |
| ps | TACAAGGT | TATGAGTATAAACGTAAATTAAGAGAACTAAATAA | |
| spcA6 | | CAGGTTCAGTTACAACATCTTCTGCACTTTCAAT | Andhra |
| crRNA | ACGAGAAC | CAGGUUCAGUUACAACAUCUUCUGCACUUUCAAUU<br>IIIIIIIIIIIIIIIIIIIIIIIIIIIIIIIIIII | ORF20<br>hypothetical |
| ps | AAGAAAAA | GTCCAAGTCAATGTTGTAGAAGACGTGAAAGTTAA | |

TABLE 1 -continued

Spacers, crRNAs and cognate protospacer regions targeted in this study.

```
Sequence¹    Tag-antitag²            Spacer-protospacer                       Targeted
Position:    -8       -1     +1                                       +35     Locus spcI1                          TAACAGCTAGGTACCAACCTACTTTAGTATCCTG             ISP
crRNA        ACGAGAAC          UAACAGCUAGGUACCAACCUACUUUAGUAUCCUG             ORF61
                               IIIIIIIIIIIIIIIIIIIIIIIIIIIIIIIIII             DNA
ps           AAGAACCC          ATTGTCGATCCATGGTTGGATGAAATCATAGGAC             polymerase spcI2                          TATTCATGCTATTTCTCTCCTTTCAACTCTTTAA             ISP
crRNA        ACGAGAAC          UAUUCAUGCUAUUUCUCUCCUUUCAACUCUUUAA             ORFs
             I        I        IIIIIIIIIIIIIIIIIIIIIIIIIIIIIIIIII             121-122
ps           GGTCAATA          ATAAGTACGATAAAGAGAGGAAAGTTGAGAAATT             hypothetical spcI3                          TTGTTGTCCTGAAGAACGACCTGCATCGTTGTGTA            ISP
crRNA        ACGAGAAC          UUGUUGUCCUGAAGAACGACCUGCAUCGUUGUGUA            ORF 203
                               IIIIIIIIIIIIIIIIIIIIIIIIIIIIIIIIIII            endolysin
ps           AAGAGCAT          AACAACAGGACTTCTTGCTGGACGTAGCAACACAT
```

[1] Spacers (spc) and crresponding crRNAs are shown in the 5'-3' direction, and protospacer region (ps) are shown in the 5'-3' direction. Regions of complementarity are indicated with "I".
[2] CrRNA 5'-tag (red) and the regions adjacent to the protospacer that appear opposite to the tag (antitag, black) are shown.

The sequences in Table 1 correspond to SEQ ID NOs: 83-112 in the attached Sequence Listing.

TABLE 2

Phage editing efficiencies at different genetic loci

| Editing strain | Editing plasmid | Phage and locus | Editing efficiency[1] |
|---|---|---|---|
| S. epidermidis LAM104 | pcrispr/spcA2-donor | Andhra ORF 9 | 7.87 (±0.83) × $10^{-6}$ |
| S. epidermidis LAM104 | pcrispr/spcA3-donor | Andhra ORF 10 | 1.68 (±0.06) × $10^{-5}$ |
| S. epidermidis LAM104 | pcrispr/spcI1-donor | ISP ORF 61 | 1.36 (±0.31) × $10^{-5}$ |
| S. aureus RN4220 | pcrispr-cas/spcI1-donor | ISP ORF 61 | 6.67 (±1.52) × $10^{-8}$ |

[1] Editing efficiencies for 60-minute (S. epidermidis) or 90-minute (S. aureus) co-cultures of indicated editing strains and phages are shown. Efficiencies were calculated as the following ratio: pfu/ml observed on editing plate to pfu/ml added to the initial co-culture. An average of triplicate experiments (±S.D.) is shown.

TABLE 3

Positions of distal mutations acquired in Andhra phage variants

| Variant | -470 | -200 | -100 | 0 | +100 | +200 | +400 |
|---|---|---|---|---|---|---|---|
| K1 | − | − | + | + | + | + | − |
| K2 | − | + | + | + | + | + | − |
| K3 | − | + | + | + | + | − | − |
| K4 | + | + | + | + | + | + | + |
| K5 | + | + | + | + | + | + | − |
| K6 | − | − | − | + | − | − | − |
| K7 | − | + | + | + | + | + | + |
| K8 | − | − | + | + | + | + | − |
| K9 | − | − | − | + | + | + | + |
| K10 | − | − | − | + | − | − | − |
| K11 | + | + | + | + | + | + | + |
| K12 | − | − | − | + | + | + | − |
| K13 | − | + | + | + | + | + | − |
| K14 | − | − | + | + | + | + | − |
| K15 | − | + | + | + | + | + | + |
| K16 | − | + | + | + | + | − | − |
| K17 | − | − | − | + | + | + | + |
| K18 | − | − | + | + | − | − | − |
| K19 | − | + | + | + | + | + | + |
| K20 | − | + | + | + | + | + | + |
| K21 | − | − | − | + | + | − | − |
| K22 | − | − | − | + | + | + | − |
| K23 | − | − | − | + | + | + | − |
| K24 | − | − | − | + | + | + | − |
| K25 | − | + | + | + | + | + | − |
| K26 | − | − | − | + | − | − | − |
| K27 | − | − | − | + | + | − | − |
| K28 | − | + | + | + | + | + | − |
| K29 | − | − | − | + | − | − | − |
| K30 | − | − | − | + | − | − | − |
| K31 | − | − | + | + | − | − | − |
| Total[2] | 3 | 13 | 17 | 31 | 24 | 21 | 8 |

[1] The protospacer is located at position 0, and positions upstream and downstream of the protospacer are indicated with negative or positive numbers, respectively. Positions at which the mutation is present (+) or absent (−) for each variant are shown.
[2] The total number of variants that possess a mutation at each position is indicated.

TABLE 4

Permissible protospacers identified in Andhra and ISP genes

| Andhra | | | ISP | | |
|---|---|---|---|---|---|
| ORF[1] | Gene length (nucleotides) | Permissible protospacers[2] | ORF[1] | Gene length (nucleotides) | Permissible protospacers[2] |
| 1 | 241 | 16 | 27 | 2427 | 323 |
| 2 | 216 | 29 | 33 | 1047 | 137 |
| 3 | 510 | 67 | 40 | 1377 | 161 |

TABLE 4-continued

Permissible protospacers identified in Andhra and ISP genes

| | Andhra | | ISP | | |
|---|---|---|---|---|---|
| ORF[1] | Gene length (nucleotides) | Permissible protospacers[2] | ORF[1] | Gene length (nucleotides) | Permissible protospacers[2] |
| 4 | 210 | 20 | 44 | 1038 | 119 |
| 5 | 246 | 22 | 73 | 261 | 32 |
| 6 | 1212 | 163 | 84 | 444 | 58 |
| 7 | 504 | 87 | 88 | 243 | 32 |
| 8 | 1260 | 141 | 106 | 261 | 21 |
| 9 | 2292 | 263 | 119 | 1470 | 187 |
| 10 | 1422 | 171 | 128 | 168 | 19 |
| 11 | 411 | 43 | 147 | 237 | 29 |
| 12 | 1767 | 197 | 160 | 489 | 61 |
| 13 | 858 | 141 | 165 | 549 | 67 |
| 14 | 900 | 103 | 168 | 738 | 87 |
| 15 | 1830 | 215 | 176 | 165 | 16 |
| 16 | 720 | 103 | 177 | 276 | 59 |
| 17 | 1008 | 91 | 188 | 627 | 82 |
| 18 | 1218 | 138 | 197 | 693 | 104 |
| 19 | 192 | 23 | 204 | 504 | 76 |
| 20 | 324 | 57 | 208 | 333 | 42 |

[1]ORF, Open reading frame. Number appears as annotated in PubMed.
[2]A permissible protospacer is defined as a 35-nucleotide region complementary to the coding DNA strand that shares zero complementarity between the protospacer adjacent antitag region and the crRNA 5'-tag (ACGAGAAC).

TABLE 5

DNA oligonucleotides used in this study.

| Primer | Sequence (5'-3') | Purpose |
|---|---|---|
| N077 | TTGTTGACAAGCAACTAACGTATGCCGAAGTATATAAATCATCAG (SEQ ID NO: 9) | inverse PCR: pcrispr/spcA1 |
| N078 | TTATTGATTAATTACAATGTTCTCGTCCCCTTTTCTTCG (SEQ ID NO: 10) | |
| N043 | AATGCGTCTAATGGAATACGTATGCCGAAGTATATAAATCATCAG (SEQ ID NO: 11) | inverse PCR: pcrispr/spcA2 |
| N044 | TAATAAGAATCAATCTTTGTTCTCGTCCCCTTTTCTTCGG (SEQ ID NO: 12) | |
| N128 | TACAAGACAGTATGCAGACGTATGCCGAAGTATATAAATCATCAG (SEQ ID NO: 13) | inverse PCR: pcrispr/spcA3 |
| N129 | ATTTTTTGAGAAATTCTTGTTCTCGTCCCCTTTTCTTCG (SEQ ID NO: 14) | |
| N045 | AATAAGAATCAATCTTTACGTATGCCGAAGTATATAAATCATCAG (SEQ ID NO: 15) | Inverse PCR: pcrispr/spcA4 |
| N046 | AAATGCGTCTAATGGAATGTTCTCGTCCCCTTTTCTTCG (SEQ ID NO: 16) | |
| N100 | AATTCTCTTGATTTATTACGTATGCCGAAGTATATAAATCATCAG (SEQ ID NO: 17) | Inverse PCR: pcrispr/spcA5 |
| N101 | AAATGCAAATATGAGTATGTTCTCGTCCCCTTTTCTTCG (SEQ ID NO: 18) | |
| N098 | CTTCTGCACTTTCAATTACGTATGCCGAAGTATATAAATCATCAG (SEQ ID NO: 19) | Inverse PCR: pcrispr-spcA6 |
| N099 | ATGTTGTAACTGAACCTGGTTCTCGTCCCCTTTTCTTCG (SEQ ID NO: 20) | |
| A009 | GGATCCGAGCTCGGTACCAAGCTTC (SEQ ID NO: 21) | Inverse PCR: pcrispr/spcI1, /spcI2, and /spcI3 |
| F289 | CAGGATACTAAAGTAGGTTGGTACCTAGCTGTTAGTTCT | Inverse PCR: pcrispr/spcI1 |
| F288 | ATAAACGTTTAGATGCTTATGCAAAAGGAACAGTGTTCTCGTCCCCTTTTCTTCG (SEQ ID NO: 23) | Inverse PCR: pcrispr/spcI3 |
| F287 | TTAAAGAGTTGAAAGGAGAGAAATAGCATGAATAGTTCTCGTCCCCTTTTCTTCG (SEQ ID NO: 24) | Inverse PCR: pcrispr/spcI2 |
| N057 | ACCAAGCTTCTGAGGGGATAATATTATGTTTTTTAGTGGC (SEQ ID NO: 25) | Gibson assembly: pcrispr/spcA2-Andhra and pcrispr/spcA2- (SEQ ID donor/distal |
| N058 | CCTAAAAACCTACATTATGGATTCACCCTATAATTACACG (SEQ ID NO: 26) | |
| N059 | TCCATAATGTAGGTTTTTAGGCATAAAACTATATGATTTACCC (SEQ ID NO: 27) | |

TABLE 5-continued

DNA oligonucleotides used in this study.

| Primer | Sequence (5'-3') | Purpose |
|---|---|---|
| N060 | TATTATCCCCTCAGAAGCTTGGTACCGAGC (SEQ ID NO: 28) | |
| N055 | AAAGGCATCTAGTGGTATACCTG (SEQ ID NO: 29) | Inverse PCR: pcrispr/spcA2-donor |
| N056 | AACAAAAACCAATCATTTGAAAATTTTATTAAAAATG (SEQ ID NO: 30) | |
| F316 | CGGCCAAATACCATCCAACCTTTGTGTCTTGAATACTCTCAAAATCTTTAAAGTTTTCAG (SEQ ID NO: 31) | Gibson assembly: pcrispr/spcI1-donor |
| F317 | CCAAGCTTCTGTAGATAAAACTAAAAATACTATTAAAAAATGTTATGAGAAAAACG (SEQ ID NO: 32) | |
| F318 | CACAAAGGTTGGATGGTATTTGGCCGTAACCCAAGAAGTTAAAGAATCTTTAAGATTATC (SEQ ID NO: 33) | |
| F319 | GCCTAAAAACCTAAAAGTTACCTCCGTCAATATCATTAAC (SEQ ID NO: 34) | |
| F320 | GACGGAGGTAACTTTTAGGTTTTTAGGCATAAAACTATATGATTTACC (SEQ ID NO: 35) | |
| F321 | GTATTTTAGTTTTATCTACAGAAGCTTGGTACCGAGC (SEQ ID NO: 36) | |
| N114 | ACCAAGCTTCTGAAATGCGCCAACATCACTTTC (SEQ ID NO: 37) | Gibson assembly: pcrispr/spcA2-donr/250 |
| N115 | GCCTAAAAACCTATTATAATTTACTTGAACCATTAAAGTCTCTAACAC (SEQ ID NO: 38) | |
| N116 | GTAAATTATAATAGGTTTTTAGGCATAAAACTATATGATTTACCC (SEQ ID NO: 39) | |
| N117 | TTGGCGCATTTCAGAAGCTTGGTACCGAGC (SEQ ID NO: 40) | |
| N118 | CAAGCTTCTGTTTTGACGGGTAAATAGATATTGTTTTTGTTC (SEQ ID NO: 41) | Gibson assembly: pcrispr/spcA2-donor/100 |
| N119 | CCTAAAAACCTAGGATATAGAAAATCATGTCATTAAAAAATGTATGTAC (SEQ ID NO: 42) | |
| N120 | TTTCTATATCCTAGGTTTTTAGGCATAAAACTATATGATTTACCC (SEQ ID NO: 43) | |
| N121 | CCCGTCAAAACAGAAGCTTGGTACCGAGC (SEQ ID NO: 44) | |
| N061 | AAAGGCATCTAGTGGTATACCTGCACTGGCAATTTTAATTGTGTTATCTTCTTAGGTTTTTAGGCATAAAACTATATGATTTACC (SEQ ID NO: 45) | Inverse PCR: pcrispr/spcA2-donor/35 |
| N062 | AACAAAAACCAATCATTTGAAAATTTTATTAAAAATGATTTCACCATAAACAGAAGCTTGGTACCGAGC (SEQ ID NO: 46) | |
| N124 | ACCAAGCTTCTGCCGCATATGAAAAAAATGAGGGC (SEQ ID NO: 47) | Gibson assembly: pcrispr/spcA3-Andhra |
| N125 | GCCTAAAAACCTAAATTAGGTTTACTACTGAATCCATAGCC (SEQ ID NO: 48) | |
| N126 | AAACCTAATTTAGGTTTTTAGGCATAAAACTATATGATTTACCC (SEQ ID NO: 49) | |
| N127 | ATATGCGGCAGAAGCTTGGTACCGAGC (SEQ ID NO: 50) | |
| N144 | AGTTGCAGGATAGCATGCAATGGGATTTGCACTC (SEQ ID NO: 51) | Inverse PCR: pcrispr/spcA3-donor |
| N145 | TCTTAAGGAACTCCTCAAAGGCACGTGCCAC (SEQ ID NO: 52) | |
| N146 | ACCTAATTACCTACAAGCGATGTTAC (SEQ ID NO: 53) | PCR and sequence confirmation of recombinant phages (Andhra) |
| N147 | CGTGATGAGGACGGTTTTTTAG (SEQ ID NO: 54) | |
| A200 | TTGTCAAAAAAGTGACATATCATATAATCTTGTAC (SEQ ID NO: 55) | PCR and sequence confirmation of pcrispr based constructs |
| F016 | ACTGTACTTTTTACAGTCGGTTTTCTAATG (SEQ ID NO: 56) | |
| F064 | CCCCTAGAAATTAATCAATGCGTATTTTATTCAAAATCTAC (SEQ ID NO: 57) | Gibson assembly and inverse PCR: pcrispr-cas/spcI |
| F065 | GATTTTGAATAAAATACGCATTGATTAATTTCTAGGGGATGG (SEQ ID NO: 58) | |
| F066 | GCACCGAGATTATCTATATCGGCACGTACCACG (SEQ ID NO: 59) | |
| F067 | GGTACGTGCCGATATAGATAATCTCGGTGCTAC (SEQ ID NO: 60) | |

TABLE 5 -continued

DNA oligonucleotides used in this study.

| Primer | Sequence (5'-3') | Purpose |
|---|---|---|
| F317 | CCAAGCTTCTGTAGATAAAACTAAAAATACTATTAAAAAATGTTATGAGAAAAACG (SEQ ID NO: 61) | PCR and sequence confirmation of recombinant phages (ISP) |
| F319 | GCCTAAAAACCTAAAAGTTACCTCCGTCAATATCATTAAC (SEQ ID NO: 62) | |
| F060 | AATTTAACCTTTCATTTCTTTTTATATTTCGAATAAAAATTAGAC (SEQ ID NO: 63) | Gibson assembly: pcrispr-cas/spcI1 |
| F353 | CTTTAGTATCCTGTAAATCTAACAACACTCTAAAAAATTGTAGATTTTG (SEQ ID NO: 64) | |
| F354 | GAGTGTTGTTAGATTTACAGGATACTAAAGTAGGTTGGTACC (SEQ ID NO: 65) | |
| F355 | CGAAATATAAAAAGAAATGAAAGGTTAAATTAATATTAATTTTATTAAATG (SEQ ID NO: 66) | |
| F367 | CAGTAGTAGAACTAGAGTAAAGGTGATTTGTCACTATTTTTGAC (SEQ ID NO: 67) | Gibson assembly: pcrispr-cas/spcI1-donor |
| F368 | GACAAATCACCTTTACTCTAGTTCTACTACTGTTTCATTTAATTTATTCTCTAAC (SEQ ID NO: 68) | |
| F369 | GCGTCTATACCATCCTGATTATACTAAACCTTTAGAAATAAAATG (SEQ ID NO: 69) | |
| F370 | GTTTAGTATAATCAGGATGGTATAGACGCTAAATGTCACATTTTTTGACAAC (SEQ ID NO: 70) | |
| F017 | TTTAGTTGTCAAAAAATGTGACATTTAGCG (SEQ ID NO: 71) | PCR and sequence confirmation of pcrispr-cas/spcI1-donor |
| F358 | GTATTTTTAGTTTTATCTAGAACAAGAAAAAAGAGAAATTAATCACAAAATG (SEQ ID NO: 72) | |
| A405 | AATAATGTATTTACGCTGGGGC (SEQ ID NO: 73) | PCR and sequence confirmation of perispr-cas/spc1 and spcI1 |
| F064 | CCCCTAGAAATTAATCAATGCGTATTTTATTCAAAATCTAC (SEQ ID NO: 74) | |

References Cited in This Example
1. Iwase, T., Uehara, Y., Shinji, H., Tajima, A., Seo, H., Takada, K., Agata, T. and Mizunoe, Y. (2010) *Staphylococcus epidermidis* Esp inhibits *Staphylococcus aureus* biofilm formation and nasal colonization. Nature, 465, 346-349.
2. Cogen, A. L., Yamasaki, K., Sanchez, K. M., Dorschner, R. A., Lai, Y., MacLeod, D. T., Torpey, J. W., Otto, M., Nizet, V., Kim, J. E., et al. (2010) Selective antimicrobial action is provided by phenol-soluble modulins derived from *Staphylococcus epidermidis*, a normal resident of the skin. *J. Invest. Dermatol.*, 130, 192-200.
3. Lai, Y., Cogen, A. L., Radek, K. a, Park, H. J., Daniel, T., Leichtle, A., Ryan, A. F., Nardo, A. Di and Gallo, R. L. (2010) Activation of TLR2 by a Small Molecule Produced by *Staphylococcus epidermidis* Increases Antimicrobial Defense against Bacterial Skin Infections. 130, 2211-2221.
4. Naik, S., Bouladoux, N., Linehan, J. L., Han, S.-J., Harrison, O. J., Wilhelm, C., Conlan, S., Himmelfarb, S., Byrd, A. L., Deming, C., et al. (2015) Commensal-dendritic-cell interaction specifies a unique protective skin immune signature. *Nature*, 520, 104-108.
5. Otto, M. (2009) *Staphylococcus epidermidis*—the 'accidental' pathogen. *Nat. Rev. Microbiol.*, 7,555-567.
6. Lowy, F. D. (1998) *Staphylococcus aureus* infections. *N. Engl. J. Med.*, 339, 520-532.
7. Kluytmans, J., Belkum, A. van and Verbrugh, H. (1997) Nasal Carriage of *Staphylococcus aureus*: Epidemiology, Underlying Mechanisms, and Associated Risks. *Clin. Microbiol. Rev.*, 10, 505-520.
8. Stryjewski, M. E. and Chambers, H. F. (2008) Skin and Soft-Tissue Infections Caused by *Staphylococcus aureus*. *Clin. Infect. Dis.*, 46, S368-377.
9. Grice, E. A. and Segre, J. A. (2011) The skin microbiome. *Nat. Rev. Microbiol.*, 9, 244-253.
10. Flores, C. O., Meyer, J. R., Valverde, S., Farr, L. and Weitz, J. S. (2011) Statistical structure of host phage interactions. *Proc. Natl. Acad. Sci.*, 108, E288.
11. Deghorain, M. and Van Melderen, L. (2012) The staphylococci phages family: An overview. *Viruses*, 4, 3316-3335.
12. Kwan, T., Liu, J., DuBow, M., Gros, P. and Pelletier, J. (2005) The complete genomes and proteomes of 27 *Staphylococcus aureus* bacteriophages. *Proc. Natl. Acad. Sci. U.S.A*, 102, 5174-9.
13. Brüssow, H., Canchaya, C., Hardt, W. and Bru, H. (2004) Phages and the Evolution of Bacterial Pathogens: from Genomic Rearrangements to Lysogenic Conversion. *Microbiol. Mol. Biol. Rev.*, 68, 560-602.
14. Tormo, M. Á., Ferrer, M. D., Maiques, E., Úbeda, C., Selva, L., Lasa, Í., Calvete, J. J., Novick, R. P. and Penadés, J. R. (2008) *Staphylococcus aureus* Pathogenicity Island DNA Is Packaged in Particles Composed of Phage Proteins. *J. Bacteriol.*, 190, 2434-2440.
15. Borysowski, J., Łobocka, M., Międzybrodzki, R., Weber-Dąbrowska, B. and Górski, A. (2011) Potential of Bacteriophages and Their Lysins in the Treatment of MRSA. *Biodrugs*, 25, 347-355.
16. Kaźmierczak, Z., Górski, A. and Dąbrowska, K. (2014) Facing Antibiotic Resistance: *Staphylococcus aureus* Phages as a Medical Tool. *Viruses*, 6, 2551-2570.
17. Uchiyama, J., Takemura-Uchiyama, I., Sakaguchi, Y., Gamoh, K., Kato, S.-I., Daibata, M., Ujihara, T., Misawa, N. and Matsuzaki, S. (2014) Intragenus generalized transduction in *Staphylococcus* spp. by a novel giant phage. *ISME 1*, 8, 1-4.

18. Keen, E. C., Bliskovsky, V. V., Malagon, F., Baker, J. D., Prince, J. S., Klaus, J. S. and Adhya, S. L. (2017) Novel 'Superspreader' Bacteriophages Promote Horizontal Gene Transfer by Transformation. *MBio*, 8, 1-12.
19. Fernández, L., González, S., Campelo, A. B., Martinez, B. and Rodriguez, A. (2017) Low-level predation by lytic phage phiIPLA-RODI promotes biofilm formation and triggers the stringent response in *Staphylococcus aureus*. *Sci. Rep.*, 7,1-14.
20. Górski, A., Międzybrodzki, R., Borysowski, J., Dąbrowska, K., Wierzbicki, P., Ohams, M., Korczak-Kowalska, G., Olszowska-Zaremba, N., Łusiak-Szelachowska, M., KŁak, M., et al. (2012) Phage as a Modulator of Immune Responses: Practical Implications for Phage Therapy. *Adv. Virus Res.*, 83, 41-71.
21. Cooper, C. J., Mirzaei, M. K. and Nilsson, A. S. (2016) Adapting Drug Approval Pathways for Bacteriophage-Based Therapeutics. *Front. Microbiol.*, 7, 1-15.
22. Pires, D. P., Cleto, S., Sillankorva, S., Azeredo, J. and Lu, T. K. (2016) Genetically Engineered Phages: a Review of Advances over the Last Decade. *Microbiol. Mol. Biol. Rev.*, 80, 523-543.
23. Loessner, M. J., Rees, C. E. D., Stewart, G. S. A. B. and Scherer, S. (1996) Construction of luciferase reporter bacteriophage A511::luxAB for rapid and sensitive detection of viable *Listeria* cells. These include: Construction of Luciferase Reporter Bacteriophage A511::luxAB for Rapid and Sensitive Detection of Viable Lister. *Appl. Environ. Microbiol.*, 62, 1133-1140.
24. Marinelli, L. J., Piuri, M., Swigoňiová, Z., Balachandran, A., Oldfield, L. M., Kessel, J. C. van and Hatfull, G. F. (2008) BRED: A Simple and Powerful Tool for Constructing Mutant and Recombinant Bacteriophage Genomes. *PLoS One*, 3, e3957.
25. Ando, H., Lemire, S., Pires, D. P. and Lu, T. K. (2015) Engineering Modular Viral Scaffolds for Targeted Bacterial Population Editing. *Cell Syst.*, 1, 187-196.
26. Monk, I. R., Shah, I. M., Xu, M., Tan, M.-W. and Foster, T. J. (2012) Transforming the Untransformable: Application of Direct Transformation To Manipulate Genetically *Staphylococcus aureus* and *Staphylococcus epidermidis*. *MBio*, 3, e00277-11.
27. Kiro, R., Shitrit, D. and Qimron, U. (2014) Efficient engineering of a bacteriophage genome using the type I-E CRISPR-Cas system. *RNA Biol.*, 11, 42-4.
28. Martel, B. and Moineau, S. (2014) CRISPR-Cas: An efficient tool for genome engineering of virulent bacteriophages. *Nucleic Acids Res.*, 42, 9504-9513.
29. Box, A. M., McGuffie, M. J., O'Hara, B. J. and Seed, K. D. (2016) Functional Analysis of Bacteriophage Immunity through a Type I-E CRISPR-Cas System in *Vibrio cholerae* and Its Application in Bacteriophage Genome Engineering. *J. Bacteriol.*, 198, 578-590.
30. Lemay, M.-L., Tremblay, D. M. and Moineau, S. (2017) Genome Engineering of Virulent Lactococcal Phages Using CRISPR-Cas9. *ACS Synth. Biol.*, doi: 10.10.
31. Godde, J. S. and Bickerton, A. (2006) The repetitive DNA elements called CRISPRs and their associated genes: Evidence of horizontal transfer among prokaryotes. *J. Mol. Evol.*, 62, 718-729.
32. Grissa, I., Vergnaud, G. and Pourcel, C. (2007) The CRISPRdb database and tools to display CRISPRs and to generate dictionaries of spacers and repeats. *BMC Bioinformatics*, 8, 172.
33. Haft, D. H., Selengut, J., Mongodin, E. F. and Nelson, K. E. (2005) A guild of 45 CRISPR-associated (Cas) protein families and multiple CRISPR/cas subtypes exist in prokaryotic genomes. *PLoS Comput. Biol.*, 1, 0474-0483.
34. Barrangou, R., Fremaux, C., Deveau, H., Richards, M., Boyaval, P., Moineau, S., Romero, D. A. and Horvath, P. (2007) CRISPR provides acquired resistance against viruses in prokaryotes. *Science*, 315, 1709-1712.
35. Brouns, S. J. J., Jore, M. M., Lundgren, M., Westra, E. R., Slijkhuis, R. J. H., Snijders, A. P. L., Dickman, M. J., Makarova, K. S., Koonin, E. V and van der Oost, J. (2008) Small CRISPR RNAs guide antiviral defense in prokaryotes. *Science*, 321, 960-4.
36. Marraffini, L. A. and Sontheimer, E. J. (2008) CRISPR interference limits horizontal gene transfer in staphylococci by targeting DNA. *Science*, 322, 1843-1845.
37. Makarova, K. S., Wolf, Y. I., Alkhnbashi, O. S., Costa, F., Shah, S. A., Saunders, S. J., Barrangou, R., Brouns, S. J. J., Charpentier, E., Haft, D. H., et al. (2015) An updated evolutionary classification of CRISPR-Cas systems. *Nat. Rev. Microbiol.*, 13, 722-736.
38. Koonin, E. V, Makarova, K. S. and Zhang, F. (2017) Diversity, classification and evolution of CRISPR-Cas systems. *Curr. Opin. Microbiol.*, 37, 67-78.
39. Goldberg, G. W., Jiang, W., Bikard, D. and Marraffini, L. A. (2014) Conditional tolerance of temperate phages via transcription-dependent CRISPR-Cas targeting. *Nature*, 514, 633-637.
40. Maniv, I., Jiang, W., Bikard, D. and Marraffini, L. A. (2016) Impact of different target sequences on type III CRISPR-Cas immunity. *J. Bacteriol.*, 198, 941-950.
41. Hatoum-Aslan, A., Samai, P., Maniv, I., Jiang, W. and Marraffini, L. A. (2013) A ruler protein in a complex for antiviral defense determines the length of small interfering CRISPR RNAs. *J. Biol. Chem.*, 288, 27888-27897.
42. Samai, P., Pyenson, N., Jiang, W., Goldberg, G. W., Hatoum-Aslan, A. and Marraffini, L. A. (2015) Co-transcriptional DNA and RNA cleavage during type III CRISPR-cas immunity. *Cell*, 161, 1164-1174.
43. Cater, K., Dandu, V. S., Bari, S. M. N., Lackey, K., Everett, G. F. K. and Hatoum-Aslan, A. (2017) A Novel *Staphylococcus* Podophage Encodes a Unique Lysin with Unusual Modular Design. *mSphere*, 2, 1-9.
44. Hatoum-Aslan, A., Maniv, I. and Marraffini, L. A. (2011) Mature clustered, regularly interspaced, short palindromic repeats RNA (crRNA) length is measured by a ruler mechanism anchored at the precursor processing site. *Proc. Natl. Acad. Sci.*, 108, 21218-21222.
45. Marraffini, L. A. and Sontheimer, E. J. (2010) Self vs. non-self discrimination during CRISPR RNA-directed immunity. *Nature*, 463, 568-571.
46. Deveau, H., Barrangou, R., Garneau, J. E., Labonté, J., Fremaux, C., Boyaval, P., Romero, D. A., Horvath, P. and Moineau, S. (2008) Phage Response to CRISPR-Encoded Resistance in *Streptococcus thermophilus*. *J. Bacteriol.*, 190, 1390-1400.
47. Semenova, E., Jore, M. M., Datsenko, K. A., Semenova, A., Westra, E. R., Wanner, B., van der Oost, J., Brouns, S. J. J. and Severinov, K. (2011) Interference by clustered regularly interspaced short palindromic repeat (CRISPR) RNA is governed by a seed sequence. *Proc. Natl. Acad. Sci.*, 108, 10098-10103.
48. Wiedenheft, B., Duijn, E. van, Bultema, J. B., Waghmare, S., Zhou, K., Barendregt, A., Westphal, W., Heck, A. J. R., Boekema, E. J., Dickman, M. J., et al. (2011) RNA-guided complex from a bacterial immune system enhances target recognition through seed sequence interactions. *Proc. Natl. Acad. Sci.*, 108, 10092-10097.

49. Jiang, W., Bikard, D., Cox, D., Zhang, F. and Marraffini, L. A. (2013) CRISPR-assisted editing of bacterial genomes. *Nat. Biotechnol.,* 31, 233-239.
50. Mojica, F. J. M., Diez-Villaseñor, C., García-Martínez, J. and Almendros, C. (2009) Short motif sequences determine the targets of the prokaryotic CRISPR defence system. *Microbiology,* 155, 733-740.
51. Hatoum-Aslan, A. and Marraffini, L. A. (2014) Impact of CRISPR immunity on the emergence and virulence of bacterial pathogens. *Curr. Opin. Microbiol.,* 17, 82-90.
52. Hatoum-Aslan, A., Maniv, I., Samai, P. and Marraffini, L. A. (2014) Genetic characterization of antiplasmid immunity through a type III-A CRISPR-cas system. *J. Bacteriol.,* 196, 310-317.
53. Gill, S. R., Fouts, D. E., Archer, G. L., Mongodin, E. F., DeBoy, R. T., Ravel, J., Paulsen, I. T., Kolonay, J. F., Brinkac, L., Beanan, M., et al. (2005) Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidermidis* Strain. *J. Bacteriol.,* 187, 2426-2438.
54. Gibson, D. G., Young, L., Chuang, R.-Y., Venter, J. C., Hutchison, C. A. and Smith, H. O. (2009) Enzymatic assembly of DNA molecules up to several hundred kilobases. *Nat Meth,* 6, 343-345.

Example 2. Identification of Genes Responsible for Host Specificity

Phages are generally restricted to a single host or subset of related hosts within the same genus. Known staphylococcal phages can exhibit restricted, strain-specific or expansive, inter-species host ranges. Little is known about the phage protein(s) that bind the cell wall of these organisms and dictate host specificity.

The discovery of phages with host ranges that are mutually exclusive (Andhra (V2) vs. NB) and overlapping (J1 vs. MH/SS, FIGS. 4 and 9) is shown in Table 6.

TABLE 6

Host ranges of indicated phages expressed in PFUs (±S.D) when plated on the indicated bacterial strain

| Bacterial Strain | podophage Andhra (V2) | podophage NB | myophage J1 | myophage MH/SS |
|---|---|---|---|---|
| *S. epidermidis* RP62a | 6.8 (±3.4) × $10^7$ | 0 | 1.3 (±0.5) × $10^8$ | 2.5 (±0.6) × $10^8$ |
| *S. epidermidis* 1457 | 0 | 0 | 0 | 4.3 (±3.3) × $10^8$ |
| *S. epidermidis* ATCC12228 | 0 | 0 | 0 | 2.6 (±1.4) × $10^6$ |
| *S. aureus* ST398 | 0 | 3.7 (±0.6) × $10^8$ | 7.3 (±3.8) × $10^8$ | 0 |
| *S. aureus* RN4220 | 0 | 5.7 (±0.6) × $10^5$ | 2.3 (±1.2) × $10^8$ | 0 |
| *S. aureus* Newman | 0 | 9.3 (±1.1) × $10^5$ | 2.8 (±0.5) × $10^7$ | 0 |

*An average of triplicate measurements is shown.

While Andhra (V2) and NB share little sequence homology, the order of predicted genes remains conserved. A recent report on a *S. aureus* podophage closely related to NB identified the minor tail protein as its putative host specificity factor. Further disclosed in this example, is a system that is used to swap the minor tail protein of Andhra (V2) with that of NB. To do this, a *S. epidermidis* RP62a editing strain is constructed that contains two plasmids:

1. perispr-rescue$^{spc1/2}$ harbors a crRNA targeting the minor tail protein of V2, and a "rescue" sequence containing silent mutations.
2. pNBtail contains the minor tail protein of NB as an alternative "rescue" sequence.

Co-culture of this editing strain with V2 forces the phage to recombine with one of the rescue sequences. The resulting recombinants are plated on (a) *S. epidermidis* RP62a and (b) *S. aureus* ST398 strains to detect recombinant phages that have (a) incorporated the silent mutations, or (b) incorporated the alternate tail protein. The silent mutations serve as an internal control to measure recombination efficiency. Since staphylococcal plasmids can be readily shared between members of the same genus, and even with members of *Bacillus*, it is safe to assume that once inside the non-native staphylococcal host, recombinant phages can complete their life cycle and form plaques. Plaqueing on the *S. aureus* strain 1) indicates that the targeted protein is responsible for host specificity, and 2) creates a podophage with an altered host range.

A similar host-swap approach is used to identify the host specificity factor(s) of myophages J1 and MH/SS. Since the genetic determinants for host specificity in *Staphylococcus* myophages remain unknown, tail proteins are used as starting points for the swap. Myophage MH/SS genome is sequenced. Tail proteins are systematically swapped with those of J1, and resulting MH/SS recombinants are plated on both *S. epidermidis* and *S. aureus* as described above to screen for hybrid MH/SS phages that have an expanded host range. Further, MH/SS exhibits a broader host range within *S. epidermidis* strains, and this approach can be used in reverse to understand the genetic determinants for plaqueing on other *S. epidermidis* strains by engineering phage J1 to acquire this broader range.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

Sequences

*Staphylococcus epidermidis* RP62a Accession number: NC_002976

CRISPR-Associated Gene Locus Tags:
cas10/csm1—"SE2461"
csm2—"SE2460"
csm3—"SE2459"
csm4—"SE2458"
csm5—"SE2457"

csm6—"SE2456"
cas6—"SE2455"
CRISPR-Associated Protein IDs:
Cas10/Csm1—"WP_002486045.1"
Csm2—"WP 002486044.1"
Csm3—"WP 002486018.1"
Csm4—"WP 002486041.1"
Csm5—"WP 002486031.1"
Csm6—"WP 002486034.1"
Cas6—"WP 002486027.1"
Vector Insert Sequence:

Key: Note the underlined ATG sequences provide the start for the cas10/csm1, c5m2, c5m3, c5m4, c5m5, c5m6, and ca56 coding sequences, respectively.
(SEQ ID NO: 1)

ATCTTTATATAAATGGAGGTTAAAATGAATAAAAAAAATATATTAATGTATGGCTCTTTATTACATGATATAGGGAA

AATTATATATCGAAGTGGTGATCATACATTTTCAAGAGGTACGCATTCAAAATTAGGTCATCAATTTTTGTCCCAAT

TTTCAGAATTTAAAGACAACGAAGTGCTTGATAACGTTGCTTATCATCATTACAAAGAACTCGCAAAAGCTAATTTA

GATAATGATAATACAGCTTATATTACCTATATTGCGGATAATATTGCGAGTGGTATTGATAGAAGAGATATTATAG

AAGAAGGCGATGAAGAATACGAAAAACAACTATTTAATTTTGATAAATATACACCGCTATATAGTGTGTTTAATAT

TGTGAATTCTGAAAAATTGAAACAAACAAACGGGAAGTTTAAATTTTCTAATGAAAGTAATATTGAATATCCTAAA

ACTGAAAACATTCAATATTCAAGTGGAAATTATACAACATTAATGAAAGATATGAGTCATGATTTAGAGCACAAAT

TAAGTATTAAAGAAGGTACATTTCCTTCATTATTACAATGGACGGAAAGTCTATGGCAATATGTACCTAGTTCGAC

AAATAAAAACCAATTAATTGATATTTCTCTTTATGATCATAGTCGTATTACATGTGCCATCGCCAGTTGTATATTTGA

TTATTTAAATGAAAATAACATACATAATTACAAAGATGAATTGTTCTCAAAGTATGAAAATACCAAATCATTTTATC

AAAAAGAAGCTTTTTTACTACTTAGTATGGATATGAGTGGTATTCAAGATTTTATTTACAATATAAGCGGTTCTAAA

GCATTAAAGAGTCTAAGATCTCGTAGTTTTTATTTAGAACTCATGCTTGAAGTAATCGTTGATCAATTATTAGAAAG

ATTAGAATTAGCACGAGCAAATCTTTTGTATACAGGTGGTGGCCATGCTTATTTATTAGTGTCTAATACTGATAAAG

TGAAGAAAAAATAACTCAATTTAATAATGAATTAAAAAAATGGTTTATGTCAGAATTTACTACAGATCTTTCATTA

TCAATGGCTTTTGAAAAATGTAGTGGCGATGATTTAATGAATACAAGTGGTAATTATAGAACTATTTGGCGTAATG

TTAGCAGCAAACTTTCTGATATTAAAGCGCATAAATATTCCGCGGAAGATATATTAAAATTAAATCATTTTCATTCG

TATGGAGATCGGGAATGTAAAGAATGTTTAAGAAGTGACATAGATATTAATGATGATGGACTATGTAGTATATGT

GAAGGAATTATTAATATATCAAATGATTTAAGAGATAAATCATTCTTTGTACTGTCAGAAACTGGAAAATTAAAAA

TGCCATTCAATAAATTTATATCGGTTATTGATTATGAAGAGGCAGAAATGTTAGTACAAAATAATAATCAAGTTCGT

ATTTACAGTAAAAATAAACCATATATAGGCATAGGAATATCAACAAATTTATGGATGTGTGATTACGACTATGCTA

GTCAAAATCAAGATATGAGAGAAAAAGGTATTGGAAGTTATGTAGATAGAGAAGAAGGGGTTAAGCGTTTAGGC

GTGGTACGTGCCGATATAGATAATCTCGGTGCTACATTTATATCTGGAATTCCAGAAAAATATAATTCAATTTCAAG

AACAGCTACATTGTCTCGTCAATTATCATTATTTTTTAAATACGAATTAAATCATTTATTAGAAAATTATCAAATTAC

TGCTATATATTCAGGCGGTGACGATTTATTTTTAATCGGTGCATGGGATGACATTATAGAAGCAAGCATTTATATA

AATGACAAATTTAAAGAGTTTACTCTTGATAAACTAACATTGTCTGCCGGGGTTGGAATGTTTAGTGGTAAGTACC

CAGTTTCTAAAATGGCTTTTGAGACAGGACGACTTGAAGAAGCGGCTAAGACTGGTGAAAAAAATCAGATATCTC

TTTGGTTACAAGAAAAGTATATAACTGGGATGAGTTTAAAAAGAATATCTTAGAAGAAAAACTTCTCGTTTTACA

ACAGGGGTTTTCTCAAACAGATGAACACGGGAAAGCCTTCATTTATAAAATGCTCGCTTTACTGAGAAATAATGAA

GCTATTAATATTGCTCGTTTAGCTTACTTATTAGCAAGAAGCAAGATGAATGAGGATTTTACGTCTAAAATTTTTAA

TTGGGCTCAAAACGACAAAGATAAAAATCAATTAATTACAGCGTTAGAGTATTATATTTATCAAATAAGGGAGGCT

GATTGAGTATGATATTAGCTAAAACTAAAAGTGGTAAAACGATAGATTTGACTTTTGCACATGAGGTCGTAAAAAG

TAATGTAAAAAATGTTAAAGATAGAAAAGGCAAAGAAAAACAAGTTTTATTTAACGGGCTTACAACAAGCAAGTT

AAGAAATTTAATGGAGCAGGTAAATAGACTTTATACTATTGCATTTAATTCGAATGAGGATCAATTGAATGAAGAA

TTCATTGATGAATTAGAATATTTAAAAATTAAATTTTATTATGAAGCAGGACGAGAAAAAAGCGTTGATGAATTTTT

AAAAAAAACATTGATGTTTCCAATTATTGATAGAGTGATAAAAAAAGAATCAAAAAAATTTTTCTTAGATTATTGTA

-continued

```
AATACTTTGAAGCTTTAGTTGCATACGCTAAATATTATCAAAAGGAGGATTAATATGTATTCAAAAATTAAAATTTC
AGGAACAATTGAAGTAGTTACTGGTTTACACATCGGCGGAGGCGGTGAATCTAGTATGATTGGAGCAATTGATTC
TCCTGTAGTTAGAGATTTGCAAACCAAATTACCTATCATACCTGGCAGTTCAATCAAAGGAAAAATGAGAAATTTA
TTAGCAAAACATTTTGGCTTGAAAATGAAACAAGAGAGTCATAACCAAGATGATGAACGTGTATTAAGATTATTTG
GCTCAAGTGAAAAGGAAATATCCAAAGAGCTCGTCTACAAATTTCTGATGCATTCTTTTCTGAAAAGACAAAAGA
GCATTTTGCGCAAAATGATATTGCCTATACAGAAACGAAATTTGAGAATACAATTAATCGTTTAACTGCAGTTGCA
AACCCAAGACAAATTGAAAGAGTAACAAGAGGATCTGAGTTTGACTTTGTATTTATTTACAATGTCGATGAAGAGT
CGCAAGTTGAGGATGATTTTGAGAATATTGAAAAAGCGATTCACTTATTAGAGAATGACTATCTTGGTGGCGGCG
GAACTAGAGGTAACGGACGTATTCAATTTAAAGATACAAATATCGAGACAGTTGTTGGAGAATACGATAGTACAA
ATCTTAAAATTAAGTAGGTGAATGACATTGGCAACAAAAGTATTTAAACTTTCTTTTAAGACTCCTGTTCATTTTGG
AAAAAAACGGTTGTCAGATGGTGAAATGACAATCACTGCTGATACTTTGTTTAGTGCTTTATTTATTGAAACACTTC
AATTGGGTAAAGATACCGATTGGTTATTAAATGATTTAATCATTAGTGATACATTTCCTTATGAGAATGAGCTTTAT
TATCTTCCTAAACCTTTGATAAAAATTGACTCTAAAGAAGAAGATAACCATAAAGCATTTAAAAAGTTAAAATATGT
TCCGGTTCATCACTATAATCAATATTTAAATGGAGAGTTAAGCGCTGAAGATGCGACAGATTTAAATGATATTTTTA
ATATTGGGTATTTTTCTCTACAAACAAAGGTTTCATTAATAGCACAAGAAACTGATTCAAGTGCTGATAGTGAACCT
TATTCAGTGGGAACATTTACTTTTGAACCTGAAGCGGGTTTATATTTTATTGCAAAAGGATCAGAAGAAACGCTTG
ACCATTTAAATAATATTATGACTGCATTACAGTATTCAGGTTTAGGTGGTAAACGTAATGCAGGATACGGACAATT
TGAATATGAAATAATAAATAATCAACAACTATCTAAGTTACTGAATCAAAATGGAAAACATTCTATTCTTTTATCAA
CGGCAATGGCTAAAAAGAAGAGATAGAGAGTGCTTTAAAAGAGGCGAGATACATTTTAACTAAACGTTCTGGTT
TCGTACAATCAACGAATTATTCTGAAATGCTAGTTAAAAAAAGTGATTTCTATAGCTTTTCTTCGGGTTCAGTTTTTA
AAAATATCTTTAATGGTGATATTTTTAATGTTGGCCATAATGGTAAACACCCAGTCTATCGCTATGCAAAACCTTTA
TGGTTGGAGGTATAAGTATGACAATAAAAAATTATGAAGTCGTTATTAAAACTTTAGGTCCAATTCATATTGGTAG
TGGTCAAGTTATGAAGAAGCAAGATTACATTTATGACTTTTATAATTCTAAAGTTTATATGATTAATGGAAATAAAC
TAGTTAAATTTTTAAAAAGAAAAAATTTACTTTATACATATCAAAACTTTTTGAGGTACCCACCAAAAAATCCAAGA
GAAAATGGACTTAAAGACTATTTAGACGCTCAAAATGTTAAGCAAAGTGAATGGGAAGCATTTGTGAGTTATTCTG
AAAAGGTCAATCAAGGTAAGAAATATGGTAACACACGTCCTAAACCGCTAAATGATTTACACTTAATGGTAAGAG
ACGGTCAAAATAAAGTGTATCTTCCAGGTAGTTCAATCAAAGGTGCTATCAAACAACTCTCGTGTCAAAATATAA
TAATGAAAAAACAAAGACATTTATAGCAAAATTAAAGTCAGCGATTCAAAACCTATTGATGAAAGTAATTTAGCG
ATTTATCAAAAAATAGACATTAATAAAAGTGAAAAATCAATGCCTTTATATAGAGAGTGCATAGATGTAAATACCG
AAATAAAATTTAAGTTAACAATTGAAGATGAAATTTATTCTATTAATGAAATTGAACAAAGTATCCAAGATTTTTAC
AAAAACTATTATGATAAATGGTTAGTCGGATTCAAAGAAACAAAAGGTGGAAGACGATTTGCATTAGAGGGCGGT
ATACCAGATGTCCTAAATCAGAATATTTTGTTCTTAGGTGCTGGGACAGGATTTGTTAGTAAAACAACACACTATCA
ATTAAAAAATCGAAAACAAGCTAAACAAGATTCTTTTGAGATTTTAACTAAAAAATTCCGAGGAACTTATGGGAAA
ATGAAGGAAATACCTTCTAACGTACCAGTTGCTTTAAAAGGAACAACTAATCAAAGTCGTCATACTTCATATCAGC
AAGGAATGTGTAAAGTGAGTTTTCAAGAGTTAAATAATGAGGTGCTATAATGAAAATATTATTTAGTCCAATAGGT
AATTCAGATCCATGGAGAAATGATAGAGATGGTGCGATGCTTCATATCGTGCGTCATTATAATTTAGATAAGGTTG
TATTATATTTTACTAGAACTATTTGGGAAGGAAATGAAAATAGAAAAGGCCATAAAATTTACGAATGGGAAAAAA
TTATCCAAACTGTTTCTCCAAATACTGAAGTAGAAATCATTATTGAAAATGTAGACAATGCTCAAGATTATGATGTC
TTCAAGGAGAAATTTCATAAGTATTTAAAAATAATTGAAGATAGCTATGAAGATTGTGAAATAATTTTGAATGTCA
CTAGTGGTACACCCCAAATGGAATCAACATTATGTTTAGAATATATCGTCTATCCTGAAAATAAGAAGTGTGTACA
AGTGAGCACGCCAACTAAGGATAGTAATGCAGGTATCGAATATTCAAATCCTAAAGATAAAGTAGAAGAATTTGA
```

-continued

AATAGTCAATGAAGTAGAAAAGAAATCTGAAAAACGTTGTAAAGAAATAAACATTTTAAGCTTTAGAGAAGCAAT

GATTAGATCTCAAATTCTCGGTTTAATAGATAATTATGATTATGAAGGTGCTCTTAATTTAGTAAGTAATCAAAAT

CTTTTCGCAATGGGAAATTATTAAGAAAAAAACTACTATCATTAACAAAACAAATTAAAACACATGAAGTTTTTCCA

GAAATTAATGAGAAGTACAGAGATGATGCTTTAAAAAAATCACTATTTCATTATTTACTGTTAAATATGAGATATAA

TCGTCTTGATGTAGCTGAAACGTTAATTAGAGTAAAATCTATTGCTGAGTTTATACTTAAAACATACATTGAGATTC

ATTGGCCTACTTTAATAATTGAAAAGATGGTAAACCTTATCTAAATGATGAAGATAATTTATCTTTTGTTTATAAAT

ATAATCTGTTATTAGAAAAAGAAACAAAATTTTGATGTTTCAAGAATTTTGGGACTTCCTGCATTCATTGATATA

CTCACAATTTTAGAACCTAATTCTCAACTATTAAAAGAAGTCAATGCAGTAAACGATATAAATGGTTTAAGAAATTC

CATAGCCCATAATTTAGATACATTAAATTTGGATAAAAATAAAAATTATAAGAAAATAATGTTATCTGTTGAAGCG

ATAAAGAATATGTTACACATCTCATTTCCTGAGATAGAGGAAGAAGACTATAATTATTTTGAAGAAAAAAATAAGG

AATTTAAAGAGCTATTATGATAAATAAAATTACAGTAGAGTTAGACTTGCCAGAAAGTATTCGGTTTCAATATTTAG

GAAGTGTTTTACATGGTGTGTTAATGGATTATCTATCTGATGATATTGCTGACCAATTACATCATGAATTTGCTTAT

AGCCCATTGAAACAAAGAATATATCATAAAAATAAAAAAATCATTTGGGAAATTGTATGTATGTCAGATAATTTAT

TTAAAGAGGTTGTTAAACTATTTAGTTCTAAAAATAGTTTGCTTTTGAAATATTATCAAACAAATATTGACATTCAAT

CATTTCAAATTGAGAAGATAAATGTTCAGAACATGATGAACCAACTGTTACAAGTAGAAGATCTAAGTCGTTATGTA

CGTCTTAATATACAAACACCTATGTCTTTTAAATATCAGAACAGTTACATGATTTTTCCTGATGTTAAACGTTTTTTT

AGAAGTATTATGATACAATTTGACGCGTTTTTTGAAGAATATAGAATGTACGACAAAGAAACATTAAATTTTCTAG

AAAAGAATGTTAATATTGTTGACTACAAATTGAAAAGTACACGTTTTAACTTGGAAAAAGTTAAAATTCCTTCATTT

ACAGGAGAAATAGTATTTAAAATTAAAGGACCCTTACCTTTTCTACAGTTAACTCATTTTTTATTAAAGTTTGGCGA

ATTTTCAGGTTCAGGTATAAAAACAAGCTTAGGTATGGGAAAATATAGTATAATTTAATTAAGACATAGTTAAAAT

TTAGTTGTCAAAA cas10/csm1 gene sequence (SEQ ID NO: 2)

ATGAATAAAAAAAATATATTAATGTATGGCTCTTTATTACATGATATAGGGAAAATTATATATCGAAGTGGTGATC

ATACATTTTCAAGAGGTACGCATTCAAAATTAGGTCATCAATTTTTGTCCCAATTTTCAGAATTTAAAGACAACGAA

GTGCTTGATAACGTTGCTTATCATCATTACAAAGAACTCGCAAAAGCTAATTTAGATAATGATAATACAGCTTATAT

TACCTATATTGCGGATAATATTGCGAGTGGTATTGATAGAAGAGATATTATAGAAGAAGGCGATGAAGAATACGA

AAAACAACTATTTAATTTTGATAAATATACACCGCTATATAGTGTGTTTAATATTGTGAATTCTGAAAAATTGAAAC

AAACAAACGGGAAGTTTAAATTTTCTAATGAAAGTAATATTGAATATCCTAAAACTGAAAACATTCAATATTCAAGT

GGAAATTATACAACATTAATGAAAGATATGAGTCATGATTTAGAGCACAAATTAAGTATTAAAGAAGGTACATTTC

CTTCATTATTACAATGGACGGAAAGTCTATGGCAATATGTACCTAGTTCGACAAATAAAAACCAATTAATTGATATT

TCTCTTTATGATCATAGTCGTATTACATGTGCCATCGCCAGTTGTATATTTGATTATTTAAATGAAAATAACATACAT

AATTACAAAGATGAATTGTTCTCAAAGTATGAAAATACCAAATCATTTTATCAAAAGAAGCTTTTTTACTACTTAG

TATGGATATGAGTGGTATTCAAGATTTTATTTACAATATAAGCGGTTCTAAAGCATTAAAGAGTCTAAGATCTCGTA

GTTTTTATTTAGAACTCATGCTTGAAGTAATCGTTGATCAATTATTAGAAAGATTAGAATTAGCACGAGCAAATCTT

TTGTATACAGGTGGTGGCCATGCTTATTTATTAGTGTCTAATACTGATAAAGTGAAGAAAAAAATAACTCAATTTA

ATAATGAATTAAAAAAATGGTTTATGTCAGAATTTACTACAGATCTTTCATTATCAATGGCTTTTGAAAAATGTAGT

GGCGATGATTTAATGAATACAAGTGGTAATTATAGAACTATTTGGCGTAATGTTAGCAGCAAACTTTCTGATATTA

AAGCGCATAAATATTCCGCGGAAGATATATTAAAATTAAATCATTTTCATTCGTATGGAGATCGGGAATGTAAAGA

ATGTTTAAGAAGTGACATAGATATTAATGATGATGGACTATGTAGTATATGTGAAGGAATTATTAATATATCAAAT

GATTTAAGAGATAAATCATTCTTTGTACTGTCAGAAACTGGAAAATTAAAAATGCCATTCAATAAATTTATATCGGT

-continued

TATTGATTATGAAGAGGCAGAAATGTTAGTACAAAATAATAATCAAGTTCGTATTTACAGTAAAAATAAACCATAT

ATAGGCATAGGAATATCAACAAATTTATGGATGTGTGATTACGACTATGCTAGTCAAAATCAAGATATGAGAGAA

AAAGGTATTGGAAGTTATGTAGATAGAGAAGAAGGGGTTAAGCGTTTAGGCGTGGTACGTGCCGATATAGATAA

TCTCGGTGCTACATTTATATCTGGAATTCCAGAAAAATATAATTCAATTTCAAGAACAGCTACATTGTCTCGTCAATT

ATCATTATTTTTTAAATACGAATTAAATCATTTATTAGAAAATTATCAAATTACTGCTATATATTCAGGCGGTGACGA

TTTATTTTTAATCGGTGCATGGGATGACATTATAGAAGCAAGCATTTATATAAATGACAAATTTAAAGAGTTTACTC

TTGATAAACTAACATTGTCTGCCGGGGTTGGAATGTTTAGTGGTAAGTACCCAGTTTCTAAAATGGCTTTTGAGAC

AGGACGACTTGAAGAAGCGGCTAAGACTGGTGAAAAAAATCAGATATCTCTTTGGTTACAAGAAAAAGTATATAA

CTGGGATGAGTTTAAAAAGAATATCTTAGAAGAAAAACTTCTCGTTTTACAACAGGGGTTTTCTCAAACAGATGAA

CACGGGAAAGCCTTCATTTATAAAATGCTCGCTTTACTGAGAAATAATGAAGCTATTAATATTGCTCGTTTAGCTTA

CTTATTAGCAAGAAGCAAGATGAATGAGGATTTTACGTCTAAAATTTTTAATTGGGCTCAAAACGACAAAGATAAA

AATCAATTAATTACAGCGTTAGAGTATTATATTTATCAAATAAGGGAGGCTGATTGA csm2 gene sequence
(SEQ ID NO: 3)
ATGATATTAGCTAAAACTAAAAGTGGTAAAACGATAGATTTGACTTTTGCACATGAGGTCGTAAAAAGTAATGTAA

AAAATGTTAAAGATAGAAAAGGCAAAGAAAAACAAGTTTTATTTAACGGGCTTACAACAAGCAAGTTAAGAAATT

TAATGGAGCAGGTAAATAGACTTTATACTATTGCATTTAATTCGAATGAGGATCAATTGAATGAAGAATTCATTGA

TGAATTAGAATATTTAAAAATTAAATTTTATTATGAAGCAGGACGAGAAAAAAGCGTTGATGAATTTTTAAAAAAA

ACATTGATGTTTCCAATTATTGATAGAGTGATAAAAAAAGAATCAAAAAAATTTTTCTTAGATTATTGTAAATACTT

TGAAGCTTTAGTTGCATACGCTAAATATTATCAAAAGGAGGATTAA csm3 gene sequence
(SEQ ID NO: 4)
ATGTATTCAAAAATTAAAATTTCAGGAACAATTGAAGTAGTTACTGGTTTACACATCGGCGGAGGCGGTGAATCTA

GTATGATTGGAGCAATTGATTCTCCTGTAGTTAGAGATTTGCAAACCAAATTACCTATCATACCTGGCAGTTCAATC

AAAGGAAAAATGAGAAATTTATTAGCAAAACATTTTGGCTTGAAAATGAAACAAGAGAGTCATAACCAAGATGAT

GAACGTGTATTAAGATTATTTGGCTCAAGTGAAAAAGGAAATATCCAAAGAGCTCGTCTACAAATTTCTGATGCAT

TCTTTTCTGAAAAGACAAAAGAGCATTTTGCGCAAAATGATATTGCCTATACAGAAACGAAATTTGAGAATACAAT

TAATCGTTTAACTGCAGTTGCAAACCCAAGACAAATTGAAAGAGTAACAAGAGGATCTGAGTTTGACTTTGTATTT

ATTTACAATGTCGATGAAGAGTCGCAAGTTGAGGATGATTTTGAGAATATTGAAAAAGCGATTCACTTATTAGAGA

ATGACTATCTTGGTGGCGGCGGAACTAGAGGTAACGGACGTATTCAATTTAAAGATACAAATATCGAGACAGTTG

TTGGAGAATACGATAGTACAAATCTTAAAATTAAGTAG c5m4 gene sequence
(SEQ ID NO: 5)
ATGACATTGGCAACAAAAGTATTTAAACTTTCTTTTAAGACTCCTGTTCATTTTGGAAAAAAACGGTTGTCAGATGG

TGAAATGACAATCACTGCTGATACTTTGTTTAGTGCTTTATTTATTGAAACACTTCAATTGGGTAAAGATACCGATT

GGTTATTAAATGATTTAATCATTAGTGATACATTTCCTTATGAGAATGAGCTTTATTATCTTCCTAAACCTTTGATAA

AAATTGACTCTAAAGAAGAAGATAACCATAAAGCATTTAAAAAGTTAAAATATGTTCCGGTTCATCACTATAATCA

ATATTTAAATGGAGAGTTAAGCGCTGAAGATGCGACAGATTTAAATGATATTTTTAATATTGGGTATTTTTCTCTAC

AAACAAAGGTTTCATTAATAGCACAAGAAACTGATTCAAGTGCTGATAGTGAACCTTATTCAGTGGGAACATTTAC

TTTTGAACCTGAAGCGGGTTTATATTTTATTGCAAAAGGATCAGAAGAAACGCTTGACCATTTAAATAATATTATGA

CTGCATTACAGTATTCAGGTTTAGGTGGTAAACGTAATGCAGGATACGGACAATTTGAATATGAAATAATAAATAA

TCAACAACTATCTAAGTTACTGAATCAAAATGGAAAACATTCTATTCTTTTATCAACGGCAATGGCTAAAAAAGAA

GAGATAGAGAGTGCTTTAAAAGAGGCGAGATACATTTTAACTAAACGTTCTGGTTTCGTACAATCAACGAATTATT

CTGAAATGCTAGTTAAAAAAAGTGATTTCTATAGCTTTTCTTCGGGTTCAGTTTTTAAAAATATCTTTAATGGTGATA

TTTTTAATGTTGGCCATAATGGTAAACACCCAGTCTATCGCTATGCAAAACCTTTATGGTTGGAGGTATAA csm5 gene sequence (SEQ ID NO: 6)

ATGACAATAAAAAATTATGAAGTCGTTATTAAAACTTTAGGTCCAATTCATATTGGTAGTGGTCAAGTTATGAAGA

AGCAAGATTACATTTATGACTTTTATAATTCTAAAGTTTATATGATTAATGGAAATAAACTAGTTAAATTTTTAAAAA

GAAAAAATTTACTTTATACATATCAAAACTTTTTGAGGTACCCACCAAAAAATCCAAGAGAAATGGACTTAAAGA

CTATTTAGACGCTCAAAATGTTAAGCAAAGTGAATGGGAAGCATTTGTGAGTTATTCTGAAAAGGTCAATCAAGGT

AAGAAATATGGTAACACACGTCCTAAACCGCTAAATGATTTACACTTAATGGTAAGAGACGGTCAAAATAAAGTGT

ATCTTCCAGGTAGTTCAATCAAAGGTGCTATCAAAACAACTCTCGTGTCAAAATATAATAATGAAAAAACAAAGA

CATTTATAGCAAAATTAAAGTCAGCGATTCAAAACCTATTGATGAAAGTAATTTAGCGATTTATCAAAAAATAGAC

ATTAATAAAAGTGAAAAATCAATGCCTTTATATAGAGAGTGCATAGATGTAAATACCGAAATAAAATTTAAGTTAA

CAATTGAAGATGAAATTTATTCTATTAATGAAATTGAACAAAGTATCCAAGATTTTTACAAAAACTATTATGATAAA

TGGTTAGTCGGATTCAAAGAAACAAAAGGTGGAAGACGATTTGCATTAGAGGGCGGTATACCAGATGTCCTAAAT

CAGAATATTTTGTTCTTAGGTGCTGGGACAGGATTTGTTAGTAAAACAACACACTATCAATTAAAAAATCGAAAAC

AAGCTAAACAAGATTCTTTTGAGATTTTAACTAAAAAATTCCGAGGAACTTATGGGAAAATGAAGGAAATACCTTC

TAACGTACCAGTTGCTTTAAAAGGAACAACTAATCAAAGTCGTCATACTTCATATCAGCAAGGAATGTGTAAAGTG

AGTTTTCAAGAGTTAAATAATGAGGTGCTATAA csm6 gene sequence (SEQ ID NO: 7)

ATGAAAATATTATTTAGTCCAATAGGTAATTCAGATCCATGGAGAAATGATAGAGATGGTGCGATGCTTCATATCG

TGCGTCATTATAATTTAGATAAGGTTGTATTATATTTTACTAGAACTATTTGGGAAGGAAATGAAAATAGAAAAGG

CCATAAAATTTACGAATGGGAAAAAATTATCCAAACTGTTTCTCCAAATACTGAAGTAGAAATCATTATTGAAAAT

GTAGACAATGCTCAAGATTATGATGTCTTCAAGGAGAAATTTCATAAGTATTTAAAAATAATTGAAGATAGCTATG

AAGATTGTGAAATAATTTTGAATGTCACTAGTGGTACACCCCAAATGGAATCAACATTATGTTTAGAATATATCGTC

TATCCTGAAAATAAGAAGTGTGTACAAGTGAGCACGCCAACTAAGGATAGTAATGCAGGTATCGAATATTCAAAT

CCTAAAGATAAAGTAGAAGAATTTGAAATAGTCAATGAAGTAGAAAAGAAATCTGAAAAACGTTGTAAAGAAATA

AACATTTTAAGCTTTAGAGAAGCAATGATTAGATCTCAAATTCTCGGTTTAATAGATAATTATGATTATGAAGGTGC

TCTTAATTTAGTAAGTAATCAAAAATCTTTTCGCAATGGGAAATTATTAAGAAAAAAACTACTATCATTAACAAAAC

AAATTAAAACACATGAAGTTTTTCCAGAAATTAATGAGAAGTACAGAGATGATGCTTTAAAAAAATCACTATTTCA

TTATTTACTGTTAAATATGAGATATAATCGTCTTGATGTAGCTGAAACGTTAATTAGAGTAAAATCTATTGCTGAGT

TTATACTTAAAACATACATTGAGATTCATTGGCCTACTTTAATAATTGAAAAGATGGTAAACCTTATCTAAATGAT

GAAGATAATTTATCTTTTGTTTATAAATATAATCTGTTATTAGAAAAAAGAAAACAAAATTTTGATGTTTCAAGAAT

TTTGGGACTTCCTGCATTCATTGATATACTCACAATTTTAGAACCTAATTCTCAACTATTAAAAGAAGTCAATGCAGT

AAACGATATAAATGGTTTAAGAAATTCCATAGCCCATAATTTAGATACATTAAATTTGGATAAAAATAAAAATTATA

AGAAAATAATGTTATCTGTTGAAGCGATAAAGAATATGTTACACATCTCATTTCCTGAGATAGAGGAAGAAGACTA

TAATTATTTTGAAGAAAAAAATAAGGAATTTAAAGAGCTATTATGA cas6 gene sequence (SEQ ID NO: 8)

TGATAAATAAAATTACAGTAGAGTTAGACTTGCCAGAAAGTATTCGGTTTCAATATTTAGGAAGTGTTTTACATG

GTGTGTTAATGGATTATCTATCTGATGATATTGCTGACCAATTACATCATGAATTTGCTTATAGCCCATTGAAACAA

AGAATATATCATAAAAATAAAAAAATCATTTGGGAAATTGTATGTATGTCAGATAATTTATTTAAAGAGGTTGTTA

AACTATTTAGTTCTAAAAATAGTTTGCTTTTGAAATATTATCAAACAAATATTGACATTCAATCATTTCAAATTGAGA

AGATAAATGTTCAGAACATGATGAACCAACTGTTACAAGTAGAAGATCTAAGTCGTTATGTACGTCTTAATATACA

-continued

```
AACACCTATGTCTTTTAAATATCAGAACAGTTACATGATTTTTCCTGATGTTAAACGTTTTTTTAGAAGTATTATGAT

ACAATTTGACGCGTTTTTTGAAGAATATAGAATGTACGACAAAGAAACATTAAATTTTCTAGAAAAGAATGTTAAT

ATTGTTGACTACAAATTGAAAAGTACACGTTTTAACTTGGAAAAAGTTAAAATTCCTTCATTTACAGGAGAAATAGT

ATTTAAAATTAAAGGACCCTTACCTTTTCTACAGTTAACTCATTTTTTATTAAAGTTTGGCGAATTTTCAGGTTCAGG

TATAAAACAAGCTTAGGTATGGGAAAATATAGTATAATTTAA
```

---

I claim:

1. A phage genome editing system comprising:
   a *Staphylococcus* bacterial cell that can be infected by a phage;
   a vector comprising a crRNA that can hybridize to a nucleic acid sequence of the phage; and
   a vector comprising a donor nucleic acid sequence, wherein the donor nucleic acid sequence comprises: a mutated nucleic acid sequence to be introduced into the phage, flanked by two nucleic acid sequences containing regions of homology to the phage genome.

2. The system of claim 1, wherein the *Staphylococcus* bacterial cell is selected from *Staphylococcus epidermidis* or *Staphylococcus aureus*.

3. The system of claim 1, wherein the *Staphylococcus* bacterial cell comprises an endogenous CRISPR-Cas10 system.

4. The system of claim 1, wherein the *Staphylococcus* bacterial cell has endogenous CRISPR sequences deleted.

5. The system of claim 1, wherein the phage is a lytic phage.

6. The system of claim 5, wherein the lytic phage is selected from the group consisting of a Podoviridae phage, a Myoviridae phage, and a Siphoviridae phage.

7. The system of claim 1, wherein the crRNA and the donor nucleic acid sequence are comprised on the same vector.

8. The system of claim 1, wherein the mutated nucleic acid sequence is selected from the group consisting of: at least one point mutation, an insertion mutation, and a deletion mutation.

* * * * *